US012331079B2

(12) United States Patent
McFadden et al.

(10) Patent No.: US 12,331,079 B2
(45) **Date of Patent: *Jun. 17, 2025**

(54) ONCOLYTIC VIRUS PLATFORM TO TREAT CANCERS WITH MYXOMA VIRUS

(71) Applicant: Arizona Board of Regents on behalf of Arizona State University, Scottsdale, AZ (US)

(72) Inventors: Douglas Grant McFadden, Tempe, AZ (US); Mohammed Masmudur Rahman, Chandler, AZ (US); Nancy Villa, Tempe, AZ (US); Lino Torres-Dominguez, Tempe, AZ (US); Lina Franco Achury, Tempe, AZ (US); Leslie Lynne Sharp, Rancho Santa Fe, CA (US)

(73) Assignee: Arizona Board of Regents on behalf of Arizona State University, Scottsdale, AZ (US)

(*) Notice: Subject to any disclaimer, the term of this patent is extended or adjusted under 35 U.S.C. 154(b) by 345 days.

This patent is subject to a terminal disclaimer.

(21) Appl. No.: 17/893,052

(22) Filed: Aug. 22, 2022

(65) Prior Publication Data

US 2023/0025706 A1 Jan. 26, 2023

Related U.S. Application Data

(63) Continuation of application No. 17/357,624, filed on Jun. 24, 2021, now abandoned, which is a continuation of application No. 17/010,711, filed on Sep. 2, 2020, now Pat. No. 11,117,934.

(60) Provisional application No. 62/944,233, filed on Dec. 5, 2019, provisional application No. 62/894,925, filed on Sep. 2, 2019.

(51) Int. Cl.
| | |
|---|---|
| *C07K 14/065* | (2006.01) |
| *A61K 39/275* | (2006.01) |
| *A61K 45/06* | (2006.01) |
| *A61P 35/04* | (2006.01) |
| *C07K 14/005* | (2006.01) |
| *C07K 14/525* | (2006.01) |
| *C07K 14/54* | (2006.01) |
| *C12N 7/00* | (2006.01) |
| *A61K 39/00* | (2006.01) |

(52) U.S. Cl.
CPC .......... *C07K 14/005* (2013.01); *A61K 39/275* (2013.01); *A61K 45/06* (2013.01); *A61P 35/04* (2018.01); *C07K 14/525* (2013.01); *C07K 14/5434* (2013.01); *C12N 7/00* (2013.01); *A61K 2039/5154* (2013.01); *A61K 2039/5256* (2013.01); *A61K 2039/545* (2013.01); *A61K 2039/572* (2013.01); *A61K 2039/585* (2013.01); *C07K 2319/33* (2013.01); *C12N 2710/24022* (2013.01); *C12N 2710/24033* (2013.01); *C12N 2710/24071* (2013.01)

(58) Field of Classification Search
None
See application file for complete search history.

(56) References Cited

U.S. PATENT DOCUMENTS

| | | | |
|---|---|---|---|
| 11,117,934 | B2 | 9/2021 | McFadden et al. |
| 2012/0141427 | A1 | 6/2012 | Bertagnoli et al. |
| 2013/0209406 | A1 | 8/2013 | Tenoever |
| 2014/0328804 | A1 | 11/2014 | McFadden et al. |
| 2016/0130317 | A1 | 5/2016 | Medin et al. |
| 2017/0080106 | A1 | 3/2017 | Yun et al. |
| 2018/0080048 | A1 | 3/2018 | Kim et al. |
| 2018/0303886 | A1 | 10/2018 | Hwang et al. |
| 2019/0076460 | A1 | 3/2019 | Ding |
| 2019/0160115 | A1 | 5/2019 | Falb et al. |
| 2021/0061864 | A1 | 3/2021 | McFadden et al. |
| 2021/0268050 | A1 | 9/2021 | McFadden et al. |
| 2021/0324014 | A1 | 10/2021 | McFadden et al. |

FOREIGN PATENT DOCUMENTS

| | | | |
|---|---|---|---|
| CN | 104093830 | A | 10/2014 |
| CN | 110050062 | A | 7/2019 |
| EP | 0972840 | B1 | 5/2004 |
| WO | WO-2007143545 | A2 | 12/2007 |
| WO | WO-2015078856 | A1 | 6/2015 |
| WO | WO-2020014670 | A1 | 1/2020 |
| WO | WO-2020033510 | A1 | 2/2020 |
| WO | WO-2020037206 | A1 | 2/2020 |
| WO | WO-2020051248 | A1 | 3/2020 |
| WO | WO-2020198690 | A1 | 10/2020 |
| WO | WO-2021046048 | A1 | 3/2021 |

(Continued)

OTHER PUBLICATIONS

Balkwill. Tumour necrosis factor and cancer. Nat Rev Cancer 9(5):361-371 (2009).

(Continued)

*Primary Examiner* — Michael D Burkhart
(74) *Attorney, Agent, or Firm* — Riverside Law LLP

(57) ABSTRACT

Disclosed herein, in certain embodiments, are recombinant myxoma viruses (MYXVs) and nucleic acid constructs encoding the recombinant MYXVs. In some embodiments, the MYXVs are engineered to inactivate or attenuate an activity or expression level of an M153 protein. In some embodiments, the MYXVs are engineered to express one or more transgenes such as a tumor necrosis factor (TNF), interleukin-12 (IL-12), or decorin. Also disclosed herein, in certain embodiments, are methods of using the MYXVs. Some embodiments include providing a MYXV as described herein to a subject in need thereof.

20 Claims, 24 Drawing Sheets

(56) References Cited

FOREIGN PATENT DOCUMENTS

WO  WO-2021046125 A1  3/2021
WO  WO-2022187148 A2  9/2022

OTHER PUBLICATIONS

Barrett et al. M135R is a Novel Cell Surface Virulence Factor of Myxoma Virus. Journal of Virology 81(1):106-114 (2007).
Bartee et al., Selective purging of human multiple myeloma cells from autologous stem cell transplant grafts using oncolytic myxoma virus. Biol Blood Marrow Transplant 18(10):1540-1551 (2012).
Bartee et al. The addition of tumor necrosis factor plus beta interferon induces a novel synergistic antiviral state against poxviruses in primary human fibroblasts. Journal of virology 83:498-511 (2009).
Burton et al. Targeting TNF-alpha for cancer therapy. J Biol 8:85 (2009).
Cameron et al., The complete DNA sequence of myxoma virus. Virology 264(2):298-318 (1999).
Chan et al., Oncolytic Myxoma Virus: The path to clinic. Vaccine 31(39):4252-4258 (2013).
Chan et al., Oncolytic Poxviruses. Annu Rev Virol 1(1):119-141 (2014).
Choi et al., Strengthening of antitumor immune memory and prevention of thymic atrophy mediated by adenovirus expressing IL-12 and GM-CSF. Gene Ther 19(7):711-723 (2012).
Coley. The treatment of malignant tumors by repeated inoculations of erysipelas: with a report of ten original cases. Am. J. Med. Sci. 105:487-511 (1893).
Collin et al., The poxviral scrapin MV-LAP requires a myxoma viral infection context to efficiently downregulate MHC-I molecules. Virology 343(2):171-178 (2005).
Colombo et al. Interleukin-12 in anti-tumor immunity and immunotherapy. Cytokine Growth Factor Rev. 13(2):155-168 (2002).
Dai et al.: Myxoma virus induces type I interferon production in murine plasmacytoid dendritic cells via a TLR9/MyD88-, IRF5/IRF7-, and IFNAR-dependent pathway. J Virol. 85(20):10814-10825 (2011).
Del Vecchio et al., Interleukin-12: biological properties and clinical application. Clin Cancer Res 13(16):4677-4685 (2007).
GenBank Accession No. AF170726.2 (2019).
GenBank Accession No. EU552530 (2019).
GenBank Accession No. EU552531 (2019).
Guerin et al., Myxoma Virus Leukemia-Associated Protein is Responsible for Major Histocompatibility Complex Class I and Fas-CD95 Down-Regulation and Defines Scrapins, a New Group of Surface Cellular Receptor Abductor Proteins. J Virol 76(6):2912-2923 (2002).
Harrington et al., Optimizing Oncolytic Virotherapy in Cancer Treatment. Nat. Reviews Drug Discovery 19:689-706 (2019).
Hess et al., Antitumor efficacy of a human interleukin-12 expression plasmid demonstrated in a human peripheral blood leukocyte/human lung tumor xenograft SCID mouse model. Cancer Gene Ther 8(5):371-377 (2001).
Kashii et al., Constitutive expression and role of the TNF family ligands in apoptotic killing of tumor cells by human NK cells. J Immunol 163(10):5358-5366 (1999).
Kelly et al. History of oncolytic viruses: genesis to genetic engineering. Molecular Therapy 15:651-659 (2007).
Kim et al., Myxoma virus targets primary human leukemic stem and progenitor cells while sparing normal hematopoietic stem and progenitor cells. Leukemia 23(12):2313-2317 (2009).
Laverty et al., TGF-beta3 and cancer: a review. Cytokine Growth Factor Rev 20(4):305-317 (2009).
Lichty et al. Going viral with cancer immunotherapy. Nature Reviews Cancer 14:559-567 (2014).
Lilly et al., Ex vivo oncolytic virotherapy with myxoma virus arms multiple allogeneic bone marrow transplant leukocytes to enhance graft versus tumor. Molecular Therapy Oncolytics 4:31-40 (2016).
Liu et al. Myxoma virus expressing interleukin-15 fails to cause lethal myxomatosis in European rabbits. J Virol. 83(11):5933-5938 (2009).
Liu et al., The immunoregulatory properties of oncolytic myxoma virus and their implications in therapeutics. Microbes Infect 12(14-15):1144-1152 (2010).
Mansouri et al., The PHD/LAP-Domain Protein M153R of Myxomavirus Is a Ubiquitin Ligase That Induces the Rapid Internalization and Lysosomal Destruction of CD4. J Virol 77(2):1427-1440 (2003).
Moriwaki et al., Differential roles of RIPK1 and RIPK3 in TNF-induced necroptosis and chemotherapeutic agent-induced cell death. Cell Death Dis 6(2):e1636 (2015).
Mossman et al. Myxoma virus M-T7, a secreted homolog of the interferon-gamma receptor, is a critical virulence factor for the development of myxomatosis in European rabbits. Virology 215:17-30 (1996).
Nayerossadat et al. Viral and nonviral delivery systems for gene delivery. Adv Biomed Res 1:27 (2012).
Neill et al., Decorin as a multivalent therapeutic agent against cancer. Adv Drug Deliv Rev 97:174-185 (2016).
Ogbomo et al., Myxoma Virus Infection Promotes NK Lysis of Malignant Gliomas In Vitro and In Vivo. PLoS One 8(6): e66825 (2013).
PCT/US2019/041700 International Search Report and Written Opinion dated Nov. 12, 2019.
PCT/US2020/049061 International Search Report and Written Opinion dated Dec. 7, 2020.
PCT/US2020/055083 International Search Report and Written Opinion dated Jan. 26, 2021.
PCT/US2022/018164 International Invitation to Pay Additional Fees dated Jun. 7, 2022.
PCT/US2022/018164 International Search Report and Written Opinion dated Sep. 6, 2022.
Prevost-Blondel et al., Crucial Role of TNF-α in CD8 T Cell-Mediated Elimination of 3LL-A9 Lewis Lung Carcinoma Cells In Vivo. J Immunol 164(7):3645-3651 (2000).
Rahman et al., Methods for Identifying Virus-Derived Serpins: Methods and Protocols. Methods in molecular biology 1826:73-86 (2018).
Russell et al. Oncolytic virotherapy. Nature Biotechn 30:658-670 (2012).
Stanford et al., Myxoma virus and oncolytic virotherapy: a new biologic weapon in the war against cancer. Expert Opin Biol Ther 7(9):1415-1425 (2007).
Stanford et al., Myxoma Virus Expressing Human Interleukin-12 Does Not Induce Myxomatosis in European Rabbits. Journal of Virology 81(22):12704-12708 (2007).
Sypula et al., Myxoma virus tropism in human tumor cells. Gene therapy & molecular biology 8:103-114 (2004).
U.S. Appl. No. 17/010,711 Office Action dated Dec. 24, 2020.
U.S. Appl. No. 17/357,624 Office Action dated Mar. 21, 2022.
U.S. Appl. No. 17/357,624 Office Action dated Nov. 12, 2021.
Villa et al., Myxoma virus suppresses proliferation of activated T lymphocytes yet permits oncolytic virus transfer to cancer cells. Blood 125(24): 3778-3788 (2015).
Wang et al., Infection of human cancer cells with myxoma virus requires Akt activation via interaction with a viral ankyrin-repeat host range factor. PNAS 103(12):4640-4645 (2006).
Wang et al. RIG-I Mediates the Co-Induction of Tumor Necrosis Factor and Type I Interferon Elicited by Myxoma Virus in Primary Human Macrophages. PLoS Pathog 4(7):e1000099 (2008).
Xu et al., The systemic delivery of an oncolytic adenovirus expressing decorin inhibits bone metastasis in a mouse model of human prostate cancer. Gene Ther 22(3):247-256 (2015).
Yao et al., Decorin-mediated inhibition of the migration of U87MG glioma cells involves activation of autophagy and suppression of TGF-β signaling. FEBS Open Bio 6(7):707-719 (2016).
Yu et al. Targeting Transmembrane TNF-a Suppresses Breast Cancer Growth. Cancer Res 73(13):4061-4075 (2013).
Zhang et al., Optimizing DC vaccination by combination with oncolytic adenovirus coexpressing IL-12 and GM-CSF. Mol Ther 19(8):1558-1568 (2011).

ONCOLYTIC VIRUS PLATFORM TO TREAT CANCERS WITH MYXOMA VIRUS

CROSS REFERENCE

This application is a continuation of U.S. application Ser. No. 17/357,624, filed Jun. 24, 2021, which is a continuation of U.S. application Ser. No. 17/010,711, filed Sep. 2, 2020, now issued as U.S. Pat. No. 11,117,934, which claims priority to U.S. provisional application No. 62/894,925, filed Sep. 2, 2019, and U.S. provisional application No. 62/944,233, filed Dec. 5, 2019, each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Aug. 22, 2022, is named 55842-711_302_SL.txt and is 72,974 bytes in size.

STATEMENT AS TO FEDERALLY SPONSORED RESEARCH

This invention was made with government support under P50 CA186781 awarded by the National Institutes of Health. The government has certain rights in the invention.

FIELD

Disclosed herein are recombinant myxoma viruses (MYXVs), nucleic acid constructs encoding recombinant MYXVs, and methods of use thereof.

BACKGROUND

Current treatments used to treat various types of cancer tend to work by poisoning or killing the cancerous cell, but treatments that are toxic to cancer cells typically tend to be toxic to healthy cells as well. Moreover, the heterogenous nature of tumors is one of the primary reasons that effective treatments for cancer remain elusive. Current mainstream therapies such as chemotherapy and radiotherapy tend to be used within a narrow therapeutic window of toxicity. These types of therapies have limited applicability due to the varying types of tumor cells and the limited window in which these treatments can be administered.

SUMMARY

Disclosed herein in some aspects is a myxoma virus (MYXV) having enhanced anti-cancer activity, wherein the myxoma virus is genetically engineered to attenuate an activity or expression level of its M153 protein.

In certain embodiments, the activity or the expression level of the M153 protein is attenuated at least 80%. Alternatively and/or additionally, MYXV is engineered to introduce a mutation in a nucleic acid encoding the M153 protein, wherein the mutation comprises an insertion, deletion, or substitution mutation. In some embodiments, the mutation enhances cell immune response activity in relation to a wild-type M153 protein. In certain embodiments, at least a portion of a nucleic acid encoding the M153 protein in MYXV genome is knocked out. In some embodiments, the MYXV comprises an inhibitory molecule targeting M153 transcript that thereby attenuates the M153 protein expression. In some embodiments, the inhibitory molecule is an inhibitory RNA. In some embodiments, the inhibitory RNA comprises dsRNA, siRNA, antisense RNA, or miRNA. In some embodiments, the MYXV further comprises a nucleic acid encoding a non-viral molecule. In some embodiments, the non-viral molecule is tumor necrosis factor alpha (TNFα). In some embodiments, the TNFα is human TNFα. In some embodiments, the TNFα is a soluble peptide. In some embodiments, the TNFα is a membrane- or surface-bound peptide. In some embodiments, the TNFα further enhances the anti-cancer activity of the MYXV by activating anti-tumor immune cells or inducing cancer cell death. In some embodiments, the non-viral molecule is interleukin-12 (IL-12). In some embodiments, the IL-12 is human IL12. In some embodiments, the IL-12 is a soluble peptide. In some embodiments, the IL-12 is a membrane- or surface-bound peptide. In some embodiments, the IL-12 further enhances the anti-cancer activity of the MYXV by promoting immune cell differentiation or eliciting immune cell cytotoxicity. In some embodiments, the IL-12 comprises an IL-12α subunit and an IL-12β subunit. In some embodiments, the IL-12α subunit and the IL-12β subunit are joined by a polypeptide linker. In some embodiments, the polypeptide linker is an elastin linker. In some embodiments, the non-viral molecule is decorin. In some embodiments, the decorin is human decorin. In some embodiments, the decorin is a soluble peptide. In some embodiments, the decorin is a membrane- or surface-bound peptide. In some embodiments, the decorin further enhances the anti-cancer activity of the MYXV by blocking or decreasing TGF-β signaling. In some embodiments, the nucleic acid encodes at least two molecules selected from a group consisting of TNFα, IL-12, and decorin. In some embodiments, the nucleic acid encodes TNFα, IL-12, and decorin. In some embodiments, the MYXV is derived from a Lausanne strain.

Disclosed herein, in some aspects, is a composition comprising a MYXV of any of the above embodiments, and a pharmaceutically acceptable carrier or excipient.

In some embodiments, the composition is formulated for systemic administration. In some embodiments, the composition is formulated for local administration. In some embodiments, the composition is formulated for parenteral administration.

Disclosed herein, in some aspects is a composition comprising a plurality of cells treated ex vivo by the MYXV of any of the above embodiments, wherein the plurality of cells comprises peripheral blood mononuclear cells (PBMCs), bone marrow (BM) cells, or a combination thereof.

Disclosed herein, in some aspects is a method of inhibiting, alleviating, or preventing a cancer in a subject in need thereof, comprising administering to the subject the MYXV or the composition of any one of the above embodiments.

In some embodiments, the subject has, is suspected of having, or is at risk of having the cancer, and wherein the method further comprises selecting the subject. In some embodiments, the subject is a human. In some embodiments, the administration is systemic administration. In some embodiments, the administration reduces cancer cell viability, or activates immunogenic cell death in the cancer. In some embodiments, the administration improves the subject's survival. In some embodiments, the cancer comprises a solid tumor. In some embodiments, the cancer is an osteosarcoma, triple negative breast cancer, or melanoma. In some embodiments, the cancer has metastasized to a location in the subject. In some embodiments, the location comprises a lung, a brain, a liver and/or a lymph node of the subject. In some embodiments, the method further comprises administering to the subject an additional therapeutic agent. In some embodiments, the additional therapeutic agent is an immune checkpoint modulator. In some embodiments, the additional therapeutic agent is administered to the subject before administering the composition. In some embodiments, the additional therapeutic agent is administered to the subject after administering the composition. In some embodiments, the additional therapeutic agent is administered to the subject as a combination with the composition. In some embodiments, the composition comprising the plurality of cells is administered to the subject, wherein the plurality of cells comprises cells that are autologous to the subject. In some embodiments, the composition comprising the plurality of cells is administered to the subject, wherein the plurality of cells comprises cells that are allogenic to the subject.

Disclosed herein, in some aspects is a recombinant nucleic acid comprising at least a portion of MYXV genome, wherein the MYXV genome is modified to reduce expression of M153 gene. In some embodiments, the recombinant nucleic acid comprises DNA. In some embodiments, the portion of MYXV genome is modified to knock out at least a portion of the M153 gene in the portion of MYXV genome. In some embodiments, the recombinant MYXV genome comprises a first nucleic acid encoding TNFα. In some embodiments, the TNFα is human TNFα. In some embodiments, the first nucleic acid replaces or is adjacent to an M135R gene of the MYXV genome. In some embodiments, the first nucleic acid is inserted between an M135R gene and an M136R gene of the MYXV genome. In some embodiments, expression of the first nucleic acid is driven by a poxvirus synthetic early/late (sE/L) promoter. In some embodiments, the recombinant MYXV genome comprises a second nucleic acid encoding interleukin-12 subunit alpha (IL-12α). In some embodiments, the IL-12α is human IL-12α. In some embodiments, expression of IL-12α is driven by an internal ribosome entry site (IRES). In some embodiments, the second nucleic acid IL-12α disrupts the expression of the M153 gene of the MYXV genome. In some embodiments, the recombinant MYXV genome comprises a third nucleic acid encoding an interleukin-12 subunit beta (IL-12β). In some embodiments, the IL-12β is human IL-12β. In some embodiments, expression of the third nucleic acid is driven by an sE/L promoter. In some embodiments, the third nucleic acid disrupts the expression of the M153 gene of the MYXV genome. In some embodiments, the recombinant MYXV genome comprises a fourth nucleic acid encoding decorin. In some embodiments, the decorin is human decorin. In some embodiments, expression of the fourth nucleic acid is driven by an sE/L promoter. In some embodiments, the fourth nucleic acid disrupts expression of the M153 gene of the MYXV genome. In some embodiments, the recombinant MYXV genome further comprises a fifth nucleic acid encoding a reporter tag. In some embodiments, the reporter tag comprises a green fluorescent protein (GFP). In some embodiments, expression of the fifth nucleic acid is driven by an sE/L promoter. In some embodiments, the recombinant nucleic acid further comprises a sixth nucleic acid encoding a second reporter tag. In some embodiments, the second reporter tag comprises a red fluorescent protein (RFP). In some embodiments, expression of the sixth nucleic acid is driven by a poxvirus P11 late promoter. In some embodiments, the recombinant nucleic acid comprises a vMyx-hTNFa cassette, optionally comprising GFP. In some embodiments, the recombinant nucleic acid comprises an hDecorin-hIL-12 cassette, optionally comprising dsRed. In some embodiments, the recombinant nucleic acid comprises or consists of a vMyx-hTNFa-hDecorin-hIL-12-M153KO (vMyx-Triple) cassette, optionally comprising dsRed and/or GFP.

Disclosed herein, in some aspects, is a recombinant MYXV comprising the recombinant nucleic acid of any of the above embodiments.

Disclosed herein, in some aspects, is a method of inhibiting, alleviating, or preventing a cancer in a subject in need thereof, comprising administering to the subject the recombinant nucleic acid or the recombinant MYXV of any one of the preceding embodiments, In some embodiments, the subject has, is suspected of having, or is at risk of having the cancer, and wherein the method further comprises selecting the subject. In some embodiments, the subject is a human. In some embodiments, the administration is systemic administration. In some embodiments, the administration reduces cell viability, or activates immunogenic cell death in the cancer. In some embodiments, the administration is performed in a dose and a schedule effective to increase expression of at least two cytokines in PBMCs of the subject. In some embodiments, the administration is performed in a dose and a schedule effective to increase expression of at least two cytokines in cancer cells in the subject. In some embodiments, the at least two cytokines comprise IFN-γ, IL-2, IL-6, IL-10, IL-12, or TNF-α. In some embodiments, the administration is performed in a dose and a schedule effective to reduce volume of the cancer by at least 10%. In some embodiments, wherein the administration is performed in a dose and a schedule effective to reduce growth of the cancer by at least 10%.

Disclosed herein, in some aspects, is a myxoma virus (MYXV) having enhanced anti-cancer activity, wherein the MYXV is genetically engineered to attenuate an activity or expression level of its M153 protein.

In some embodiments, the activity or the expression level of the M153 protein is attenuated at least 80%. In some embodiments, the MYXV is engineered to introduce a mutation in a nucleic acid encoding the M153 protein, wherein the mutation comprises an insertion, deletion, or substitution mutation. In some embodiments, at least a portion of a nucleic acid encoding the M153 protein in MYXV genome is knocked out. In some embodiments, the MYXV comprises an inhibitory molecule targeting M153 transcript that thereby attenuates the M153 protein expression, wherein the inhibitory molecule comprises dsRNA, siRNA, antisense RNA, or miRNA. In some embodiments, the MYXV is further genetically engineered to express a non-viral molecule. In some embodiments, the non-viral molecule is a cytokine or a cell matrix protein. In some embodiments, the non-viral molecule is tumor necrosis factor alpha (TNFα), interleukin-12 subunit alpha (IL-12α), interleukin-12 subunit beta (IL-12β), or decorin. In some embodiments, the non-viral molecule is a human protein. In some embodiments, the MYXV expresses at least two non-viral molecules selected from a group consisting of TNFα, IL 12α, IL-12β, and decorin.

Disclosed herein, in some aspects is a composition comprising a plurality of cells treated ex vivo by a MYXV, wherein the MYXV is genetically engineered to attenuate an activity or expression level of its M153 protein, and to express a non-viral molecule.

In some embodiments, the plurality of cells comprises peripheral blood mononuclear cells (PBMCs), bone marrow (BM) cells, or a combination thereof.

Disclosed herein, in some aspects, is recombinant nucleic acid comprising at least a portion of MYXV genome, wherein the portion of the MYXV genome is modified to reduce expression of M153 gene.

In some embodiments, the portion of MYXV genome is modified to knock out at least a portion of the M153 gene in the portion of MYXV genome. In some embodiments, the recombinant nucleic acid comprises a nucleic acid encoding a non-viral molecule. In some embodiments, the non-viral molecule is human TNFα, human IL-12α (hTNFα), human IL-12β, or human decorin. In some embodiments, the nucleic acid encoding the non-viral molecule comprises a vMyx-hTNFα cassette, and the nucleic acid encoding the non-viral molecule replaces or is adjacent to an M135R gene of the MYXV genome. In some embodiments, the nucleic acid encoding the non-viral molecule comprises a vMyx-hTNFα cassette, and the nucleic acid encoding the non-viral molecule is inserted between an M135R gene and an M136R gene of the MYXV genome. In some embodiments, the nucleic acid encoding the non-viral molecule comprises an hDecorin-hIL-12 cassette, and the nucleic acid encoding the non-viral molecule replaces at least a portion of the M153 gene of the MYXV genome. In some embodiments, the nucleic acid encoding the non-viral molecule comprises a vMyx-hTNFα-hDecorin-hIL-12-M153KO (vMyx-Triple) cassette.

Disclosed herein, in some aspects is a method of inhibiting, alleviating, or preventing a cancer in a subject in need thereof, comprising administering to the subject a MYXV or a plurality of cells treated with the MYXV, wherein the MYXV is genetically engineered to attenuate an activity or expression level of its M153 protein.

In some embodiments, the MYXV is further genetically engineered to express a non-viral molecule. In some embodiments, the non-viral molecule is tumor necrosis factor alpha (TNFα), interleukin-12 subunit alpha (IL-12α), interleukin-12 subunit beta (IL-12β), or decorin. In some embodiments, the MYXV or the plurality of cells is administered by systemic administration. In some embodiments, the administration reduces tumor cell viability, or activates immunogenic cell death in the cancer. In some embodiments, the cancer is a solid tumor, an osteosarcoma, triple negative breast cancer, or melanoma. In some embodiments, the cancer has metastasized to a lung, a brain, a liver or a lymph node in the subject. In some embodiments, the method further comprises administering to the subject an immune checkpoint modulator. In some embodiments, the administration is performed in a dose and a schedule effective to increase expression of at least two cytokines in PBMC or cancer cells of the subject, wherein the at least two cytokines comprise IFN-γ, IL-2, IL-6, IL-10, IL-12, or TNF-α. In some embodiments, the administration is performed in a dose and a schedule effective to reduce volume of the cancer at least 10%.

Disclosed herein, in some aspects, is a myxoma virus (MYXV) having enhanced anti-cancer activity, wherein the myxoma virus is genetically engineered to attenuate an activity or expression level of its M153 protein.

In some embodiments, the activity or the expression level of the M153 protein is attenuated at least 80%. In some embodiments, the MYXV is engineered to introduce a mutation to in a nucleic acid encoding the M153 protein, wherein the mutation comprises an insertion, deletion, or substitution mutation. In some embodiments, at least a portion of a nucleic acid encoding the M153 protein in MYXV genome is knocked out. In some embodiments, the MYXV comprises an inhibitory molecule targeting M153 transcript that thereby attenuates the M153 protein expression, wherein the inhibitory molecule comprises dsRNA, siRNA, antisense RNA, or miRNA. In some embodiments, the MYXV further comprises a nucleic acid encoding a non-viral molecule. In some embodiments, the non-viral molecule is tumor necrosis factor alpha (TNFα), interleukin-12 subunit alpha (IL-12α), interleukin-12 subunit beta (IL-12β), or decorin. In some embodiments, the non-viral molecule is a human protein. In some embodiments, the nucleic acid encodes at least two non-viral molecules selected from a group consisting of TNFα, IL 12α, IL-12β, and decorin.

Disclosed herein, in some aspects, is a composition comprising a plurality of cells treated ex vivo by a MYXV, wherein the MYXV is genetically engineered to attenuate an activity or expression level of its M153 protein, and wherein the plurality of cells comprises peripheral blood mononuclear cells (PBMCs), bone marrow (BM) cells, or a combination thereof.

In some embodiments, the composition is for use in inhibiting, alleviating, or preventing a cancer in a subject in need thereof, wherein the plurality of cells comprises cells that are autologous to the subject. In some embodiments, the composition is for use in inhibiting, alleviating, or preventing a cancer in a subject in need thereof, wherein the plurality of cells comprises cells that are allogeneic to the subject.

Disclosed herein, in some aspects, is a MYXV for use in inhibiting, alleviating, or preventing a cancer in a subject in need thereof, wherein the MYXV is genetically engineered to attenuate an activity or expression level of its M153 protein.

In some embodiments, the MYXV is administered to the subject by systemic administration. In some embodiments, the MYXV reduces cancer cell viability, or activates immunogenic cell death in the cancer. In some embodiments, the cancer is a solid tumor, an osteosarcoma, triple negative breast cancer, or melanoma. In some embodiments, the cancer has metastasized to a lung, a brain, a liver or a lymph node in the subject. In some embodiments, the MYXV is administered to the subject with an immune checkpoint modulator. In some embodiments, the MYXV is administered in a dose and a schedule effective to increase expression of at least two cytokines in PBMC or cancer cells of the subject, wherein the at least two cytokines comprise IFN-γ, IL-2, IL-6, IL-10, IL-12, or TNF-α. In some embodiments, the MYXV is administered in a dose and a schedule effective to reduce volume of the cancer at least 10%.

Disclosed herein, in some aspects is a recombinant nucleic acid comprising at least a portion of MYXV genome, wherein the portion of the MYXV genome is modified to reduce expression of M153.

In some embodiments, the portion of MYXV genome is modified to knock out at least a portion of the M153 gene in the portion of MYXV genome. In some embodiments, the recombinant nucleic acid comprises a nucleic acid encoding a non-viral molecule. In some embodiments, the non-viral molecule is tumor necrosis factor alpha (TNFα), interleukin-12 subunit alpha (IL-12α), interleukin-12 subunit beta (IL-12β), or decorin. In some embodiments, the non-viral molecule is a human protein. In some embodiments, the nucleic acid encoding the non-viral molecule is inserted between an M135R gene and an M136R gene of the MYXV genome. In some embodiments, the nucleic acid encoding the non-viral molecule is inserted to replace at least a portion of the M153 gene of the MYXV genome. In some embodiments, the nucleic acid encoding the non-viral molecule comprises a vMyx-hTNFα cassette, optionally comprising GFP, and the nucleic acid encoding the non-viral molecule replaces or is adjacent to an M135R gene of the MYXV genome. In some embodiments, the nucleic acid encoding the non-viral molecule comprises a vMyx-hTNFα cassette, and the nucleic acid encoding the non-viral molecule is inserted between an M135R gene and an M136R gene of the MYXV genome. In some embodiments, the nucleic acid encoding the non-viral molecule comprises an hDecorin-hIL-12 cassette, optionally comprising dsRed, and the nucleic acid encoding the non-viral molecule replaces at least a portion of the M153 gene of the MYXV genome. In some embodiments, the nucleic acid encoding the non-viral molecule comprises a vMyx-hTNFα-hDecorin-hIL-12-M153KO (vMyx-Triple) cassette, optionally comprising dsRed.

BRIEF DESCRIPTION OF THE DRAWINGS

The novel features of certain embodiments of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 2A shows genomic viral DNA from vMyx-Triple construct clones using primers to confirm presence of hDecorin-hIL-12. FIG. 2B shows the presence of hTNFa. FIG. 2C shows the modification at locus M153 and purity of the vMyx-Triple construct. FIG. 2D shows the absence of M153 and purity of recombinant vMyx-Triple constructs. Lane 1 includes DNA from MYXV-Lau or the expression plasmid for hDec-Hil12 and hTNF. MM represents known size DNA ladder.

FIG. 7A shows ATP release caused by Doxorubicin (positive control), a wt MYXV, and a M153KO MYXV at different hours post infection (p.i.). When no bar is present, the level of ATP was below the limit of detection for the assay. FIG. 7B shows a quantitative representation of calreticulin ecto-expression for untreated (mock), doxorubicin-treated (positive control), a M135KO MYXV-infected, and a M153KO MYXV-infected cells. The data quantify ecto-expression per cell based on confocal images taken 36 hrs post-treatment, with signal normalized to a nuclear stain (DAPI) that represents each cell.

FIG. 9A shows TNF concentration. FIG. 9B shows Decorin concentration. FIG. 9C shows human IL-12 concentration. FIG. 9D shows murine IL-12 concentration. When no bar is present, the level of the analyte was below the limit of detection for the assay.

DETAILED DESCRIPTION

Figure 1A:
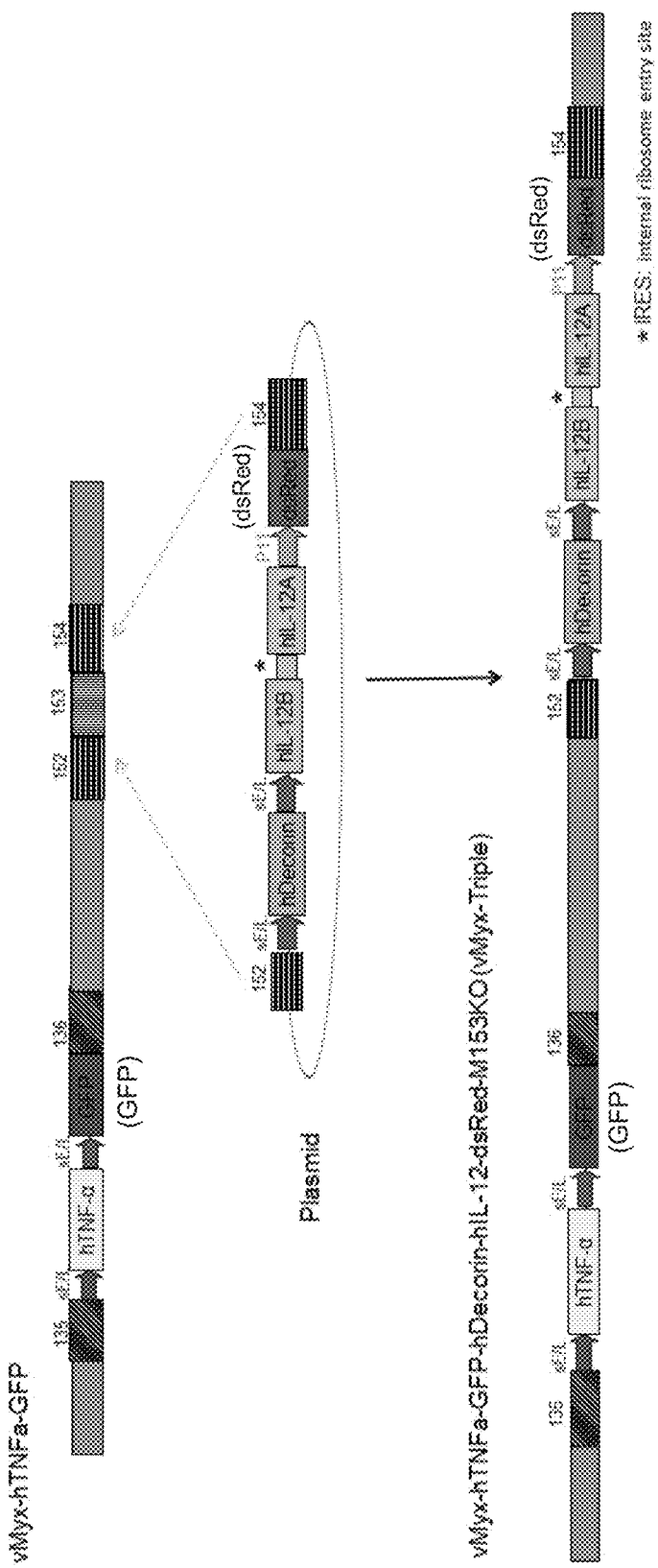
FIG. 1A is a schematic diagram showing construction of recombinant nucleic acids that can be used to generate myxoma viruses (MYXV) disclosed herein. The top image depicts a recombinant nucleic acid that comprises a vMyx-hTNFa-GFP cassette, and an M153 locus. The recombinant nucleic acid can be present in the genome of a MYXV of the disclosure, for example, a vMyx-hTNFa-GFP virus. The middle image shows a recombinant nucleic acid comprising the hDecorin-hIL-12-dsRed cassette with flanking sequences that correspond to sequences that flank the M153 gene in the MYXV genome (M152 and M154). This recombinant nucleic acid can be present in a recombination plasmid that can be introduced into MYXV to generate a modified recombinant virus. The bottom image shows a modified vMyx-Triple recombinant nucleic acid. The recombinant nucleic acid can be present in the genome of a MYXV of the disclosure. For example, the recombination plasmid depicted in the middle image can be introduced into a MYXV (e.g., by infecting RK13 cells with vMyx-hTNFa-GFP virus, and transfecting the cells with the recombination plasmid). Recombination can occur to generate the vMyx-Triple recombinant nucleic acid. Recombinant viruses that comprise the vMyx-Triple recombinant nucleic acid can be identified and purified based on a selection marker, for example, dsRed.

Described herein are oncolytic viruses, specifically oncolytic poxviruses such as oncolytic myxoma viruses. Myxoma viruses can be referred to herein as MYXV or vMyx. In some embodiments, the MYXV is genetically engineered to attenuate an activity or expression level engineered to inactivate, disrupt, or attenuate expression of an M153 gene or protein, for example, genetically engineered to attenuate an activity or expression level of the M153 gene or protein. The modification to the myxoma virus as described herein has unexpectedly improved the oncolytic activity of the MYXV when compared with unmodified MYXV, MYXV that contain an intact wild type M153 gene, or MYXV with modification at another gene locus. In addition to modification at the M153 locus, the MYXV can also include one or more transgenes that encode non-viral molecules, such as a TNFα, IL-12, and/or decorin to further enhance the oncolytic activity, increase an anti-tumor immune response, or decrease adverse side effects of the MYXV.

Some embodiments relate to triple transgene-armed oncolytic viruses such as MYXVs, and methods of their use for treatment of cancers, such as metastatic cancers. Some embodiments include a recombinant MYXV construct that expresses 3 human transgenes: a human cytokine (hTNF) that improves the efficacy of the treatment of cancers that metastasize to the lung or other parts of the body, an hIL-12 that can amplify anti-tumor immune responses, and a human Decorin (hDecorin) that blocks TGF-beta signaling within tumor beds. In some embodiments, the viruses disclosed here have a knockout (e.g., deletion or disruption) of the myxoma virus M153 gene or at least a portion thereof, which in some embodiments also improves the anti-tumor immune responses following therapy with these virus constructs. Some embodiments relate to nucleic acid constructs such as virus triple-transgene constructs that encode the MYXVs. In some embodiments, the transgenes and other modifications to the MYXV improve cancer therapy efficacy.

Definitions

The section headings used herein are for organizational purposes only and are not to be construed as limiting the subject matter described.

The following explanations of terms are provided for the purpose of describing particular embodiments and examples only and is not intended to be limiting.

As used herein, the singular forms "a," "an," and "the" are intended to include the plural forms as well, unless the context clearly indicates otherwise.

As used herein, the term "and/or" refers to and encompasses any and all possible combinations of one or more of the associated listed items, as well as the lack of combinations when interpreted in the alternative ("or").

As used herein, "one or more" or at least one can mean one, two, three, four, five, six, seven, eight, nine, ten or more, up to any number.

An "effective amount" or "therapeutically effective amount" refers to an amount of a compound or composition of this invention that is sufficient to produce a desired effect, which can be a therapeutic and/or beneficial effect.

A "subject in need thereof" or "a subject in need of" is a subject known to have, or is suspected of having a disease, or condition, such as a cancer.

As used herein, the term "inhibiting" or "treating" a disease refers to inhibiting the full development of a disease or condition. "Treatment" refers to a therapeutic intervention that ameliorates a sign or symptom of a disease or pathological condition after it has begun to develop. The term "ameliorating," with reference to a disease or pathological condition, refers to any observable beneficial effect of the treatment. The beneficial effect can be evidenced, for example, by a delayed onset of clinical symptoms of the disease in a susceptible subject, a reduction in severity of some or all clinical symptoms of the disease, a slower progression of the disease, such a metastasis, an improvement in the overall health or well-being of the subject, or by other parameters well known in the art that are specific to the particular disease. A "prophylactic" treatment is a treatment administered to a subject who does not exhibit signs of a disease or exhibits only early signs for the purpose of decreasing the risk of developing pathology, for example metastatic cancer.

MYXV may infect cells that have a deficient innate anti-viral response. Having "a deficient innate anti-viral response" as used herein refers to a cell that, when exposed to a virus or when invaded by a virus, does not induce anti-viral defense mechanisms, which can include inhibition of viral replication, production of interferon, induction of the interferon response pathway, and apoptosis. The term includes a cell, such as a cancer cell, that has a reduced or defective innate anti-viral response upon exposure to or infection by a virus as compared to a normal cell, for example, a non-infected, or non-cancer cell. This includes a cell that is non-responsive to interferon and a cell that has a reduced or defective apoptotic response or induction of the apoptotic pathway. The deficiency may be due to various causes, including infection, genetic defect, or environmental stress. It will however be understood that when the deficiency is caused by a pre-existing infection, superinfection by MYXV may be excluded and a skilled person can readily identify such instances. A skilled person can readily determine without undue experimentation whether any given cell type has a deficient innate anti-viral response and therefore is susceptible to infection by MYXV. Thus, in certain embodiments, the MYXV is capable of infecting cells that have a deficient innate anti-viral response. In certain embodiments, the cells are non-responsive to interferon. In specific embodiments, the cell is a mammalian cancer cell. In certain embodiments, the cell is a human cancer cell including a human solid tumor cell. In certain embodiments, the cells that have a deficient innate anti-viral response comprise cancer cells.

Engineered Myxoma Viruses

Disclosed herein, in certain embodiments, are myxoma viruses (MYXVs). The MYXV may comprise a wild-type strain of MYXV or it may comprise a genetically modified strain of MYXV. In some embodiments, the MYXV comprises a *Lausanne* strain. In some embodiments, the Lausanne strain of MYXV comprises GenBank Accession Number AF170726.2, published on Jul. 11, 2019.

In some instances, the MYXV comprises a South American MYXV strain that circulates in *Sylvilagus brasiliensis*. In some instances, the MYXV comprises a Californian MYXV strain that circulates in *Sylvilagus bachmani*. In some instances, the MYXV comprises 6918, an attenuated Spanish field strain that comprises modifications in genes M009L, M036L, M135R, and M148R (for example, GenBank Accession number EU552530, published on Jul. 11, 2019). In some instances, the MYXV comprises 6918VP60-T2 (GenBank Accession Number EU552531, published on Jul. 11, 2019). In some instances, the MYXV comprises a Standard laboratory Strain (SLS). In some embodiments, the MYXV comprises a nucleic acid construct or MYXV genome as described herein.

In some instances, the MYXV comprises at least 70%, at least 75%, at least 80%, at least 85%, at least 90%, at least 95%, at least 96%, at least 97%, at least 98%, or at least 99%, such as between 95% and 98%, 95% and 99%, including 90%, 91%, 92%, 93%, 94%, 95%, 96%, 97%, 98%, 99% nucleic acid sequence identity to a sequence disclosed in Cameron, et al., "The complete DNA sequence of Myxoma Virus," Virology 264: 298-318 (1999), which is incorporated by reference for such disclosure. In some cases, the MYXV comprises the sequence disclosed in Cameron, et al., "The complete DNA sequence of Myxoma Virus," Virology 264: 298-318 (1999).

In some embodiments, the MYXVs are engineered to inactivate or attenuate an activity or expression level of a viral gene or protein. In some embodiments, the viral gene or protein is M153. In some embodiments, the inactivated or attenuated activity or expression level of the viral gene or protein results in the MYXV exhibiting enhanced anti-cancer activity in relation to a wild-type MYXV, or in relation to a MYXV not having the inactivated or attenuated activity or expression level of the viral gene or protein, for example, a MYXV that comprises a wild type M153 gene and/or expresses a wild type M153 protein. In some embodiments, the MYXV is engineered to inactivate or attenuate an activity or expression level of more than one viral gene or protein.

In some embodiments, the MYXV comprises a nucleic acid that encodes a non-viral molecule, for example, a transgene that encodes a cytokine. In some embodiments, the MYXV includes a transgene such as a transgene described herein. In some embodiments, the transgene encodes a tumor necrosis factor (TNF, e.g., TNFα), an interleukin-12 (IL-12), or a decorin. In some embodiments, the MYXV includes one, two, three, or more transgenes. In some embodiments, one or more transgenes are knocked in to a MYXV genome. In some embodiments, a transgene disrupts a gene in the MYXV genome, for example, a transgene inserted within or replaces part of the gene in the MYXV genome, thereby disrupting expression of the gene and/or the protein it encodes. Such a disruption can be referred to as a knockout (KO).

The MYXV may be modified to produce any non-viral molecule (e.g., modified to carry any transgene) that enhances the anticancer effect of the MYXV. Such a non-viral molecule can be involved in triggering apoptosis, or in targeting the infected cell for immune destruction, such as a non-viral molecule that stimulates a response to interferon (e.g., repairs a lack of response to interferon), or that results in the expression of a cell surface marker that stimulates an antibody response, such as a pathogen-associated molecular pattern, for example, a bacterial cell surface antigen. The MYXV can also be modified to produce a non-viral molecule involved in shutting off the neoplastic or cancer cell's proliferation and growth, thereby preventing the cells from dividing. In some embodiments, the MYXV is modified to produce therapeutic non-viral molecules, such as molecules involved in the synthesis of chemotherapeutic agents, or it can be modified to have increased replication levels in cells of the particular species from which the cells to be inhibited or killed are derived, for example, human cells.

In some embodiments, the MYXV includes a recombinant construct that encodes or expresses one, two, or three separate non-viral molecules, for example, human transgenes (e.g., human TNF, human Decorin and human IL-12). In some embodiments, the recombinant construct further encodes or expresses one or more reporter tags, for example, fluorescent proteins such as eGFP and dsRed.

In some embodiments, the MYXV is genetically engineered to attenuate an activity or expression level of its M153 gene or protein, for example, comprises a disruption of the viral M153 gene (M153-knockout: M153KO). In some embodiments, attenuating the activity or expression level of M153 improves the MHC-dependent anti-tumor immune responses to virus-infected cancer cells. In some embodiments, the MYXVs comprise oncolytic viruses for use in treating cancer. Some embodiments combine a M153KO backbone with the immune-enhancing properties of transgenes disclosed herein to enhance the oncolytic properties of the MYXV.

In some embodiments, the MYXV encodes a TNF (e.g., TNFα) transgene, an IL-12 transgene, a decorin transgene, or any combination of two or more of those. In some embodiments, the MYXV includes a TNF (e.g., TNFα) transgene, an IL-12 transgene, and a decorin transgene. In some such embodiments, upon administration of such an MYXV to a subject, the TNF activates and jump-starts the innate and acquired arms of the anti-tumor immune system and promotes cancer cell death in a by-stander paracrine-like manner. In some embodiments, the IL-12 amplifies the resulting anti-cancer innate and adaptive immune responses. In some embodiments, the decorin interrupts local immunosuppressive actions mediated by TGF-β, thus enhancing the actions of both TNF and IL-12 and promoting the anti-cancer immune response. In some embodiments, the synergistic actions of the three transgenes plus the effects of MYXV in the tumor microenvironment (TME) increase the immunotherapeutic potential of oncolytic MYXV vectors. In some embodiments, the addition of the human transgenes that encode non-viral molecules (hTNF, hIL-12, and/or hDecorin) to the MYXV genome improves the MYXV's capacity to trigger robust anti-tumor immune responses in the tumor microenvironment (TME).

In some embodiments, the MYXV is modified to enhance the ease of detection of infection state. For example, the MYXV may be genetically modified to express a marker that can be readily detected by phase contrast microscopy, fluorescence microscopy or by radioimaging. The marker can be an expressed fluorescent protein or an expressed enzyme that is involved in a colorimetric or radiolabeling reaction. In some embodiments, the marker includes a gene product that interrupts or inhibits a particular function of the cells being tested.

In some embodiments, the engineered MYXV comprises a fluorescent protein. Exemplary fluorescent proteins include blue/UV proteins such as TagBFP, Azurite, Sirus, or Sapphire; cyan proteins such as ECFP, cerulean, or mTurquoise; green proteins such as green fluorescent protein (GFP), Emerald, mUKG, mWasabi, or Clover; yellow proteins such as EYFP, citrine, venus, or SYFP2; orange proteins such as monomeric Kusabira-Orange, mKO2, or mOrange; red proteins such as dsRed, mRaspberrym mCherry, mStrawberry, mTangerine, tdTomato, mApple, or mRuby; photoactivatible proteins such as PA-GFP, PAmCherryl, or PATagRFP; and photoswitchable proteins such as Dropna. In some embodiments, the MYXV includes more than one fluorescent protein. In some embodiments the engineered MYXV does not encode a fluorescent protein.

In some embodiments, the MYXV comprises a vMyx-hTNFa-GFP-hDecorin-hIL-12-dsRed-M153KO (vMyx-Triple or vMyx-Triple-red) construct, and is a vMyx-Triple virus. In some embodiments, the MYXV comprises a vMyx-hTNFa-GFP-hDecorin-hIL-12-M153KO (vMyx-Triple-white) construct, and is a vMyx-Triple-white virus.

In some embodiments, the MYXV comprises a modification at or adjacent to one or more genes associated with rabbit cell tropism. In some instances, the one or more genes associated with rabbit cell tropism comprises M11L, M063, M135R, M136R, M-T2, M-T4, M-T5, or M-T7. In some instances, the one or more genes associated with rabbit cell tropism comprise M135R, M136R, or a combination thereof.

The MYXV may be prepared using standard techniques known in the art. For example, the virus may be prepared by infecting cultured rabbit cells, or immortalized permissive human or primate cells, with the MYXV strain that is to be used, allowing the infection to progress such that the virus replicates in the cultured cells and can be released by standard methods known in the art for disrupting the cell surface and thereby releasing the virus particles for harvesting. Once harvested, the virus titer may be determined by infecting a confluent lawn of rabbit cells and performing a plaque assay.

M153 Modification

The M153 gene product is an E3-Ubiquitin ligase that may participate in the down regulation of diverse cellular receptors and proteins, for example, degradation of MHC Class I and CD4 in human cells. In some embodiments, a MYXV of the disclosure has an attenuated activity and/or expression level of M153 protein. In some embodiments, an attenuated activity and/or expression level of M153 protein can enhance presentation of immune epitopes, for example, MHC-dependent presentation of viral and/or cancer immune peptides. Enhanced presentation of immune epitopes by infected cancer cells can elicit stronger immune responses, including anti-cancer T cell responses, such as anti-cancer CD8+ T cell responses. In some embodiments, an attenuated activity and/or expression level of M153 protein increases direct antigen presentation from M153KO virus-infected tumor cells by MHC-I, and enhances immune activation mediated by the MYXV.

In some embodiments, the MYXV comprises a modification of an M153 gene. In some instances, the modification is a mutation that attenuates an activity or expression level of a protein encoded by the M153 gene (e.g., impairs the function of the protein encoded by the M153 gene).

In some instances, the mutation is a deletion, for example, a deletion that attenuates an activity or expression level of a protein encoded by the M153 gene. In some embodiments, the mutation is a deletion of at least about 1%, at least about 5%, at least about 10%, at least about 20%, at least about 30%, at least about 40%, at least about 50%, at least about 60%, at least about 70%, at least about 80%, at least about 90%, at least about 95%, at least about 97%, or at least about 99%, of the nucleic acid sequence of the M153 gene. In some embodiments, the mutation is a deletion of the entire M153 gene. In some cases, the modification is a partial deletion, for example, a deletion of about 10%, about 20%, about 30%, about 40%, about 50%, about 60%, about 70%, about 80%, about 90%, or about 95% of the nucleic acid sequence of the M153 gene. In some embodiments, the deletion is a deletion of at least 1, at least 2, at least 3, at least 4, at least 5, at least 7, at least 10, at least 20, at least 30, at least 40, at least 50, at least 60, at least 70, at least 100, at least 200, or at least 300 nucleic acids. In some embodiments, the deletion disrupts a promoter (e.g., a promoter that drives expression of M153 in a wild type MYXV). In some embodiments, the deletion introduces a stop codon into the M153 gene sequence, for example, a premature stop codon that prevents expression of a full length M153 transcript and/or protein.

In some instances, the mutation is an insertion, for example, an insertion that attenuates an activity or expression level of a protein encoded by the M153 gene. In some embodiments, the insertion comprises a transgene that encodes a non-viral molecule, for example, a transgene that encodes TNF, decorin, IL-12, or a combination thereof. In some embodiments, the insertion comprises two transgenes. In some embodiments, the insertion comprises three transgenes. The transgene(s) can disrupt (e.g., interrupt) the viral M153 gene and attenuate an activity or expression level of a M153 transcript and/or protein. In some embodiments, the insertion comprises a transgene that encodes TNF. In some embodiments, the insertion comprises a transgene that encodes IL-12. In some embodiments, the insertion comprises a transgene that encodes decorin. In some embodiments, the insertion comprises a transgene that encodes TNF and a transgene that encodes IL-12. In some embodiments, the insertion comprises a transgene that encodes TNF and a transgene that encodes decorin. In some embodiments, the insertion comprises a transgene that encodes IL-12 and a transgene that encodes decorin. In some embodiments, the insertion comprises a transgene that encodes TNF, a transgene that encodes IL-12, and a transgene that encodes decorin. In some embodiments, the insertion comprises one or more promoters. In some embodiments, the insertion disrupts a promoter (e.g., a promoter that drives expression of M153 in a wild type MYXV). In some embodiments, combining M153 gene disruption with transgene expression improves the anti-tumor properties of the resulting recombinant virus.

In some embodiments, the insertion is an insertion of at least 1, at least 2, at least 3, at least 4, at least 5, at least 7, at least 10, at least 20, at least 30, at least 40, at least 50, at least 60, at least 70, at least 100, at least 200, at least 300, at least 400, at least 500, at least 600, at least 700, at least 800, at least 900, at least 1000, at least 1500, or at least 2000 nucleic acids.

In some embodiments, the insertion introduces a stop codon into the M153 gene sequence, for example, a premature stop codon that prevents expression of a full length M153 transcript and/or protein. In some embodiments, the insertion alters the reading frame of the M153 gene sequence, thereby disrupting expression of the M153 transcript and/or protein.

In some instances, the mutation is a substitution, for example, a substitution that attenuates an activity or expression level of a protein encoded by the M153 gene. In some embodiments, at least 1, at least 2, at least 3, at least 4, at least 5, at least 7, at least 10, at least 20, at least 30 nucleic acids are substituted. In some embodiments, the substitution introduces a stop codon into the M153 gene sequence, for example, a premature stop codon that prevents expression of a full length M153 transcript and/or protein. In some embodiments, the substitution disrupts a promoter (e.g., a promoter that drives expression of M153 in a wild type MYXV).

In some embodiments, a modification or mutation disclosed herein attenuates the activity level of the M153 gene and/or protein by at least about 10%, at least about 20%, at least about 30%, at least about 40%, at least about 50%, at least about 60%, at least about 70%, at least about 80%, at least about 90%, at least about 95%, at least about 97%, or at least about 99% relative to a wild type MYXV, or a MYXV that encodes a functional wild type M153.

In some embodiments, a modification or mutation disclosed herein attenuates the expression level of the M153 gene and/or protein by at least about 10%, at least about 20%, at least about 30%, at least about 40%, at least about 50%, at least about 60%, at least about 70%, at least about 80%, at least about 90%, at least about 95%, at least about 97%, or at least about 99% relative to a wild type MYXV, or a MYXV that encodes a functional wild type M153.

In some embodiments, a MYXV disclosed herein has an activity level of the M153 protein that is attenuated by at least about 10%, at least about 20%, at least about 30%, at least about 40%, at least about 50%, at least about 60%, at least about 70%, at least about 80%, at least about 90%, at least about 95%, at least about 97%, or at least about 99% relative to a wild type MYXV, or a MYXV that encodes a functional wild type M153.

In some embodiments, a MYXV disclosed herein has an expression level of the M153 gene and/or protein that is attenuated by at least about 10%, at least about 20%, at least about 30%, at least about 40%, at least about 50%, at least about 60%, at least about 70%, at least about 80%, at least about 90%, at least about 95%, at least about 97%, or at least about 99% relative to a wild type MYXV, or a MYXV that encodes a functional wild type M153.

TNF

In some embodiments, the MYXV comprises (e.g., encodes) a non-viral molecule, for example, comprises a transgene that encodes tumor necrosis factor (TNF) protein. In some embodiments, the TNF protein is a TNFα protein. In some embodiments, the TNFα protein is a human TNFα protein. In some embodiments, the TNFα protein is soluble. In some embodiments, the TNFα protein is membrane- or surface-bound. In some embodiments, the TNFα protein enhances the anti-cancer activity of the MYXV by activating anti-tumor immune cells or inducing cancer cell death.

In some embodiments, the TNFα is encoded by a gene that replaces or is adjacent to an M135R gene of the MYXV genome. In some embodiments, the TNFα gene is inserted between an M135R gene and an M136R gene of the MYXV genome. In some embodiments, the TNFα gene is inserted in the intergenic region between an M135R gene and an M136R gene of the MYXV genome. In some embodiments, the TNFα is encoded by a gene that replaces or disrupts an M153 gene of the MYXV genome. In some embodiments, the TNFα gene replaces or disrupts an M153 gene of the MYXV genome.

In some embodiments, expression of the TNFα gene is driven by a promoter such as a poxvirus synthetic early/late (sE/L) promoter. In some embodiments, expression of the TNFα gene is driven by an internal ribosome entry site (IRES). TNF is a cytokine that is part of the innate inflammatory immune response. In some embodiments, TNF participates in amplifying the acquired (e.g., adaptive) immune responses. TNF can be expressed as a cell surface immune ligand and it can also be secreted as a cleaved soluble trimeric cytokine when produced in specific cells that express the converting proteolytic enzymes (such as TACE) that catalyze cleavage and release of the soluble ligand, for example that are expressed at high levels in cells of the myeloid lineage. One TNF effector pathway is the induction of cellular death through the TNF Receptor-1 (TNFR1) pathway. In some embodiments, induction of the TNFR1 pathway by TNF leads to apoptosis or necroptosis. In some embodiments, TNF activates the innate and adaptive immune responses, for example, by activating anti-tumor CD8+ T cells and NK cells.

Despite the early hope that systemic administration of soluble TNF may function in humans as a potent anti-tumor drug, some clinical trials showed that the secreted cytokine caused severe systemic toxicities in patients treated systemically with the soluble ligand. Additionally, the systemic TNF treatment did not induce the dramatic anti-tumor effects in patients that was reported preclinically. A virally derived expression of TNF, e.g., the cell surface membrane form of TNF, may improve local cancer cell death by eliciting a greater degree of bystander cell killing in the tumor microenvironment, and also stimulate various classes of immune cells residing within the same tumor beds, while minimizing systemic TNF-mediated adverse toxic effects.

In some instances, the TNF protein comprises at least 90%, at least 95%, at least 96%, at least 97%, at least 98%, or at least 99% sequence identity to the sequence illustrated in UniProtKB-P01375, published on Jul. 3, 2019 (Entry version 247). In some instances, the TNF protein comprises between 95% and 98%, or 95% and 99% sequence identity to the sequence illustrated in UniProtKB-P01375, published on Jul. 3, 2019 (Entry version 247). In some instances, the TNF protein comprises about 90%, about 91%, about 92%, about 93%, about 94%, about 95%, about 96%, about 97%, about 98%, or about 99% sequence identity to the sequence illustrated in UniProtKB-P01375, published on Jul. 3, 2019 (Entry version 247). In some embodiments, the TNF protein comprises the sequence illustrated in UniProtKB-P01375, published on Jul. 3, 2019 (Entry version 247).

In some instances, the TNF protein comprises at least 90%, at least 95%, at least 96%, at least 97%, at least 98%, or at least 99% sequence identity to residues 77-233 of UniProtKB-P01375. In some instances, the TNF protein comprises between 95% and 98%, or 95% and 99% sequence identity to residues 77-233 of UniProtKB-P01375. In some instances, the TNF protein comprises about 90%, about 91%, about 92%, about 93%, about 94%, about 95%, about 96%, about 97%, about 98%, or about 99% sequence identity to residues 77-233 of UniProtKB-P01375. In some embodiments, the TNF protein comprises residues 77-233 of UniProtKB-P01375.

In some instances, the TNF protein is encoded by a gene comprising at least 90%, at least 95%, at least 96%, at least 97%, at least 98%, or at least 99% sequence identity to SEQ ID NO: 12 or SEQ ID NO: 24. In some instances, the TNF protein is encoded by a gene comprising between 95% and 98%, or 95% and 99% sequence identity SEQ ID NO: 12 or SEQ ID NO: 24. In some instances, the TNF protein is encoded by a gene comprising about 90%, about 91%, about 92%, about 93%, about 94%, about 95%, about 96%, about 97%, about 98%, or about 99% sequence identity to SEQ ID NO: 12 or SEQ ID NO: 24. In some embodiments, the TNF protein is encoded by a gene comprising or consisting of SEQ ID NO: 12 or SEQ ID NO: 24. In some embodiments, the TNF is encoded by a gene comprising the sequence of SEQ ID NO: 12 or SEQ ID NO: 24. In some embodiments, the gene encoding the TNF comprises a sequence that is 70%, 75%, 80%, 85%, 90%, 91%, 92%, 93%, 94%, 95%, 96%, 97%, 98%, 99%, or 100%, or a range of percentages defined by any two of the aforementioned percentages, identical to that of SEQ ID NO: 12 or SEQ ID NO: 24.

In some instances, the TNF protein comprises at least 90%, at least 95%, at least 96%, at least 97%, at least 98%, or at least 99% sequence identity to SEQ ID NO: 31 or residues 77-233 of SEQ ID NO: 31. In some instances, the TNF protein comprises between 95% and 98%, or 95% and 99% sequence identity to SEQ ID NO: 31 or residues 77-233 of SEQ ID NO: 31. In some instances, the TNF protein comprises about 90%, about 91%, about 92%, about 93%, about 94%, about 95%, about 96%, about 97%, about 98%, or about 99% sequence identity to SEQ ID NO: 31 or residues 77-233 of SEQ ID NO: 31. In some embodiments, the TNF protein comprises SEQ ID NO: 31 or residues 77-233 of SEQ ID NO: 31.

IL-12

In some embodiments, the MYXV comprises (e.g., encodes) a non-viral molecule, for example, comprises a transgene that encodes interleukin-12 (IL-12) protein. In some embodiments, the IL-12 protein is a human IL-12 protein. In some embodiments, the IL-12 protein is soluble. In some embodiments, the IL-12 protein is membrane- or surface-bound. In some embodiments, the IL-12 protein further enhances the anti-cancer activity of the MYXV by promoting immune cell differentiation or eliciting immune cell cytotoxicity.

In some embodiments, IL-12 comprises an IL12α subunit (p35 subunit). In some embodiments, the IL-12α subunit is encoded by an IL-12α gene. In some embodiments, the IL-12α gene is a human IL-12α gene. In some embodiments, the IL-12α gene is driven by an IRES. In some embodiments, the IL-12α gene is driven by a promoter such as an sE/L promoter. In some embodiments, IL-12α gene replaces or disrupts the M153 gene. In some embodiments, IL-12α gene is inserted in the intergenic region between an M135R gene and an M136R gene of the MYXV genome.

In some embodiments, IL-12 comprises an IL12β (p40) subunit. In some embodiments, the IL-12β subunit is encoded by an IL-12β gene. In some embodiment, the IL-12β gene is a human IL-12β gene. In some embodiments, the IL-12β gene is driven by an IRES. In some embodiments, the IL-12β gene is driven by a promoter such as an sE/L promoter. In some embodiments, IL-12β gene replaces or disrupts an MYXV M153 gene. In some embodiments, IL-12β gene is inserted in the intergenic region between an M135R gene and an M136R gene of the MYXV genome.

In some embodiments, IL-12 comprises an IL12α subunit and an IL-12β subunit. In some embodiments the IL12α subunit and the IL-12β subunit are covalently linked. In some embodiments the IL12α subunit and the IL-12β subunit are not covalently linked. In some embodiments the IL12α subunit and the IL-12β subunit are expressed as one transcript. In some embodiments the IL12α subunit and the IL-12β subunit are expressed as one polypeptide, for example, with a peptide linker joining the two subunits. A linker sequence can be, for example, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, or 50 amino acid residues in length. A linker can be at least 1, at least 2, at least 3, at least 4, at least 5, at least 6, at least 7, at least 8, at least 9, or at least 10 amino acid residues in length. A linker can be at most 4, at most 5, at most 6, at most 7, at most 8, at most 9, at most 10, at most 15, at most 20, at most 25, at most 30, at most 40, or at most 50 amino acid residues in length. A flexible linker can have a sequence containing stretches of glycine and serine residues. The small size of the glycine and serine residues provides flexibility and allows for mobility of the connected functional domains. The incorporation of serine or threonine can maintain the stability of the linker in aqueous solutions by forming hydrogen bonds with the water molecules, thereby reducing unfavorable interactions between the linker and protein moieties. Flexible linkers can also contain additional amino acids such as threonine and alanine to maintain flexibility, as well as polar amino acids such as lysine and glutamine to improve solubility. A rigid linker can have, for example, an alpha helix-structure. An alpha-helical rigid linker can act as a spacer between protein domains. A linker can comprise any of the sequences of SEQ ID NOs: 33-43 or repeats thereof. SEQ ID NOs: 33-38 and 43 provide examples flexible linker sequences. SEQ ID NOs: 39-42 provide examples of rigid linker sequences.

In some embodiments, the MYXV expresses a relatively low level of IL-12. Relatively lower expression of IL-12 can be achieved, for example, by use of an IRES sequence between the sequences that encode the IL-12 subunits. In some embodiments, the MYXV expresses a relatively high level of IL-12. Relatively higher expression of IL-12 can be achieved, for example, by use of a suitable linker that joins the subunits of IL-12 in a single polypeptide, for example, an elastin linker, such as the linker of SEQ ID NO: 43.

In some embodiments, a level of IL-12 expression can be as determined by the assay of example 6. For example, vero cells can be infected with a MYXV of the disclosure at an MOI of 1, supernatant can be harvested at 24 hours post-infection, and the amount of IL-12 can be measured by ELISA. In some embodiments, a low level of IL-12 expression can be less than 50, less than 40, less than 30, less than 20, less than 10, or less than 5 ng/mL of IL-12 as determined by the assay of example 6. In some embodiments, a high level of IL-12 expression can be more than 20, more than 30, more than 40, more than 50, more than 60, more than 70, more than 80, more than 90, more than 100, or more than 150 ng/mL of IL-12 as determined by the assay of example 6. In some embodiments, a high level of IL-12 expression can be more than 20 ng/mL of IL-12, and a low level of IL-12 expression can be less than 20 ng/mL of IL-12.

In some embodiments, one or both of the IL-12 subunits can be truncated. An example of an IL-12 with a truncated subunit is provided in SEQ ID NO: 50, which comprises mouse IL-12 B (SEQ ID NO: 51), an elastin linker (SEQ ID NO: 43), and a truncated mouse IL-12 A (SEQ ID NO: 52).

IL-12 is a cytokine. In some embodiments, IL-12 promotes T helper type 1 (Th1) differentiation and enhances the cytotoxicity of natural killer (NK) cells and cytotoxic T lymphocytes (CTLs). In some embodiments, the actions of this IL-12 create an improved interconnection between the elements of innate and adaptive immunity to promote an anti-cancer immune response. In some embodiments, due to this bridging the innate and adaptive immunity, IL-12 enhances the anti-tumor effects of the MYXV. In some embodiments, IL-112 potently stimulates production of IFN-γ (a cytokine that coordinates mechanisms of anticancer defense), thereby enhancing the anti-tumor effects of the MYXV.

Clinical trials of systemic delivery of recombinant IL-12 cytokine therapy have not induced satisfactory outcomes in cancer patients due to toxicity events, the transient nature of systemically administered IL-12, and tumor-induced immunosuppression. Nevertheless, viruses expressing IL-12 locally within the tumor microenvironment (TME) may result in potent antitumor efficacy. In some embodiments, expression of IL-12 from an oncolytic virus that is restricted to tumor beds, such that the transgenes are expressed locally within the TME, reduces the toxic effects associated with the systemic delivery of this cytokine. Thus, in some embodiments, the co-expression of the two subunits of IL-12 improves the anti-tumor immunity induced by armed-MYXV against different type of cancers.

In some instances, the IL12α subunit comprises at least 90%, at least 95%, at least 96%, at least 97%, at least 98%, or at least 99% sequence identity to SEQ ID NO: 28, residues 35-253 of SEQ ID NO: 28, or residues 57-253 of SEQ ID NO: 28. In some instances, the IL12α subunit comprises between 95% and 98%, or 95% and 99% sequence identity to SEQ ID NO: 28, residues 35-253 of SEQ ID NO: 28, or residues 57-253 of SEQ ID NO: 28. In some instances, the IL12α subunit comprises about 90%, about 91%, about 92%, about 93%, about 94%, about 95%, about 96%, about 97%, about 98%, or about 99% sequence identity to SEQ ID NO: 28, residues 35-253 of SEQ ID NO: 28, or residues 57-253 of SEQ ID NO: 28. In some embodiments, the IL12α subunit comprises SEQ ID NO: 28, residues 35-253 of SEQ ID NO: 28, or residues 57-253 of SEQ ID NO: 28.

In some instances, the IL-12β subunit comprises at least 90%, at least 95%, at least 96%, at least 97%, at least 98%, or at least 99% sequence identity to SEQ ID NO: 29 or residues 23-328 of SEQ ID NO: 29. In some instances, the IL-12β subunit comprises between 95% and 98%, or 95% and 99% sequence identity to SEQ ID NO: 29 or residues 23-328 of SEQ ID NO: 29. In some instances, the IL-12β subunit comprises about 90%, about 91%, about 92%, about 93%, about 94%, about 95%, about 96%, about 97%, about 98%, or about 99% sequence identity to SEQ ID NO: 29 or residues 23-328 of SEQ ID NO: 29. In some embodiments, the IL-12β subunit comprises SEQ ID NO: 29 or residues 23-328 of SEQ ID NO: 29.

Decorin

In some embodiments, the MYXV comprises (e.g., encodes) a non-viral molecule, for example, comprises a transgene that encodes decorin. In some embodiments, the decorin protein is a human decorin protein. In some embodiments, the decorin protein is soluble. In some embodiments, the decorin protein is membrane- or surface-bound. In some embodiments, the decorin protein enhances the anti-cancer activity of the MYXV by blocking or decreasing TGF-β signaling.

In some embodiments, the decorin protein is encoded by a decorin gene. In some embodiments, the decorin gene is a human decorin gene. In some embodiments, the decorin gene is driven by an IRES. In some embodiments, the decorin gene is driven by a promoter such as an sE/L promoter. In some embodiments, the decorin gene replaces or disrupts an M153 gene. In some embodiments, the decorin gene is inserted in the intergenic region between an M135R gene and an M136R gene of the MYXV genome.

Decorin is a member of the extracellular matrix proteoglycans family that exists and functions within stromal tissues and epithelial cells. In some embodiments, decorin affects the biology of different types of cancer by directly or indirectly targeting signaling molecules involved in cell growth, survival, metastasis and/or angiogenesis. In some embodiments, decorin blocks TGF-β-induced signaling. In some embodiments, TGF-β is a cytokine that contributes to immune suppression in some tumor microenvironments (TMEs). In some cases, TGF-β converts effector T-cells, which may otherwise recognize and attack cancer cells, into regulatory (suppressor) T-cells, which instead turn off the innate inflammatory reactions and acquired immune pathways needed to recognize and eliminate the cancer cells. In multiple type of cancers, parts of the TGF-β signaling pathways are mutated, and this cytokine no longer controls at least some of the cell targets. These cancer cells may proliferate and increase their endogenous production of TGF-β, which may act on the surrounding stromal cells, immune cells, endothelial and smooth-muscle, causing local immunosuppression within the cancer tissue and tumor bed angiogenesis, which makes the cancer even more invasive. Hence, in some embodiments, an oncolytic MYXV vector expressing decorin blocks TGF-β directly within the TME and thereby induces a stronger anti-tumor immune response than a MYXV not expressing the decorin.

Additionally, decorin can inhibit tumor cell growth and proliferation. Viral delivery of decorin into various solid tumors may directly counteract tumorigenesis. In some embodiments, decorin is used as an anti-cancer target for at least some types of cancer that are protected by the local over-expression of TGF-β.

In some embodiments, the decorin is encoded by a gene comprising the sequence of SEQ ID NO: 25. In some embodiments, the gene encoding the decorin comprises a sequence that is 70%, 75%, 80%, 85%, 90%, 91%, 92%, 93%, 94%, 95%, 96%, 97%, 98%, 99%, or 100%, or a range of percentages defined by any two of the aforementioned percentages, identical to that of SEQ ID NO: 25. In some instances, the decorin is encoded by a gene comprising at least 90%, at least 95%, at least 96%, at least 97%, at least 98%, or at least 99% sequence identity to SEQ ID NO: 25. In some instances, the decorin is encoded by a gene comprising between 95% and 98%, or 95% and 99% sequence identity to SEQ ID NO: 25. In some instances, the decorin is encoded by a gene comprising about 90%, about 91%, about 92%, about 93%, about 94%, about 95%, about 96%, about 97%, about 98%, or about 99% sequence identity to SEQ ID NO: 25.

In some instances, the decorin protein comprises at least 90%, at least 95%, at least 96%, at least 97%, at least 98%, or at least 99% sequence identity to residues 31-359 of SEQ ID NO: 14, or any one of SEQ ID NOs: 14-19. In some instances, the decorin protein comprises between 95% and 98%, or 95% and 99% sequence identity to residues 31-359 of SEQ ID NO: 14, or any one of SEQ ID NOs: 14-19. In some instances, the decorin protein comprises about 90%, about 91%, about 92%, about 93%, about 94%, about 95%, about 96%, about 97%, about 98%, or about 99% sequence identity to residues 31-359 of SEQ ID NO: 14, or any one of SEQ ID NOs: 14-19. In some embodiments, the decorin protein comprises residues 31-359 of SEQ ID NO: 14, or any one of SEQ ID NOs: 14-19.

Recombinant Nucleic Acids

Disclosed herein, in certain embodiments, are recombinant nucleic acids. Some embodiments relate to a recombinant nucleic acid comprising at least a portion of a MYXV genome. In some embodiments, the recombinant nucleic acid comprises DNA. In some embodiments, the MYXV genome or the portion of the MYXV genome is modified to reduce expression of M153 gene. In some embodiments, the M153 gene is modified to knock out at least a portion of the M153 gene in the MYXV genome.

In some embodiments, the recombinant nucleic acid is engineered to introduce a mutation to the M153 gene. The mutation can comprise, for example, an insertion, deletion, substation, or a combination thereof. In some embodiments, the recombinant nucleic acid comprises a gene knock-in where the M153 gene is disrupted.

In some embodiments, the recombinant nucleic acid comprises a nucleic acid that encodes a non-viral molecule. In some embodiments, the recombinant nucleic acid comprises 1, 2, 3, 4, 5, 6, 7, 8, 9, 10, or more nucleic acid that encode non-viral molecule, for example, transgenes that encode proteins.

In some embodiments, the recombinant nucleic acid comprises a nucleic acid that encodes tumor necrosis factor alpha (TNFα). In some embodiments, the TNFα is a human TNFα. In some embodiments, the nucleic acid that encodes the TNFα replaces or is adjacent to an M135R gene of the MYXV genome. In some embodiments, the nucleic acid that encodes the TNFα is inserted between an M135R gene and an M136R gene of the MYXV genome. In some embodiments, expression of TNFα is driven by a poxvirus synthetic early/late (sE/L) promoter. In some embodiments, the nucleic acid that encodes the TNFα replaces or is adjacent to an M153 gene of the MYXV genome.

In some embodiments, the recombinant nucleic acid comprises a nucleic acid that encodes an interleukin-12 subunit alpha (IL-12α). In some embodiments, the IL-12α is a human IL-12α. In some embodiments, expression of the IL-12α is driven by an internal ribosome entry site (IRES). In some embodiments, the nucleic acid that encodes IL-12α disrupts expression of an M153 gene of the MYXV genome.

In some embodiments, the recombinant nucleic acid comprises a nucleic acid that encodes an interleukin-12 subunit beta (IL-12β). In some embodiments, the IL-12β is a human IL-12β gene. In some embodiments, expression of the IL-12β is driven by an sE/L promoter. In some embodiments, the nucleic acid that encodes IL-12β disrupts expression of an M153 gene of the MYXV genome. In some embodiments, the nucleic acid that encodes IL-12β and the nucleic acid that encodes IL-12α both disrupt expression of an M153 gene of the MYXV genome.

In some embodiments, the recombinant nucleic acid comprises a nucleic acid that encodes decorin. In some embodiments, the decorin is a human decorin. In some embodiments, expression of the decorin is driven by an sE/L promoter. In some embodiments, the recombinant nucleic acid comprises a nucleic acid that encodes decorin disrupts expression of an M153 gene of the MYXV genome.

In some embodiments, the recombinant nucleic acid comprises a nucleic acid that encodes a reporter tag, for example, a fluorescent protein. In some embodiments, the reporter tag comprises a green fluorescent protein (GFP). In some embodiments, expression of the reporter tag is driven by an sE/L promoter. In some embodiments, the recombinant nucleic acid further comprises a nucleic acid that encodes a second reporter tag. In some embodiments, the second reporter tag comprises a red fluorescent protein (RFP), e.g., dsRed. In some embodiments, expression of the second reporter tag is driven by a poxvirus P11 late promoter. In some embodiments, the nucleic acid that encodes the second reporter tag disrupts expression of an M153 gene of the MYXV genome.

In some embodiments, the recombinant nucleic acid comprises a vMyx-hTNFa cassette, optionally comprising GFP. In some embodiments, the recombinant nucleic acid comprises an hDecorin-hIL-12 cassette, optionally comprising dsRed. In some embodiments, the recombinant nucleic acid comprises or consists of a vMyx-hTNFa-hDecorin-hIL-12-M153KO (vMyx-Triple) cassette, optionally comprising GFP and/or dsRed.

Composition and Administration

Disclosed herein, in certain embodiments, are compositions comprising a MYXV as described herein. In some embodiments, the composition comprises a pharmaceutical composition. In some embodiments, the composition comprises a pharmaceutically acceptable carrier or excipient.

In some embodiments, the pharmaceutically acceptable carrier comprises an injectable fluid such as water, physiological saline, balanced salt solutions, aqueous dextrose, glycerol or the like. In some embodiments, the composition comprises a solid composition such as a powder, pill, tablet, or capsule. In some embodiments such as those including solid compositions, the pharmaceutically acceptable carrier comprises mannitol, lactose, starch, or magnesium stearate. In some embodiments, the pharmaceutically acceptable carrier comprises a biologically neutral carrier. In some embodiments, the composition comprises wetting or emulsifying agents, preservatives, and pH buffering agents and the like, for example sodium acetate or sorbitan monolaurate.

In some embodiments, the identity or proportion of the pharmaceutically acceptable carrier or excipient is determined based on a route of administration, compatibility with a live virus, or standard pharmaceutical practice. In some embodiments, the pharmaceutical composition is formulated with components that do not significantly impair the biological properties of the MYXV. The pharmaceutical composition can be prepared by known methods for the preparation of pharmaceutically acceptable compositions suitable for administration to subjects, such that an effective quantity of the active substance or substances is combined in a mixture with a pharmaceutically acceptable vehicle. In some embodiments, the composition includes solutions of the MYXV in association with one or more pharmaceutically acceptable excipient, vehicles, or diluents, and contained in buffer solutions with a suitable pH and iso-osmotic with physiological fluids.

In some embodiments, the pharmaceutical composition is formulated for administration to a subject. The pharmaceutical composition may be administered to a subject in a variety of forms depending on the selected route of administration, as will be understood by those skilled in the art. In some instances, the pharmaceutical composition is administered systemically, or formulated for systemic administration. In some embodiments, the pharmaceutical composition is administered locally, or formulated for local administration.

In some embodiments, the pharmaceutical composition is administered parenterally, or formulated for parenteral administration. Examples of parenteral administration include intravenous, intratumoral, intraperitoneal, subcutaneous, intramuscular, transepithelial, nasal, intrapulmonary, intrathecal, rectal and topical modes of administration. Parenteral administration may be by continuous infusion over a selected period of time.

In some embodiments, the pharmaceutical composition is administered orally, or formulated for oral administration. The pharmaceutical composition may be administered orally, for example, with an inert diluent or with a carrier, or it may be enclosed in hard or soft shell gelatin capsules, or it may be compressed into tablets. For oral therapeutic administration, the MYXV may be incorporated with an excipient and be used in the form of ingestible tablets, buccal tablets, troches, capsules, elixirs, suspensions, syrups, wafers and the like.

Solutions of MYXV may be prepared in a physiologically suitable buffer. In some embodiments, under ordinary conditions of storage and use, these preparations contain a preservative to prevent the growth of microorganisms, but that will not inactivate the live virus. In some embodiments, a dose of the pharmaceutical composition to be used depends on the particular condition being treated, the severity of the condition, the individual subject parameters including age, physical condition, size and weight, the duration of the treatment, the nature of concurrent therapy (if any), the specific route of administration and other similar factors that are within the knowledge and expertise of the health practitioner. In certain embodiments, the therapeutic virus may be freeze dried for storage at room temperature.

The pharmaceutical compositions may additionally contain additional therapeutic agents, such as additional anticancer agents. In some embodiments, the compositions include a chemotherapeutic agent. The chemotherapeutic agent, for example, may be substantially any agent, which exhibits an oncolytic effect against cancer cells or neoplastic cells of the subject and that does not inhibit or diminish the tumor killing effect of the MYXV. For example, the chemotherapeutic agent may be, without limitation, an anthracycline, an alkylating agent, an alkyl sulfonate, an aziridine, an ethylenimine, a methylmelamine, a nitrogen mustard, a nitrosourea, an antibiotic, an antimetabolite, a folic acid analogue, a purine analogue, a pyrimidine analogue, an enzyme, a podophyllotoxin, a platinum-containing agent or a cytokine. Preferably, the chemotherapeutic agent is one that is known to be effective against the particular cell type that is cancerous or neoplastic. In some cases, the additional therapeutic agent comprises an immune checkpoint modulator.

In some embodiments, the composition comprises peripheral blood mononuclear cells (PBMCs), bone marrow (BM) cells, or a combination thereof treated ex vivo by an MYXV as described herein. In some embodiments, the PBMCs, BM cells, or a combination thereof comprise autologous cells. In some embodiments, the PBMCs, BM cells, or a combination thereof are obtained from an allogeneic donor. In some embodiments, the PBMCs, BM cells, or a combination thereof are obtained from heterologous donors.

Methods of Use

Disclosed herein, in certain embodiments, are methods of inhibiting, alleviating, or preventing a cancer in a subject in need thereof, comprising administering to the subject a composition or pharmaceutical composition as described herein. In certain embodiments, the method includes administering to a subject, such as a human subject, a MYXV as described herein, thereby treating and/or inhibiting the cancer in the subject in need thereof.

Some embodiments include prophylactic treatment with the MYXV. In some embodiments, the subject has, is suspected of having, or is at risk of having the cancer. Some embodiments include selecting the subject suspected of having. Some embodiments include selecting the subject at risk of having the cancer. In some embodiments, the subject has the cancer. In some embodiments, the methods include selecting the subject with the cancer.

In some embodiments, the subject is a human. In some embodiments, the subject is a patient. In some embodiments, the subject is an animal or nonhuman animal. Examples of nonhuman animals include vertebrates such as mammals and non-mammals. Some examples of mammals include nonhuman primates, sheep, dog, cat, horse, cow, and rodents such as mice and rats.

In some embodiments, the cancer is a solid tumor. Examples of solid tumors such as sarcomas and carcinomas include but are not limited to fibrosarcoma, myxosarcoma, liposarcoma, chondrosarcoma, osteosarcoma, osteogenic sarcoma, and other sarcomas, synovioma, mesothelioma, Ewing's sarcoma, leiomyosarcoma, rhabdomyosarcoma, colon carcinoma, lymphoid malignancy, pancreatic cancer, breast cancer, lung cancers, non-small cell lung cancer, ovarian cancer, prostate cancer, hepatocellular carcinoma, squamous cell carcinoma, basal cell carcinoma, adenocarcinoma, sweat gland carcinoma, sebaceous gland carcinoma, papillary carcinoma, papillary adenocarcinomas, medullary carcinoma, bronchogenic carcinoma, renal cell carcinoma, hepatoma, bile duct carcinoma, choriocarcinoma, Wilms' tumor, cervical cancer, testicular tumor, bladder carcinoma, and CNS tumors (such as a glioma, astrocytoma, medulloblastoma, craniopharyogioma, ependymoma, pinealoma, hemangioblastoma, acoustic neuroma, oligodendroglioma, menangioma, melanoma, neuroblastoma and retinoblastoma). In some embodiments, the cancer comprises an osteosarcoma, triple negative breast cancer, or melanoma.

In some embodiments, the cancer has metastasized to a location in the subject. In some embodiments, the location comprises a lung, a brain, a liver and/or a lymph node of the subject.

In some embodiments, the cancer comprises a hematologic cancer such as Hodgkin's lymphoma or non-Hodgkin's lymphoma. In some embodiments, the hematologic cancers include B-cell or T-cell hematologic cancer.

In some embodiments, the composition reduces cancer cell viability, or activates immunogenic cell death in the cancer. In some embodiments, the cancer is inhibited, alleviated, or prevented upon administration of the composition. In some embodiments, the administration improves the subject's survival.

MYXV or the composition comprising the MYXV can be administered to the subject using standard methods of administration. In some embodiments, the virus or the composition comprising the virus is administered systemically (e.g., IV injection). In some embodiments, the virus or the composition comprising the virus is administered by injection at the disease site (e.g., intratumorally). In some embodiments, the virus or the composition comprising the virus is administered orally or parenterally, or by any standard method known in the art. In certain embodiments, the MYXV or the composition comprising the MYXV is administered at a site of a tumor and/or metastasis.

The MYXV can be administered initially in a suitable amount that may be adjusted as required, depending on the clinical response of the subject. The effective amount of virus can be determined empirically and depends on the maximal amount of the MYXV that can be administered safely, and the minimal amount of the virus that produces the desired result.

The concentration of virus to be administered may vary depending on the virulence of the particular strain of MYXV that is to be administered and on the nature of the cells that are being targeted. In one embodiment, a dose of less than about $3 \times 10^{10}$ focus forming units ("ffu"), also called "infectious units", is administered to a human subject, in various embodiments, between about $10^2$ to about $10^9$ pfu, between about $10^2$ to about $10^7$ pfu, between about $10^3$ to about $10^6$ pfu, or between about $10^4$ to about $10^5$ pfu may be administered in a single dose.

In some embodiments, the MYXV is administered at a dose and schedule effective to increase expression of a cytokine by immune cells (e.g., PBMCs) in the subject. The expression of a cytokine by immune cells can be increased, for example, by at least about 10%, at least about 20%, at least about 30%, at least about 40%, at least about 50%, at least about 60%, at least about 70%, at least about 80%, at least about 90%, at least about 2-fold, at least about 5-fold, at least about 10-fold, at least about 50-fold, at least about 100-fold, at least about 1000-fold, or at least about 1000-fold. In some embodiments, the MYXV is administered at a dose and schedule effective to increase expression of two, three, four, five, six, or more cytokines by immune cells in the subject. In some embodiments, the MYXV is administered at a dose and schedule effective to increase expression of at least one, at least two, at least three, at least four, at least five, at least six, or more cytokines by immune cells in the subject. The cytokines can comprise, for example, IFN-γ, IL-2, IL-6, IL-10, IL-12, TNF-α, or any combination thereof. In some embodiments, expression of TNF-α is increased. In some embodiments, expression of IL-12 is increased. In some embodiments, expression of decorin is increased. In some embodiments, expression of IFN-γ is increased.

In some embodiments, the MYXV is administered at a dose and schedule effective to increase expression of a cytokine by cancer cells in the subject. The expression of a cytokine by cancer cells can be increased, for example, by at least about 10%, at least about 20%, at least about 30%, at least about 40%, at least about 50%, at least about 60%, at least about 70%, at least about 80%, at least about 90%, at least about 2-fold, at least about 5-fold, at least about 10-fold, at least about 50-fold, at least about 100-fold, at least about 1000-fold, or at least about 1000-fold. In some embodiments, the MYXV is administered at a dose and schedule effective to increase expression of two, three, four, five, six, or more cytokines by cancer cells in the subject. In some embodiments, the MYXV is administered at a dose and schedule effective to increase expression of at least one, at least two, at least three, at least four, at least five, at least six, or more cytokines by cancer cells in the subject. The cytokines can comprise, for example, IFN-γ, IL-2, IL-6, IL-10, IL-12, TNF-α, or any combination thereof. In some embodiments, expression of TNF-α is increased. In some embodiments, expression of IL-12 is increased. In some embodiments, expression of decorin is increased. In some embodiments, expression of IFN-γ is increased.

In some embodiments, the MYXV is administered at a dose and schedule effective to reduce the volume of a tumor in the subject. The volume of the tumor can be reduced, for example, by at least about 5%, at least about 10%, at least about 20%, at least about 30%, at least about 40%, at least about 50%, at least about 60%, at least about 70%, at least about 80%, or at least about 90%.

In some embodiments, the MYXV is administered at a dose and schedule effective to reduce the rate of tumor or cancer cell growth in the subject. The rate of tumor or cancer cell growth can be reduced, for example, by at least about 5%, at least about 10%, at least about 20%, at least about 30%, at least about 40%, at least about 50%, at least about 60%, at least about 70%, at least about 80%, or at least about 90%.

The MYXV can be administered as a sole therapy or may be administered in combination with other therapies, including chemotherapy, immunotherapy and/or radiation therapy. For example, the MYXV can be administered either prior to or following surgical removal of a primary tumor or prior to, concurrently with or following treatment such as administration of radiotherapy or conventional chemotherapeutic drugs. In some embodiments, the MYXV can be administered at least 1 day, 2 days, 3 days, 4 days, 5 days, 6 days, 7 days, 1.5 weeks, 2 weeks, or 3 weeks before the other therapy. In some embodiments, the MYXV can be administered at least 1 day, 2 days, 3 days, 4 days, 5 days, 6 days, 7 days, 1.5 weeks, 2 weeks, or 3 weeks after the other therapy. In some embodiments, the MYXV can be administered within 1 day, 2 days, 3 days, 4 days, 5 days, 6 days, or 7 days of the other therapy. In some embodiments, the MYXV can be administered concurrently with the other therapy.

Some embodiments further comprise administering to the subject an additional therapeutic agent. In some embodiments, the additional therapeutic agent is an immune checkpoint modulator. In some embodiments, the additional therapeutic agent is administered to the subject before administering the composition. In some embodiments, the additional therapeutic agent is administered to the subject after administering the composition. In some embodiments, the additional therapeutic agent is administered to the subject as a combination with the composition.

In some embodiments, the additional therapeutic agent comprises an immune modulator, for example, an immune checkpoint modulator or inhibitor. Exemplary immune checkpoint modulators include, but are not limited to, PD-L1 inhibitors such as durvalumab (Imfinzi) from AstraZeneca, atezolizumab (MPDL3280A) from Genentech, avelumab from EMD Serono/Pfizer, CX-072 from CytomX Therapeutics, FAZ053 from Novartis Pharmaceuticals, KN035 from 3D Medicine/Alphamab, LY3300054 from Eli Lilly, or M7824 (anti-PD-L1/TGFbeta trap) from EMD Serono; PD-L2 inhibitors such as GlaxoSmithKline's AMP-224 (Amplimmune), and rHIgM12B7; PD-1 inhibitors such as nivolumab (Opdivo) from Bristol-Myers Squibb, pembrolizumab (Keytruda) from Merck, AGEN 2034 from Agenus, BGB-A317 from BeiGene, B1-754091 from Boehringer-Ingelheim Pharmaceuticals, CBT-501 (genolimzumab) from CBT Pharmaceuticals, INCSHR1210 from Incyte, JNJ-63723283 from Janssen Research & Development, MEDI0680 from MedImmune, MGA 012 from MacroGenics, PDR001 from Novartis Pharmaceuticals, PF-06801591 from Pfizer, REGN2810 (SAR439684) from Regeneron Pharmaceuticals/Sanofi, or TSR-042 from TESARO; CTLA-4 inhibitors such as ipilimumab (also known as Yervoy®, MDX-010, BMS-734016 and MDX-101) from Bristol Meyers Squibb, tremelimumab (CP-675, 206, ticilimumab) from Pfizer, or AGEN 1884 from Agenus; LAG3 inhibitors such as BMS-986016 from Bristol-Myers Squibb, IMP701 from Novartis Pharmaceuticals, LAG525 from Novartis Pharmaceuticals, or REGN3767 from Regeneron Pharmaceuticals; B7-H3 inhibitors such as enoblituzumab (MGA271) from MacroGenics; KIR inhibitors such as Lirilumab (IPH2101; BMS-986015) from Innate Pharma; CD137 inhibitors such as urelumab (BMS-663513, Bristol-Myers Squibb), PF-05082566 (anti-4-1BB, PF-2566, Pfizer), or XmAb-5592 (Xencor); PS inhibitors such as Bavituximab; and inhibitors such as an antibody or fragments (e.g., a monoclonal antibody, a human, humanized, or chimeric antibody) thereof, RNAi molecules, or small molecules to TIM3, CD52, CD30, CD20, CD33, CD27, OX40, GITR, ICOS, BTLA (CD272), CD160, 2B4, LAIR1, TIGHT, LIGHT, DR3, CD226, CD2, or SLAM.

Further disclosed is a delivery strategy where the therapeutic MYXV virus is first adsorbed ex vivo to mixed leukocytes from either bone marrow or peripheral blood mononuclear cells prior to infusion, such as re-infusion back, into the cancer patient. In this strategy, MYXV can be delivered to metastatic cancer sites via migration of leukocytes pre-infected with virus ex vivo. This systemic delivery method is sometimes called "ex vivo virotherapy", or EVV (aka EV2), because the virus is first delivered to isolated leukocytes prior to infusion into the patient. The MYXV construct and this delivery strategy may significantly reduce tumor burden and increase survival in a subject in need thereof. In some embodiments, the BM or PBMC cells are adsorbed with MYXV constructs for one hour ex vivo, and then the MYXV-loaded leukocytes are infused back into the recipient.

In certain embodiments, the mononuclear peripheral blood cells and/or bone marrow cells are obtained from the subject, for example as autologous cells. In some embodiments, the mononuclear peripheral blood cells and/or bone marrow cells are obtained from one or more allogeneic donors, for example, a donor that is matched to the recipient for at least 1, at least 2, at least 3, at least 4, at least 5, at least 6, at least 7, or at least 8 HLA alleles (such as one or both copies of HLA-A, HLA-B, HLA-A, and/or HLA-DR alleles). HLA alleles can be types, for example, using DNA-based methods. In some embodiments, the mononuclear peripheral blood cells and/or bone marrow cells are obtained from one or more heterologous donors.

EXAMPLES

These examples are provided for illustrative purposes only and not to limit the scope of the claims provided herein.

Example 1—Virus Construction

Recombinant plasmids were designed for insertion of hDecorin, and hIL12 nucleic acid sequences at the myxoma virus M153 locus, with or without a dsRed nucleic acid sequence. A human Decorin gene was PCR amplified from a cDNA ORF clone from OHu16408 (GenScript). Human subunits IL-12 p35 and p40 were obtained from vMyx-huIL-12-GFP described in Journal of Virology, November 2007, P. 12704-12708, the disclosure of which is incorporated herein by reference. A red fluorescent protein (dsRed) gene was inserted immediately downstream of a hDecorin-hIL-12 expression cassette, and its expression was driven by a poxvirus P11 late promoter. This recombinant nucleic acid is referred to as vMyx-Triple or vMyx-Triple-red. The dsRed served as a fluorescent marker for MYXV replication in vitro and in vivo, as MYXV infection could be monitored by live imaging of dsRed expression. A second version of this recombinant nucleic acid was made that lacked the dsRed marker (referred to as vMyx-Triple-white).

FIG. 1A diagrams construction of a vMyx-Triple recombinant nucleic acid. The top image depicts a vMyx-hTNFa-GFP genome and the insertion site (M153 locus) of the expressing hDecorin-hIL-12-dsRed cassette. The middle image shows the hDecorin-hIL-12-dsRed cassette, and the bottom image shows a vMyx-Triple construct. Decorin and IL-12 transgenes in the hDecorin-hIL-12-dsRed cassette were expressed under the control of a poxvirus synthetic early/late promoter (sE/L), while expression of dsRed was controlled by the poxvirus late promoter, P11. The vMyx-Triple-white construct is identical to vMyx-Triple-red but lacks the dsRed cassette.

Figure 2A:
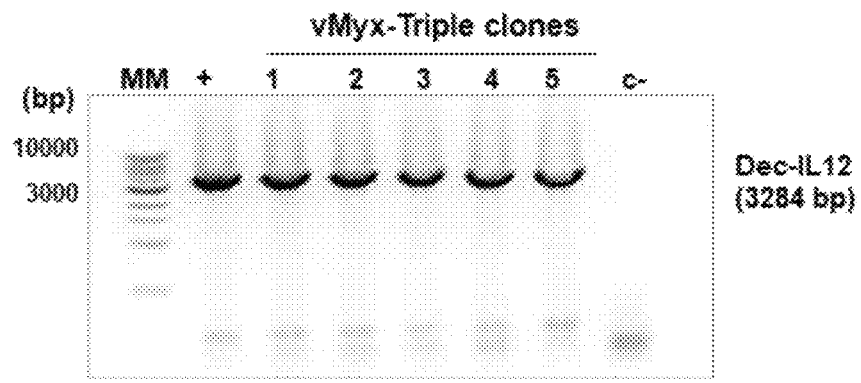
FIGS. 2A-2D are images of agarose gels showing genetic control of recombinant MYXV constructs.
Figure 2B:
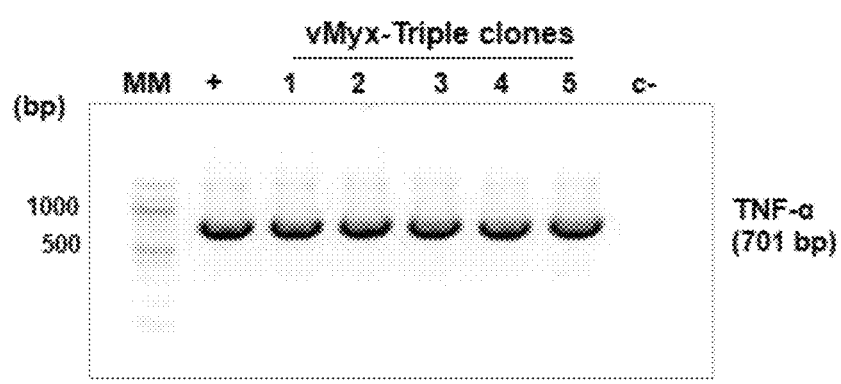

To create the vMyx-Triple and vMyx-Triple-white viruses, a recombinant plasmid was first constructed using Gateway System (ThermoFisher Scientific). Upstream and downstream hybridizing sequences were amplified by PCR to generate entry clones by Gateway BP recombination with appropriate pDONR vectors. The final recombinant plasmid was constructed by recombining three entry clones with a destination vector in a sequential manner. The hDecorin-hIL12-dsRed expression cassette was inserted into the MYXV genome by infecting RK13 cells with vMyx-hTNFa-GFP virus and then transfecting with an appropriate recombination plasmid. Multiple rounds of foci purification were conducted to obtain pure stocks of recombinant virus, using the fluorescent dsRed protein as a selection marker. The presence of the transgenes was confirmed by PCR (FIGS. 2A and 2B) using specific primers for hTNF, hDecorin and hIL-12. This PCR analysis shown in these figures verified that transgenes were present in various vMyx-Triple clones, and the bands shown in the figures were at the expected sizes. Table 1 includes primer sequences used in generating the constructs.

TABLE 1

| SEQ ID NO | Name | Primer Sequence |
|---|---|---|
| 1 | hTNFF | GGGGACAACTTTTCTATACAAAGTTGCCAA AAATTGAAATTTTATTTTTTTTTTTGGGA |
| 2 | hTNF_R | GGGGACACCTTTATTATACAAAGTTGAGGG CAATGATCCCAAAGT |
| 3 | AttB4r_hDCN_F | GGGGACAACTTTTCTATACAAAGTTGCCAAA ATTGAAATTTTATTTTTTTTTTTGGAATA TAAATAATGAAGGCCACTATCATCCTCC |
| 4 | hDCN_R_Over | CTGGATCTATCAACAGGAGTCCAAGCTTAC TTATAGTTTCCGAGTTG |
| 5 | hIL12_F_Over | GCTTGGACTCCTGTTGATAGATCCAGAAAA ATTGAAATTTATTTTTTTTTTTGGAATA TAAATAATGTGTCACCAGCAGTTGGTCATC |
| 6 | AttB3r_hIL12_R | GGGGACAACTTTATTATACAAAGTTGTTTA GGAAGCATTCAGATAGCTCATC |
| 7 | attB1_M152_F | GGGGACAAGTTTGTACAAAAAAGCAGGCTC GTAGACGCGGTGTTTCTATCC |
| 8 | M154-attB2-R | GGGGACCACTTTGTACAAGAAAGCTGGGTA AACGTAACACCGTAACTGCC |
| 9 | M153-F | ATGGCTACTGTTGTAAACATGG |
| 10 | M153-Rev | CTAAGCGGGTGACTCCACGACG |

Figure 2C:
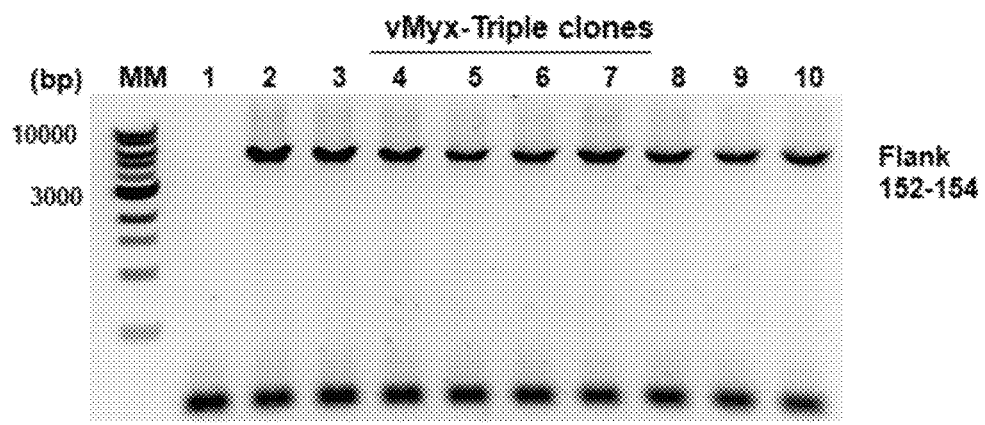
Figure 2D:
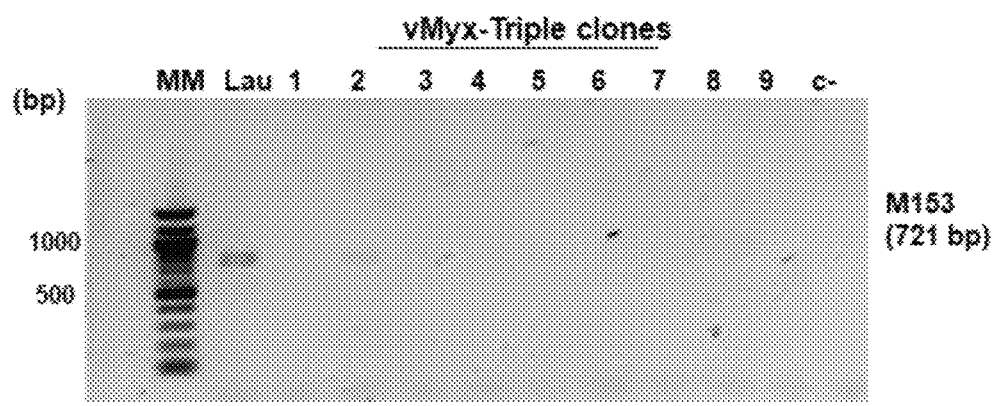
Figure 3A:
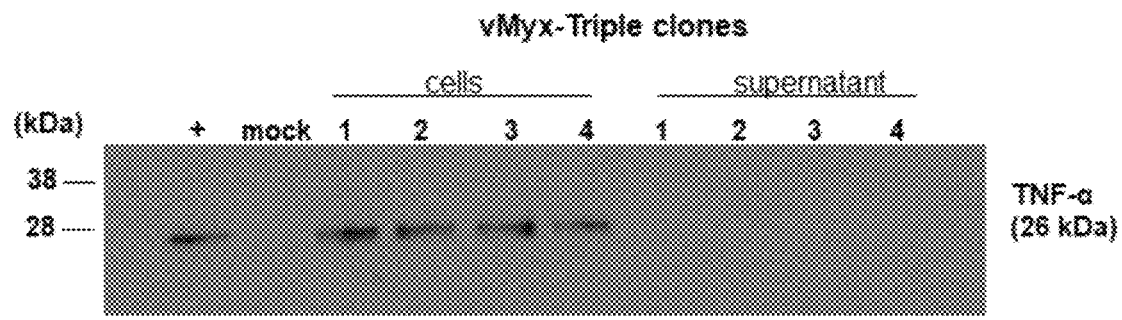
FIGS. 3A-3C are images of western blots showing protein expression of the transgenes in vMyx-Triple viruses. The western blot analysis was performed on cell lysates and supernatants from vMyx-Triple virus-infected cells, using specific antibodies to confirm protein expression of the three transgenes hTNF (FIG. 3A), hDecorin (FIG. 3B), and hIL-12 (FIG. 3C).
Figure 3B:
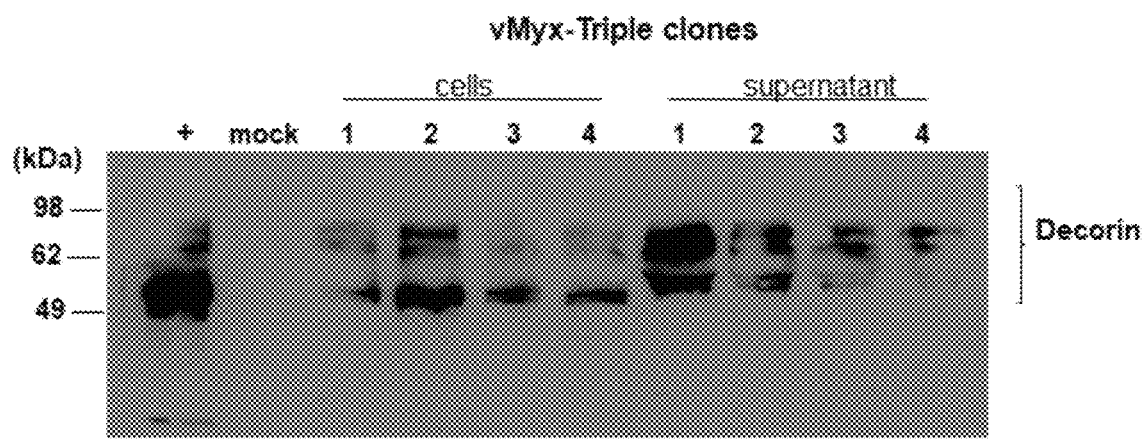
Figure 3C:
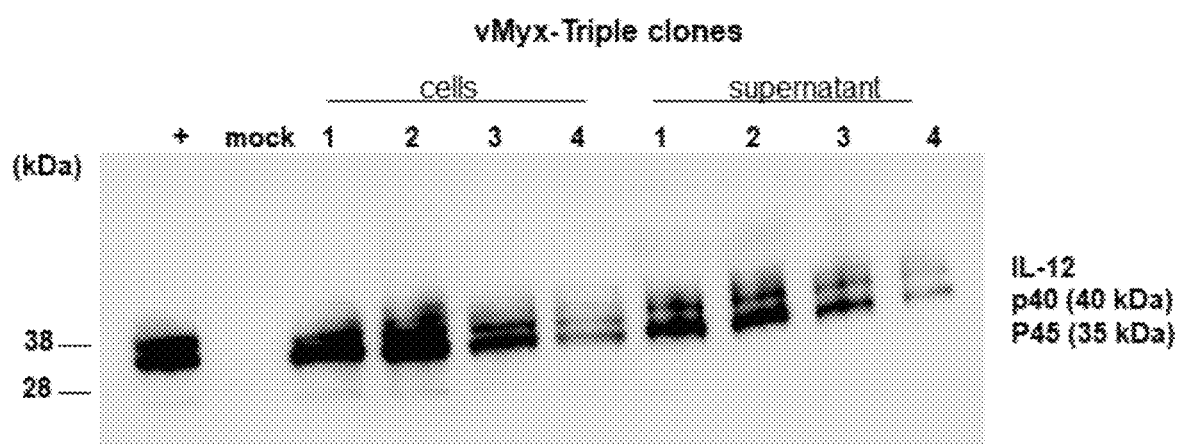

The purity of the recombinant vMyx-Triple and vMyx-Triple-white viruses, and the lack of M153, was confirmed by PCR using the appropriate primer sets (FIGS. 2C and 2D). The PCR analysis shown in FIG. 2C verified that the clones were clean of wild type virus, by using primers in the flanking regions of 135 and 136 genes. A western blot confirmed protein expression of the three transgenes (FIGS. 3A-3C). Thus, recombinant MYXVs expressing transgenic human TNFα, decorin, and IL-12, and lacking M153, were generated (vMyx-Triple). Antibodies used to detect transgene expression were as follows: human TNF-α: Monoclonal Mouse IgG1 Clone #28401 (MAB610-100, R&D Systems); human Decorin: Rabbit polyclonal antibody (ab175404, Abcam); human IL-12: Rabbit polyclonal to IL-12 p70 antibody (ab25105, Abcam).

Recombinant MYXV that expresses mouse IL-12 rather than human IL-12 were generated using the same Gateway System (ThermoFisher Scientific) as used for the viruses expressing human IL-12. A virus that expresses relatively lower levels of mouse IL-12 was generated using a synthetic early/late promoter with an IRES sequence between the subunits of IL-12 (msTriple IL-12 low), and a vMyxv-msTriple that expresses relatively higher levels of mouse IL-12 was generated using a synthetic early/late promoter with mouse IL-12 that contained an Elastin linker between the subunits of IL-12 (msTriple IL-12 high).

Example 2—Replication and Cell Killing Capacity of Recombinant MYXV

Figure 4:
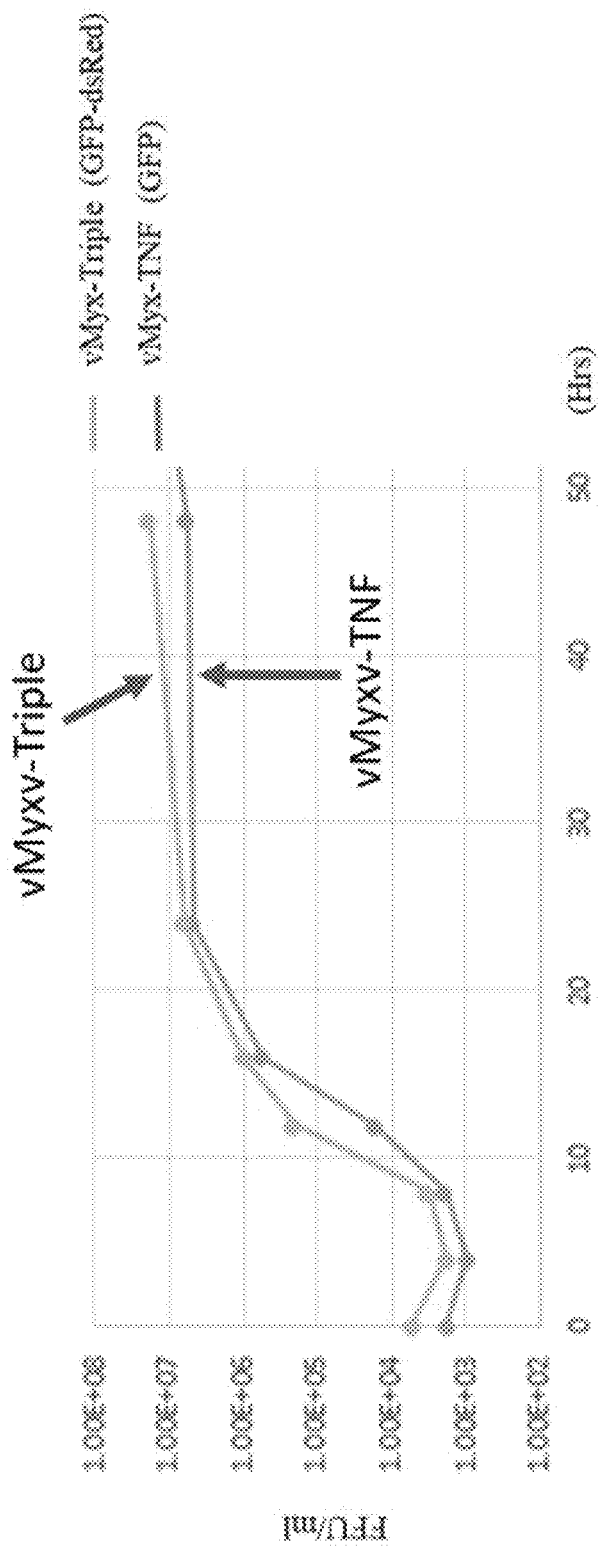
FIG. 4 is a chart showing a single-step growth analysis of recombinant vMyx-Triple viruses. The replication capacities in RK13 cells of vMyx-Triple viruses was similar to the parental virus vMyx-TNF-GFP. MOI=1.

The replication capacity of the vMyx-Triple virus prepared in Example 1 was tested in RK13 cells. The replication capacity of vMyx-Triple virus was similar to the parental vMyx-hTNFa-GFP virus (FIG. 4). Thus, a recombinant MYXV expressing transgenic human TNFα, decorin, and IL-12, and lacking M153, effectively replicated in host cells.

Figure 5A:
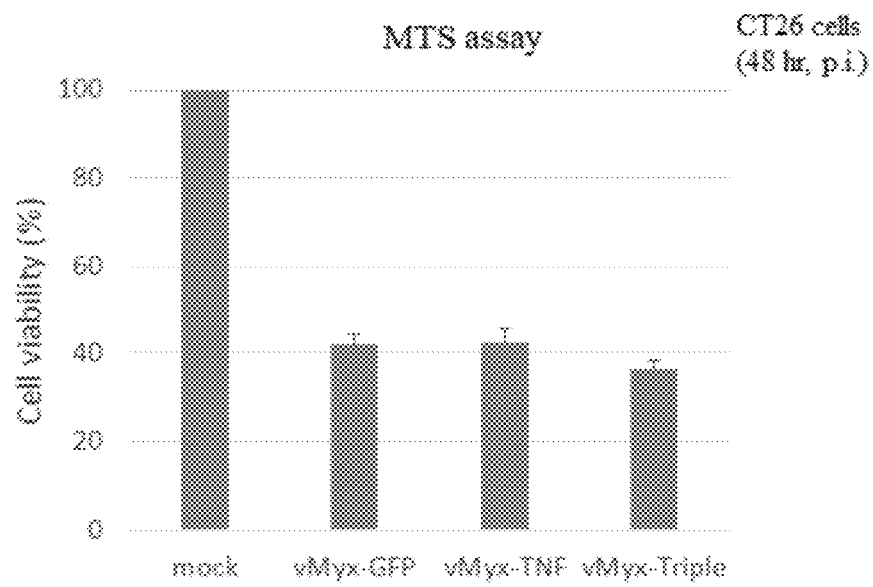
FIGS. 5A and 5B are graphs showing results of a cell viability assay. The cell killing capacity of a vMyx-Triple virus was tested in two different cell lines: CT26 (murine colon carcinoma) and HELA (human cervical cancer). Cells were infected at MOI=10 for 48 hrs, and then the MTS assay was performed.
Figure 5B:
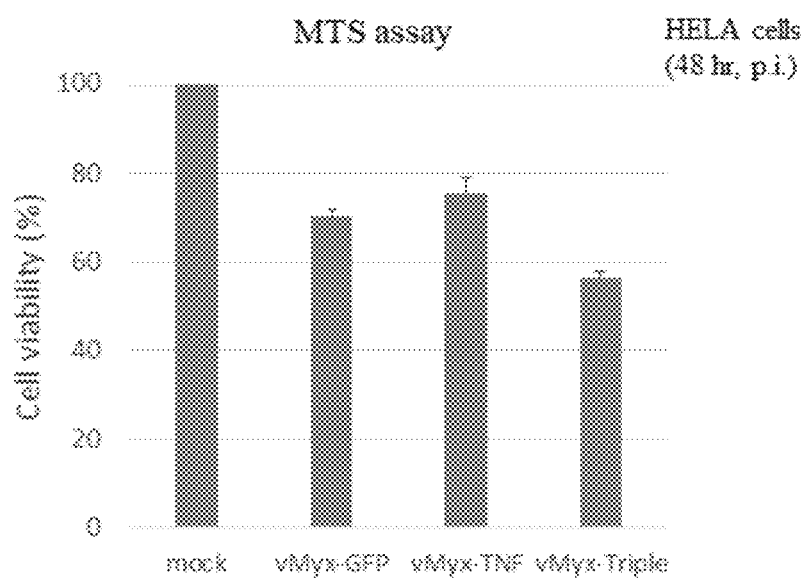

Next, the cell killing capacity of the vMyx-Triple virus was tested in two different cell lines: CT26 (colon carcinoma) and HELA (human cervical cancer (FIGS. 5A and 5B). To measure cell viability (and thus infer cytotoxicity), a CellTiter 96® AQueous One Solution Cell Proliferation Assay (MTS) was used (Promega, USA). CT26 and HELA cells were infected with the different viruses for 48 hr at a multiplicity of infection (MOI) of 10. After 48 hours, a tetrazolium substrate (MTS) was added to the CT26 and HELA cells and an A490 formazan product produced in viable cells was measured using a microplate reader after 2 hr of incubation. Each sample was quantified in triplicate and a total of two independent experiments were performed. The vMyx-Triple virus induced similar levels of cell death in both cell lines, as compared with the parental virus vMyx-hTNFa, and also as compared with vMyx-GFP. There was a trend towards increased cancer cell killing by the vMyx-Triple virus compared to the other viruses. Thus, a recombinant MYXV expressing transgenic human TNFα, decorin, and IL-12, and lacking M153, was cytotoxic to cancer cells.

Example 3—Replication and Cell Killing Capacity of Recombinant MYXV

Figure 1B:
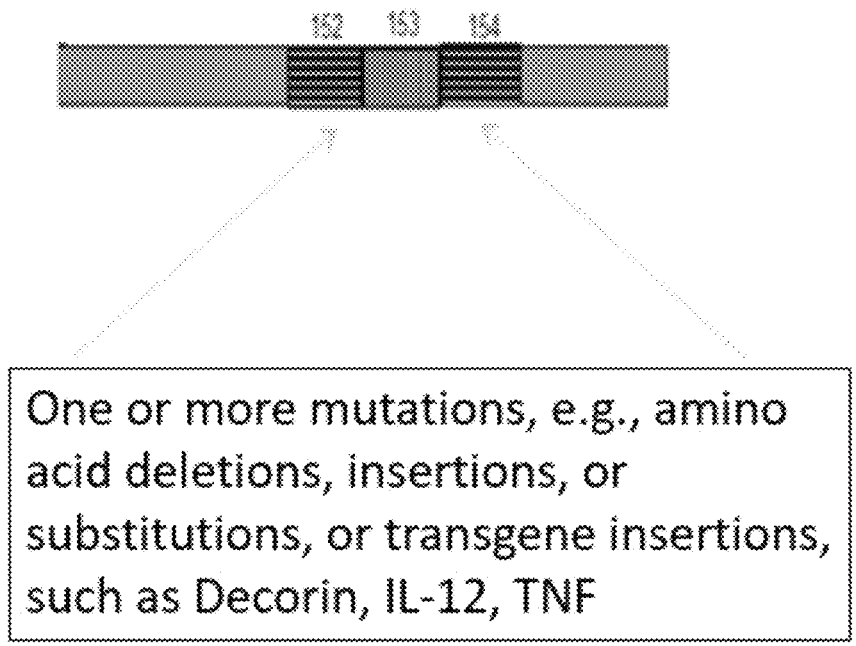
FIG. 1B is a schematic of the M153 locus in recombinant nucleic acids, which can be modified with a mutation or a transgene insertion. Recombinant nucleic acids with a modified M153 locus can be introduced into a MYXV genome using methods disclosed herein.

FIG. 1B diagrams the M153 locus, which can be modified in recombinant nucleic acids and MYXV of the disclosure. The modification can include a mutation in the M153 sequence, for example, an insertion, a deletion, a substitution, or a combination thereof. The modification can attenuate an activity or expression level of M153. The modification can include deletion of M153 gene and/or replacement of M153 gene with one or more transgenes. The replacement gene can be selected from hTNFa, hDecorin, IL-12, or another transgene that help enhance the oncolytic activity or decrease adverse side effects of the MYXV.

To create the vMyx constructs, a recombinant plasmid can be first constructed using Gateway System (ThermoFisher Scientific). Upstream and downstream hybridizing sequences are amplified by PCR to generate entry clones by Gateway BP recombination with appropriate pDONR vectors. The final recombinant plasmid is constructed by recombining one or more entry clones with a destination vector in a sequential manner. The recombinant plasmid is inserted into the MYXV genome by infecting RK13 cells with vMyx and then transfecting with an appropriate recombination plasmid. Multiple rounds of foci purification are conducted to obtain pure stocks of recombinant virus. A selection marker can be used, such as a fluorescent protein, for example, dsRed. The presence of the transgenes can be confirmed by PCR and/or sequencing.

An M153 knockout virus can be constructed in this manner. The recombinant plasmid can be designed to contain sequences that flank the sequence of the M153 gene, without the M153 gene sequence. Optionally, an expression cassette for a fluorescent protein can be included. The M153 knockout can be generated by infecting RK13 cells with MYXV and transfecting the cells with the recombination plasmid. Multiple rounds of foci purification are conducted to obtain pure stocks of M153KO virus, optionally using the fluorescent protein as a selection marker. The M153 knockout and purity of the virus is confirmed via PCR analysis using suitable primers.

The replication capacity of the modified vMyx virus can be tested in RK13 cells. The replication capacity of a modified vMyx virus can be similar to the parental vMyx virus. Next, the cell killing capacity of the modified vMyx virus is tested in two different cancer cell lines. To measure cell viability (and thus infer cytotoxicity), a CellTiter 96® AQueous One Solution Cell Proliferation Assay (MTS) is used (Promega, USA). Cancer cells are infected with the different viruses for 48 hr at MOI=10. After 48 hours, a tetrazolium substrate (MTS) is added to the cells and an A490 formazan product produced in viable cells is measured using a microplate reader after 2 hr of incubation. Each sample is quantified in triplicate and a total of two independent experiments is performed. The modified vMyx virus can induce similar levels of cell death in both cell lines, or higher levels of cell death, as compared with the parental virus vMyx, and also as compared with vMyx-GFP.

Example 4—In Vitro Results with M153KO MYXV

Therapeutic transgenes can be added to MYXV at two types of genomic loci: as a disruption construct within protein coding genes, such that the recombinant virus is a genetic "knockout" of that virus gene, or else at "innocuous" intergenic locus that is predicted to not affect the biology or oncolytic potential of the recombinant virus. When endogenous virus genes are knocked out, it is possible that the new knockout construct will differ from the parental virus in terms of its oncolytic capacity against cancer cells, independent of which transgenes are inserted into the locus.

The M153 gene of MYXV encodes an immunoregulatory protein from a family of E3-Ubiquitin ligases that participates in the down-regulation of diverse cellular receptors, including MHC class-I and CD4 proteins. Without wishing to be bound by theory, inactivation or knockdown of M153 can result in enhanced expression of MHC-I dependent immune epitopes, for example, increased direct presentation of viral and/or tumor antigens, thereby increasing recognition of virally infected cells (e.g., cancer cells) by host T cells. This allows a myxoma virus with an inactivated M153 gene to be used as an oncolytic vector. The data in this and the following example indicate that a M153 knockout myxoma virus (M153KO MYXV) backbone exhibited higher oncolytic activity in vitro and in vivo than a parental MYXV with an intact M153 gene in an immunocompetent model. As such, a M153KO MYXV without a transgene exhibited a greater oncolytic activity than the parental MYXV or wt MYXV. In addition, M153KO MYXV with one or more transgenes can also exhibit an enhanced oncolytic activity than the parental MYXV or wt MYXV.

Figure 6:
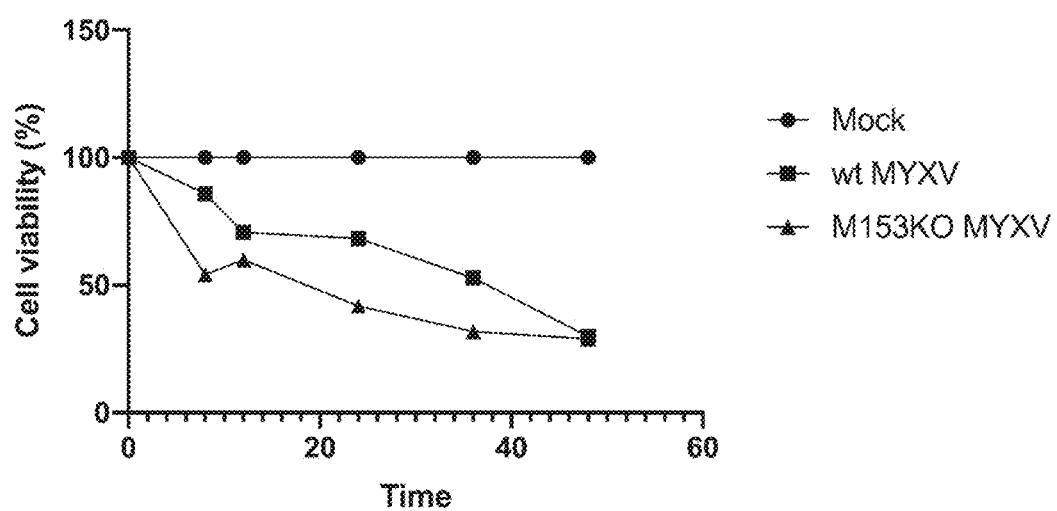
FIG. 6 is a chart showing cell death induced by viral infection with a wild type MYXV or a M153KO MYXV, and showing cell death in untreated B16F10 cells (mock).

In B16F10 cells, a murine melanoma cell line, a M153KO MYXV was tested for induction of cell killing compared to a wild-type myxoma virus that contains an intact wild type M153 (wt MYXV). This M153KO MYXV did not include hTNFa, hDecorin, hIL-12A, or hIL-12B transgenes. The M153KO MYXV reduced cell viability in the B16F10 cells to a greater extent than the wt MYXV at early time points post-infection, up to approximately 36 hours post-infection (FIG. 6). These results suggest that a MYXV with the M153 inactivation or knockdown induces cell death to a greater extent than a wild type or a MYXV without the M153 inactivation.

Based on this result, the possibility that the M153KO virus may induce a specific type of cell death, called Immunogenic Cell Death (ICD), was evaluated to determine the potential of the M153KO MYXV as an oncolytic vector to induce ICD in cancer cells. There are different hallmarks in vitro that can indicate induction of CD, which can stimulate the immune system (for example, the adaptive immune system). In this case, two signals were the focus of this investigation: release of ATP to the extracellular environment, and expression of calreticulin on the surface of the cell or ecto-expression.

Figure 7A:
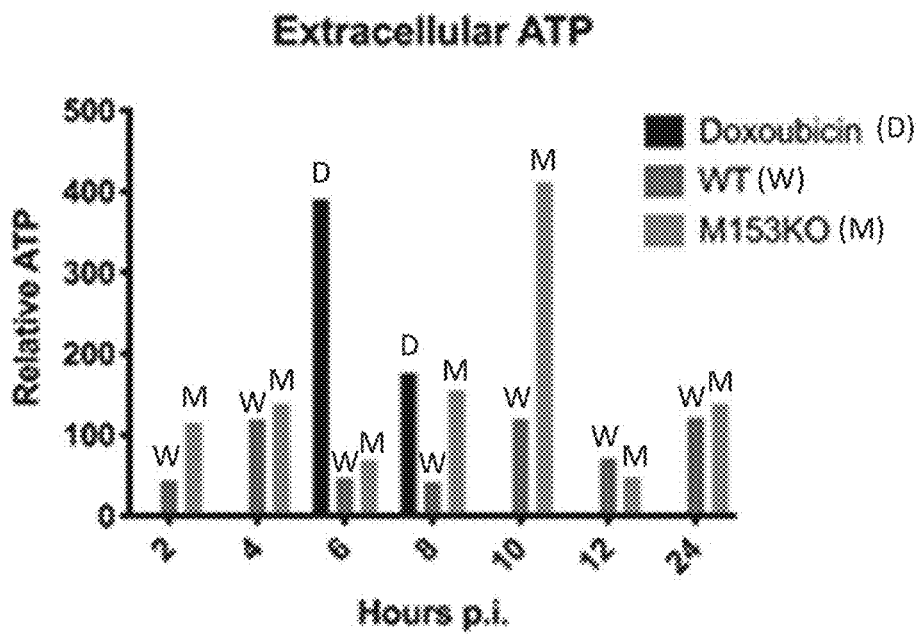
FIGS. 7A and 7B are graphs showing immunogenic cell death induced by M153KO MYXV in B16F10 murine cells in vitro.

The release of ATP from dying cells can indicate ICD. ATP release observed after infection with the wt MYXV was not significantly different from negative controls. On the other hand, the amount of ATP released after infection with the M153KO MYXV was higher than in untreated cells, and up to about four-fold higher than for cells infected by wt MYXV (see, FIG. 7A, for example, the peak value at 10 hours post-infection). The peak result from M153KO MYXV infection was similar to the peak values obtained with a drug-induced positive control (Doxorubicin), but at a later time (FIG. 7A, see results at 6-10 hrs post-infection). Thus, a MYXV with an inactivation or knockdown of M153 has superior oncolytic properties compared to a wt MYXV or compared to a MYXV without the M153 inactivation or knockdown. In particular, a MYXV with the M153 inactivation or knockdown induces immunogenic cell death to a greater extent than a MYXV without the M153 inactivation or knockdown or a WT MYXV.

Figure 7B:
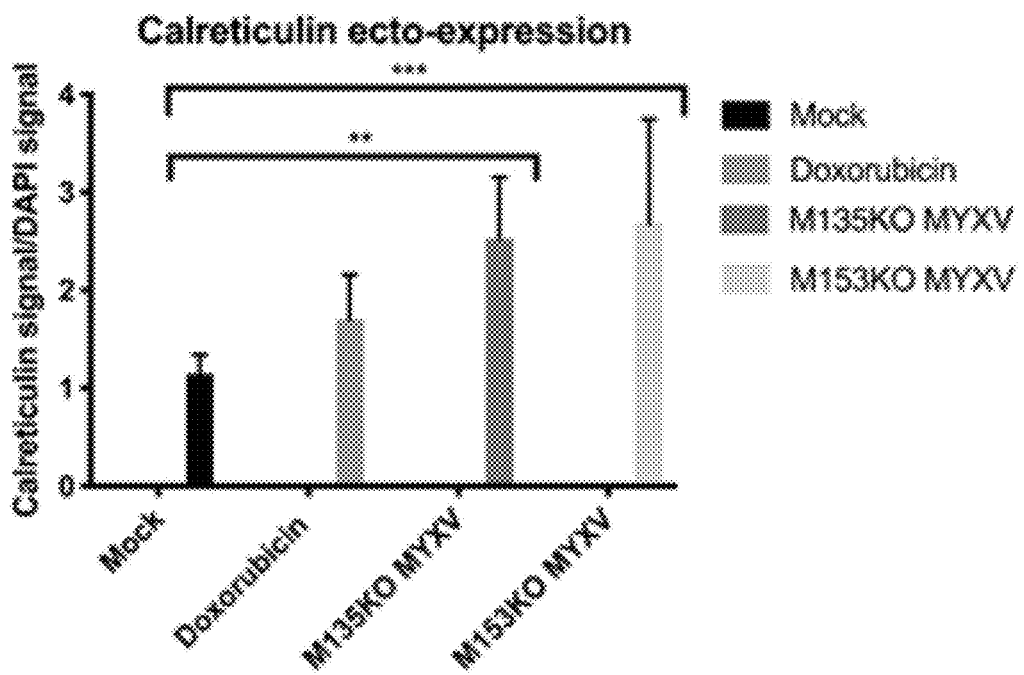
Figure 8:
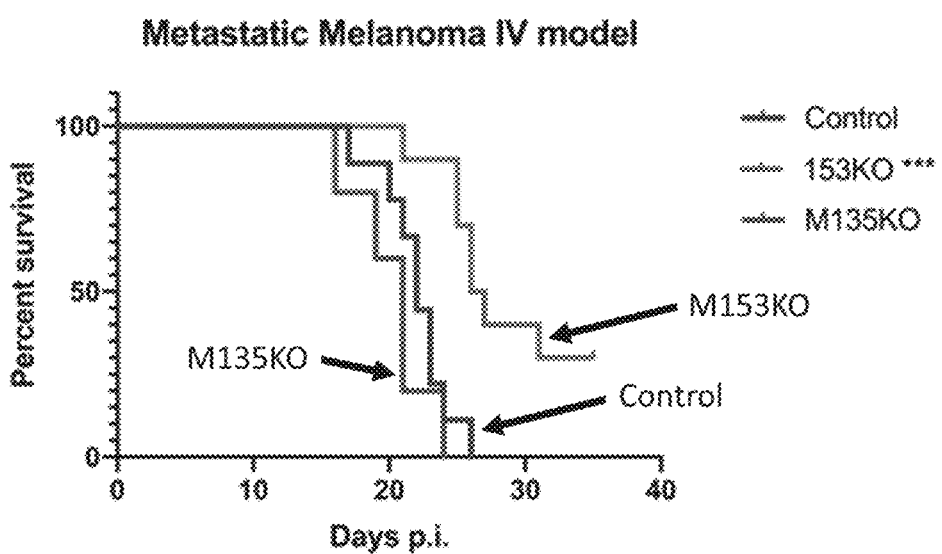
FIG. 8 is a chart showing a survival curve in a metastatic melanoma mouse model (B16F10) when mice were left untreated (control; middle line), treated with a M153KO MYXV (153KO; line extending to the right) or treated with a M135KO MYXV as a second control (M135KO; left line). Days p.i.=days post implantation.
Figure 9A:
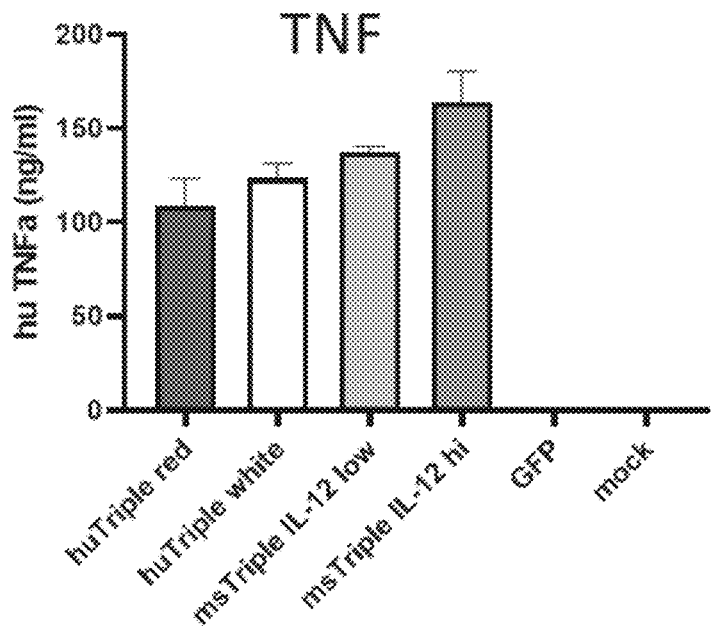
FIGS. 9A-9D show the concentration of cytokines in the supernatants of Vero cells infected with MYXV of the disclosure.
Figure 9B:
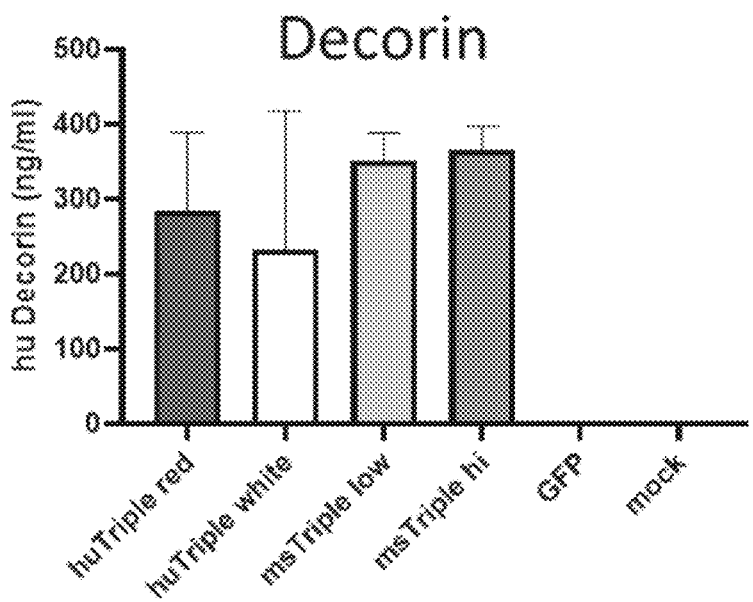
Figure 9C:
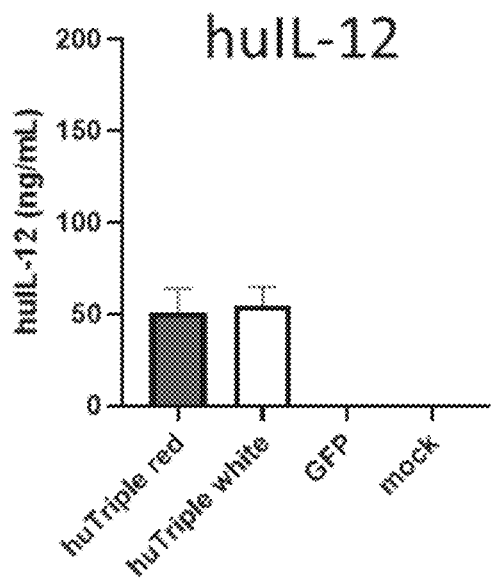
Figure 9D:
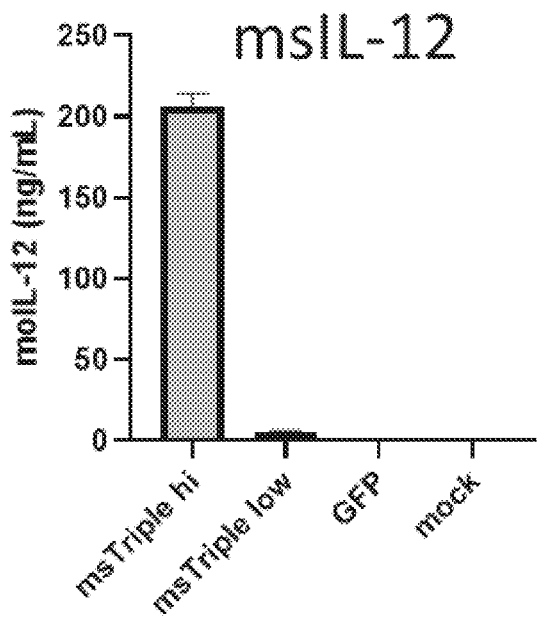
Figure 10A:
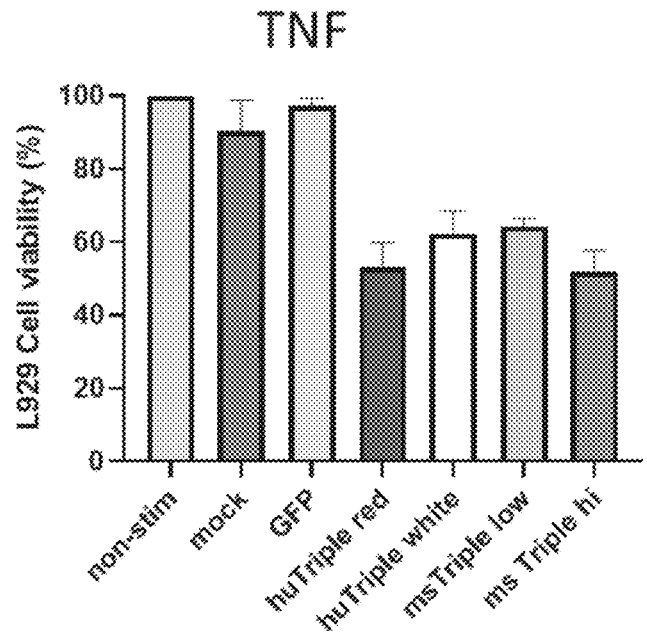
FIG. 10A shows the viability of L929 cells after exposure to supernatants of Vero cells infected with MYXV of the disclosure, which is indicative of TNF biological activity.
Figure 10B:
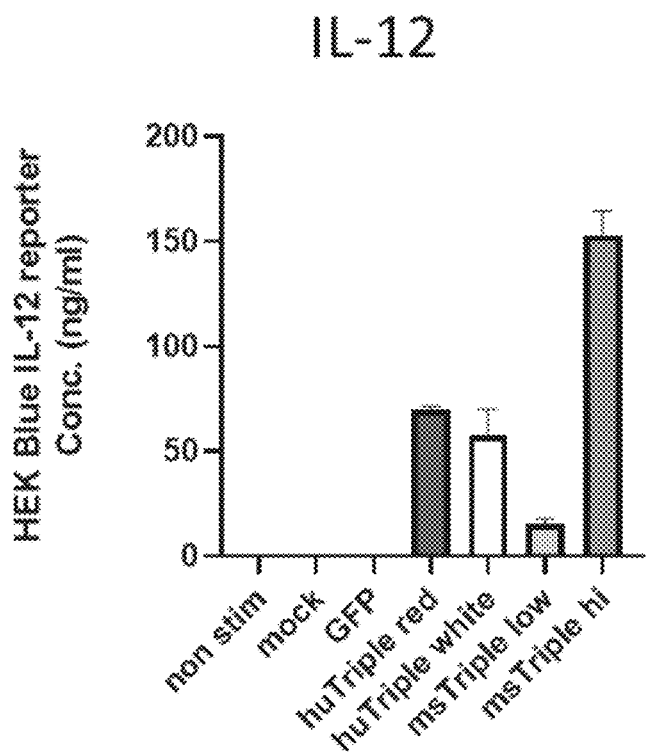
FIG. 10B shows the expression of a reporter gene after exposure of HEK Blue IL-12 cells to supernatants of Vero cells infected with MYXV of the disclosure. When no bar is present, the level of the analyte was below the limit of detection for the assay.

Calreticulin is usually expressed within the endoplasmic reticulum, but where ICD is occurring, it can be expressed on the cell surface (ecto-expression). Ecto-expression of calreticulin was evaluated using confocal microscopy and quantified using a ratio of the signal of the calreticulin observed per signal of a nuclear stain (DAPI) that represents each cell. In this case, the M135KO MYXV was used as a representation of an unarmed virus with a genetic knockout lesion in an unrelated viral gene (M135) that does not alter cell killing caused by the parental MYXV and behaves similarly to wt MYXV in this regard. The induction of ecto-expression of calreticulin higher in M153KO MYXV-infected cells than in M135KO MYXV-infected or Doxorubicin-treated cells (FIG. 7B).

Overall, these results showed that the M153KO MYXV can induce hallmarks of ICD in B16F10 cells in vitro, and may induce the immune system (e.g., the adaptive immune system) when used in vivo. Thus, a MYXV with a M153 inactivation or knockdown induces ICD in melanoma or cancer cells. A MYXV with a M153 inactivation or knockdown can also stimulate the immune system (e.g., the adaptive immune system).

Example 5—In Vivo Results with M153KO MYXV

Additionally, studies were performed with a syngeneic metastatic melanoma mouse model, using the same murine cancer cell line, B16F10, as used for the in vitro studies. In this case, C57BL/6 mice were seeded via intravenous injections in the tail vein with B16F10 cells to induce dispersed metastatic melanoma lesions in the lungs. Three days after implantation of the melanoma cells, mice were treated with $2\times10^7$ ffu of M153KO MYXV or a saline control via intravenous injections in the retro-orbital area. Mice treated with one dose of the M153KO virus showed fewer signs of metastatic disease, and survived longer than the control mice (FIG. 8). The M135KO MYXV contains a gene knockout in an unrelated virus gene involved in rabbit pathogenesis, and is used as a control here to measure any oncolytic effects caused by the virus in the absence of M153KO. In this model, M153KO virus provided significantly longer term survival compared to untreated control mice, but the M135KO virus did not.

These results show that M153KO MYXV can be used as an oncolytic vector platform with superior anti-cancer effects compared to a parental MYXV with an intact M153 gene or compared to a wt MYXV. Thus, a MYXV with a M153 inactivation or knockdown prolongs survival in a subject with cancer (for example, melanoma). The cancer or melanoma can be metastatic. The mice treated with M153 knockout showed significant improvement in survival rate and survival length than the control group.

Example 6—Transgene Expression by Infected Cells

This example demonstrates that cells infected with myxoma viruses of the disclosure secrete TNF, Decorin, and IL-12, and further demonstrates that the secreted TNF and IL-12 have biological activity.

Vero cells were infected with vMyx-Triple (huTriple red and huTriple white), msTriple IL12 low, msTriple IL-12 hi, each at an MOI of 1. As a control, cells were infected with vMyx-GFP, which does not encode any of the cytokines, and contains an intact M153 gene. After 24 hours, supernatant was harvested and ELISA assays conducted to determine the concentration of each of the cytokines in supernatant (FIGS. 9A-9D). The results demonstrate that cells infected with the various vMyx-Triple viruses secrete TNF (FIG. 9A), Decorin (FIG. 9B), and IL-12 (FIG. 9C—human IL-12; FIG. 9D—murine IL-12). In contrast, the cytokines were not detected in mock-infected cells, or cells infected with vMyx-GFP. Infection with msTriple IL-12 hi was shown to elicit higher expression of mouse IL-12 than infection with msTriple IL-12 low.

To test whether the TNF secreted by infected cells was biologically active, an assay was conducted utilizing L929 cells, which are sensitive TNF, and lose viability upon sufficient exposure to biologically active TNF. L292 cells were exposed to supernatants from Vero cells that had been infected with the indicated viruses. As shown in FIG. 10A, cells infected with the various vMyx-Triple viruses generate biologically-active TNF, while cells infected with vMyx-GFP do not. These results show that MYXV of the disclosure that encode TNF can elicit expression of biologically active TNF.

To test whether the IL-12 secreted by infected cells was biologically active, a HEK Blue IL-12 reporter assay was conducted. The HEK Blue IL-12 cells express a reporter gene in response to biologically active IL-12, and the reporter gene can be detected using a colorimetric assay. As shown in FIG. 10B, supernatants from Vero cells infected with the vMyx-Triple viruses elicited reporter gene expression, while controls, including supernatants from cells infected with vMyx-GFP, did not. These results show that MYXV of the disclosure that encode IL-12 can elicit expression of biologically active IL-12.

Example 7—Inhibition of Growth of Cancer Cell Lines In Vitro by vMyx-Triple

The ability of vMyx-Triple to inhibit growth of multiple cancer cell lines was evaluated in vitro. Cells were infected at multiplicities of infection (MOI) of 0.1, 1, or 10 focus forming units (FFU) per cell. After incubation for 72 hours, cell viability was tested using a CellTiter-Glo Cell Viability Assay, and mean growth inhibition was determined. The results showed that vMyx-Triple could inhibit growth of a range of human and mouse cancer cell lines derived from different tissues. Results are provided in Table 2.

TABLE 2

| | | Mean Growth Inhibition (%) vMyx-Triple | | |
|---|---|---|---|---|
| Cell Line | Tissue Type | 0.1 ffu/cell | 1 ffu/cell | 10 ffu/cell |
| MDA-MB-231 | Human Breast | 0.40 | 4.65 | 47.95 |
| MDA-MB-468 | Human Breast | 2.35 | 1.60 | 45.90 |
| HCT-116 | Human Colon | 0.80 | 2.20 | 5.80 |
| COLO 205 | Human Colon | 2.95 | 12.45 | 71.30 |
| RPMI-8226 | Human Myeloma | 0.00 | 13.30 | 87.35 |
| CCRF-CEM | Human Leukemia | 24.85 | 25.35 | 39.35 |
| SK-MEL-28 | Human Melanoma | 0.65 | 4.20 | 56.90 |
| A375 | Human Melanoma | 0.00 | 8.70 | 62.60 |
| A549 | Human NSCLC | 4.35 | 11.10 | 66.15 |
| H460 | Human NSCLC | 3.55 | 4.90 | 21.50 |
| OVCAR-3 | Human Ovarian | 5.30 | 0.70 | 1.75 |
| SKOV-3 | Human Ovarian | 6.20 | 23.15 | 71.75 |
| ASPC-1 | Human Pancreas | 16.55 | 18.75 | 48.70 |
| Capan-1 | Human Pancreas | 1.30 | 1.05 | 3.25 |
| PC-3 | Human Prostate | 0.30 | 2.15 | 33.15 |
| DU-145 | Human Prostate | 4.35 | 5.60 | 43.00 |
| 786-0 | Human Renal | 1.45 | 2.00 | 69.05 |
| RXF-393 | Human Renal | 1.30 | 4.95 | 29.15 |
| Hep3B | Human Liver | 2.40 | 3.55 | 12.00 |
| Hep-G2 | Human Liver | 4.70 | 8.45 | 63.60 |
| MBT-2 | Murine Bladder | 16.25 | 32.30 | 57.90 |
| 4T-1 | Murine Breast | 0.05 | 0.35 | 10.75 |
| CT-26 | Murine Colon | 6.30 | 25.40 | 39.75 |
| C-1498 | Murine AML | 1.50 | 1.20 | 1.30 |
| B16-F10 | Murine Melanoma | 2.15 | 9.55 | 18.20 |
| TC-1 | Murine Lung | 0.95 | 4.35 | 41.30 |
| LL/2 | Murine Lung | 0.95 | 2.05 | 6.75 |
| Pan02 | Murine Pancreas | 0.00 | 0.00 | 25.50 |
| Hepa 1-6 | Murine Liver | 0.85 | 1.60 | 46.75 |
| RENCA | Murine Renal Cell | 1.60 | 0.20 | 75.55 |
| MC38 | Murine Colon | 3.85 | 20.25 | 81.85 |

To further characterize the ability of vMyx-Triple to inhibit growth of cancer cell lines, in vitro, 17 human lung cancer cell lines were infected at 9 different multiplicities of infection ranging from 0.01 FFU/cell to 100 FFU/cell. After incubation for 72 hours, cell viability was assessed using a CellTiter-Glo Cell Viability Assay. $EC_{50}$ was calculated for each cell line, as the MOI that achieved 5000 of maximum growth inhibition, as determined by curve fit using non-linear regression analysis via GraphPad Prism software. The vMyx-Triple demonstrated inhibition of a number of the human lung cancer tumor cell lines, with EC50s shown in Table 3.

TABLE 3

| Cell Line | Tissue Type | Mean $EC_{50}$ (ffu/cell) |
| --- | --- | --- |
| H1650 | Human NSCLC | 17.20 |
| H1975 | Human NSCLC | 4.73 |
| H358 | Human NSCLC | 11.18 |
| H441 | Human NSCLC | 33.37 |
| HCC827 | Human NSCLC | >100* |
| LK-2 | Human Squamous Cell Lung | 19.94 |
| NCI-H226 | Human Squamous Cell Lung | 10.14 |
| SK-MES-1 | Human Squamous Cell Lung | 5.59 |
| H720 | Human Lung Carcinoma | >100* |
| H820 | Human Lung Adenocarcinoma | 5.61 |
| A427 | Human Lung Carcinoma | 8.13 |
| H209 | Human SCLC | >100* |
| H69 | Human SCLC | 12.54 |
| SHP-77 | Human SCLC | >100* |
| H1963 | Human SCLC | 94.88^ |
| A549 | Human NSCLC | 5.60 |
| H2228 | Human NSCLC | 53.76 |

*Value was averaged using > 100 ffu/cell value for both trial results.
^Value was averaged using > 100 ffu/cell value for one trial result.

To further characterize the ability of vMyx-Triple to inhibit growth of cancer cell lines in vitro, 8 human sarcoma cell lines were infected at 9 different multiplicities of infection ranging from 0.01 FFU/cell to 100 FFU/cell. After incubation for 72 hours, cell viability was assessed using a CellTiter-Glo Cell Viability Assay. $EC_{50}$ was calculated for each cell line, as the MOI that achieved 50% of maximum growth inhibition, as determined by curve fit using non-linear regression analysis via GraphPad Prism software. The vMyx-Triple demonstrated inhibition of a number of the human sarcoma cell lines, with EC50s shown in Table 4.

TABLE 4

| Cell Line | Tissue Type | Mean $EC_{50}$ (ffu/cell) |
| --- | --- | --- |
| 143B | Human Osteosarcoma | 17.76 |
| A204 | Human Rhabdomyosarcoma | 1.51 |
| A673 | Human Ewing's Sarcoma | 7.26 |
| HS822T | Human Ewing's Sarcoma | >100* |
| HT-1080 | Human Fibrosarcoma | 20.93 |
| KHOS/NP | Human Osteosarcoma | 30.48 |
| SJSA-1 | Human Osteosarcoma | 5.41 |
| SK-ES-1 | Human Sarcoma | 14.40 |

*Value was averaged using > 100 ffu/cell value for both trial results.

Example 8—Inhibition of Human Acute Myeloid Leukemia Samples Ex Vivo by vMyx-Triple The ability of vMyx-Triple to kill human cancer cells from patients was tested. Acute myeloid leukemia (AML) samples from human patients were exposed to vMyx-Triple, or the parental virus vMyx-GFP ex vivo, at 6 different multiplicities of infection (MOI) ranging from 0.01 FFU/cell to 100 FFU/cell. After incubation for 6 days of continuous culture, cell viability was tested using a CellTiter-Glo Cell Viability Assay. $IC_{50}$ was calculated for each sample, as the MOI that achieved 50% of maximum growth inhibition, as determined by curve fit using non-linear regression analysis via GraphPad Prism software.

Figure 11A:
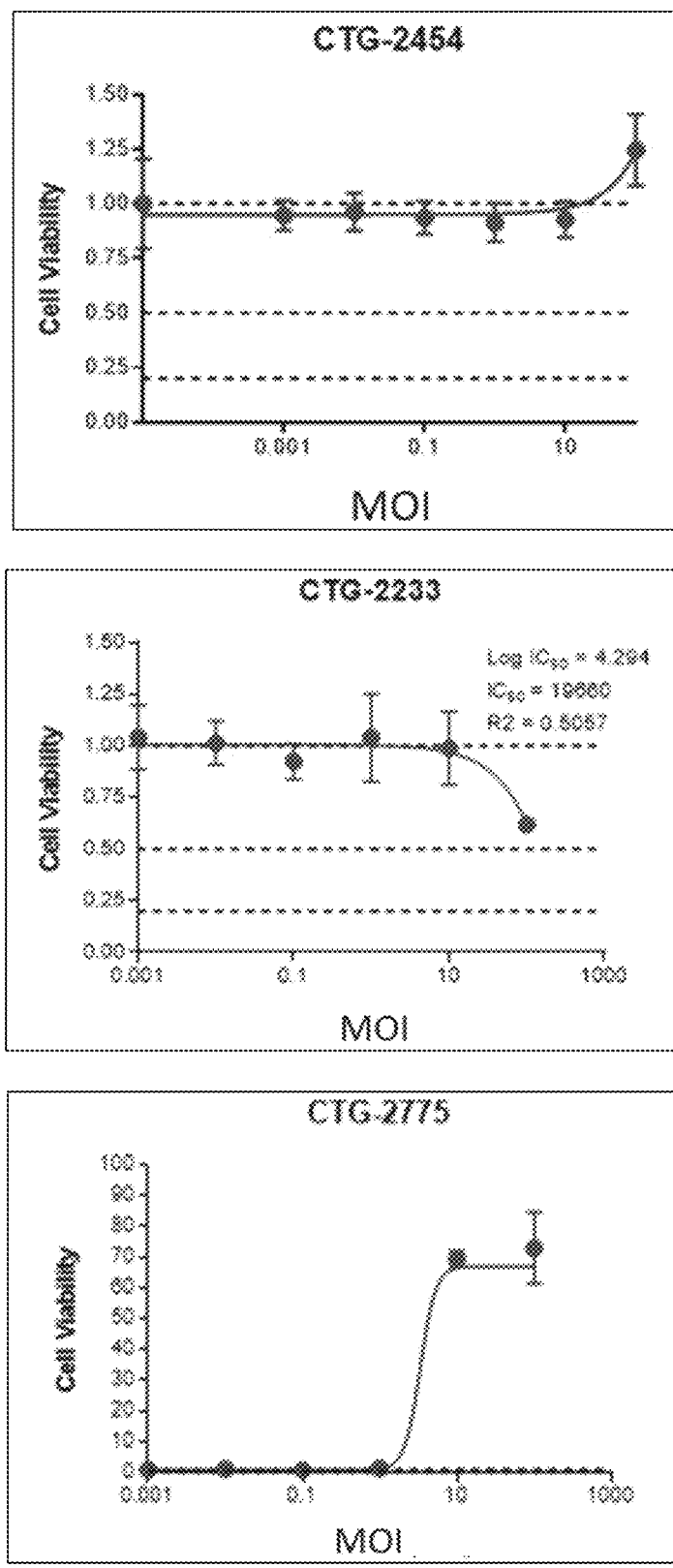
FIG. 11A shows viability of cells from human acute myeloid leukemia patients after incubation with vMyx-GFP for 6 days.
Figure 11B:
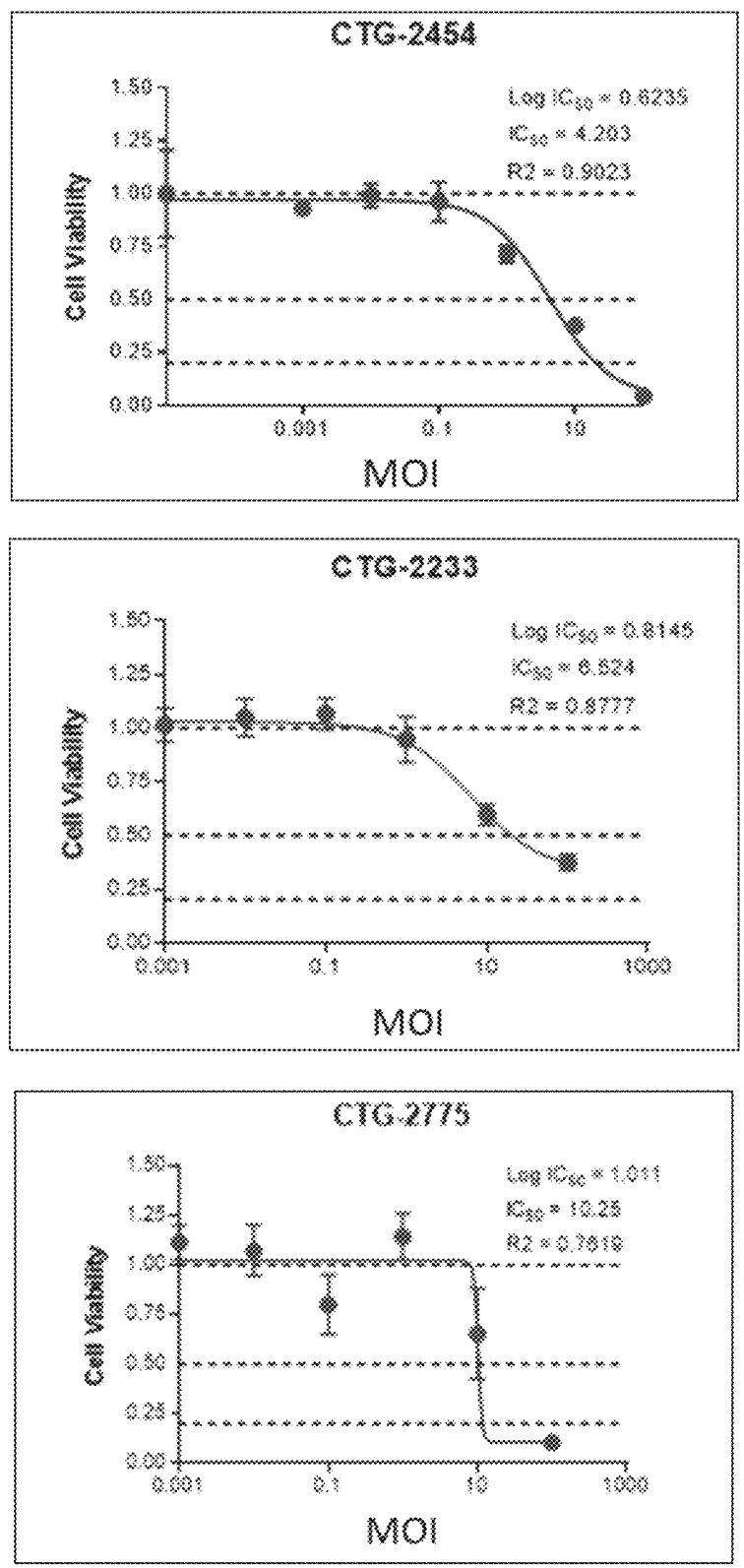
FIG. 11B shows viability of cells from human acute myeloid leukemia patients after incubation with vMyx-Triple for 6 days.

As shown in FIG. 11A, no $IC_{50}$ could be calculated for two of three samples exposed to the parental virus, while an $IC_{50}$ of 19660 was calculated for the other sample. As shown in FIG. 11B, vMyx-Triple exhibited superior inhibition of human AML samples, with the $IC_{50}$s calculated at 4.203, 6.524, and 10.25. The results show that vMyx-Triple can inhibit the growth of cancer cells from human cancer patients, and exhibits superior anti-cancer effects compared to the parental virus which lacks TNF, Decorin and IL-12, and which contains an intact wild type M153 gene.

Example 9—Cytokine Production by MYXV Infected PBMCs

The ability of vMyx-Triple to elicit cytokine production by human peripheral blood mononuclear cells (PBMCs) was tested. Human PBMCs were infected with MYXV, each at an MOI of 10. The MYXV used were vMyx-Triple ("Human triple"), parental virus vMyx-GFP ("Parental MYXV"), vMyx-hTNFa-GFP ("TNF single"), and a MYXV that expresses TNF on the cell surface ("Membrane bound TNF"). The MYXV that expresses TNF on the cell surface encodes the TNFα of SEQ ID NO: 45, which contains an altered TNFα sequence that will remain membrane bound.

Figure 12A:
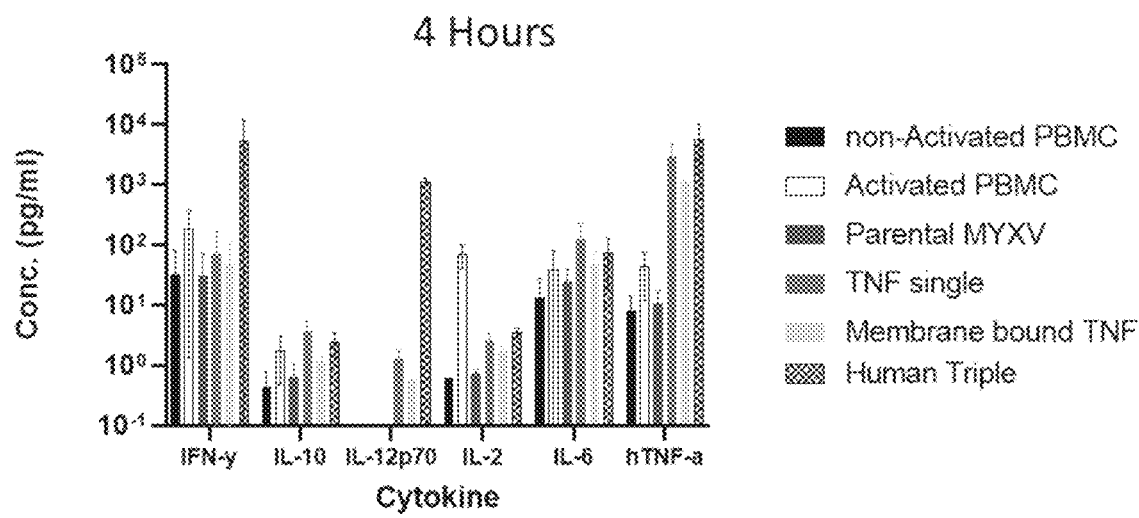
FIG. 12A shows the concentrations of cytokines in the supernatants of human PBMCs infected with the indicated MYXV at an MOI of 10, at 4 hours post-infection. Mean+/−SD is plotted. When no bar is present, the level of the analyte was below the limit of detection for the assay.
Figure 12B:
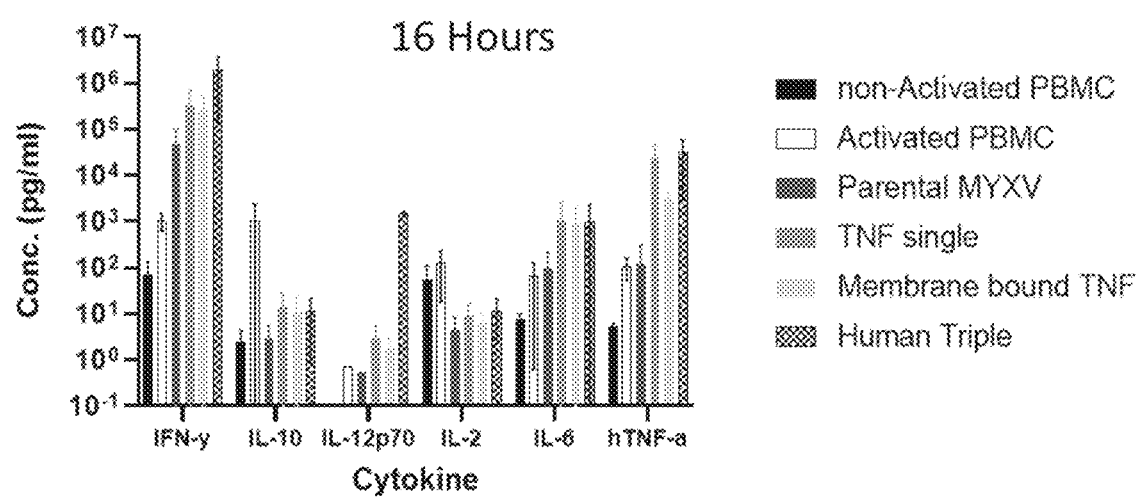
FIG. 12B shows the concentrations of cytokines in the supernatants of human PBMCs infected with the indicated MYXV at an MOI of 10, at 16 hours post-infection. Mean+/−SD is plotted. When no bar is present, the level of the analyte was below the limit of detection for the assay.

Untreated PBMCs were used as a negative control, and PBMCs activated by anti-CD3/anti-CD28 co-stimulation were used as a positive control. At 4 hours and 16 hours post-infection, supernatant was harvested, and analyzed for the concentration of IFN-γ, IL-10, IL-12p70, IL-2, IL-4, and TNFα using MesoScale Discovery (MSD) U-Plex 6-assay 96-Well SECTOR plates. FIG. 12A illustrates the mean (+/−SD) concentrations of the cytokines in supernatant at 4 hours post-infection, while FIG. 12B illustrates the mean (+/−SD) concentrations of the cytokines in supernatant at 16 hours post-infection. Where no bar is present, this indicates the cytokine level was below the limit of detection for the assay.

The results demonstrate that the vMyx-Triple virus elicits production of cytokines by human PBMCs, including IL-12 and TNFα. The levels of IL-12 observed in response to infection with vMyx-Triple were higher than levels observed for any of the other viruses. Additionally, higher levels of IFN-γ were observed in response to the vMyx-Triple virus, particularly at 4 hours post-infection.

Example 10—Anti-Cancer Activity of vMyx-Triple in Human Xenograft Tumor Models

The ability of vMYX Triple to inhibit growth of human tumors in vivo was tested in xenograft models. The human cancer cell lines NCI-H1971 (lung cancer), A673 (sarcoma), and SJSA-1 (sarcoma) were implanted with 5 million tumor cells per mouse subcutaneously into the flanks of immuno-deficient mice (athymic nude mice for NCI-H1975 and SJSA-1, CD17.SCID mice for A673). Tumor bearing animals were randomized into treatment groups of 7-8 animals per group with an average tumor volume of 100-150 mm$^3$. Animals were treated with intratumoral injection of vMyx-Triple at doses of $1\times10^7$ focus forming units (FFU) or $2\times10^7$ FFU. Doses were administered once per week (QW), once every 4 days (Q4D), or once every two days (Q2D). Tumor volume and body weight were measured three times per week.

Figure 13A:
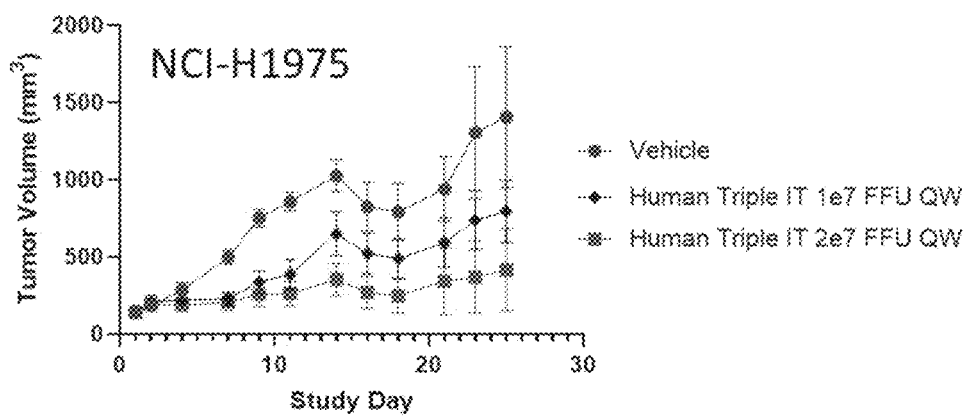
FIG. 13A plots the volume of NCI-H1971 (lung cancer) xenograft tumors over time in immunodeficient mice that were treated with the indicated doses of vMyx—Triple once per week (QW).

FIG. 13A plots the volume of NCI-H1971 (lung cancer) xenograft tumors over time, showing that intra-tumoral injection of vMYX Triple inhibits tumor growth in a dose-dependent manner in this model.

Figure 13B:
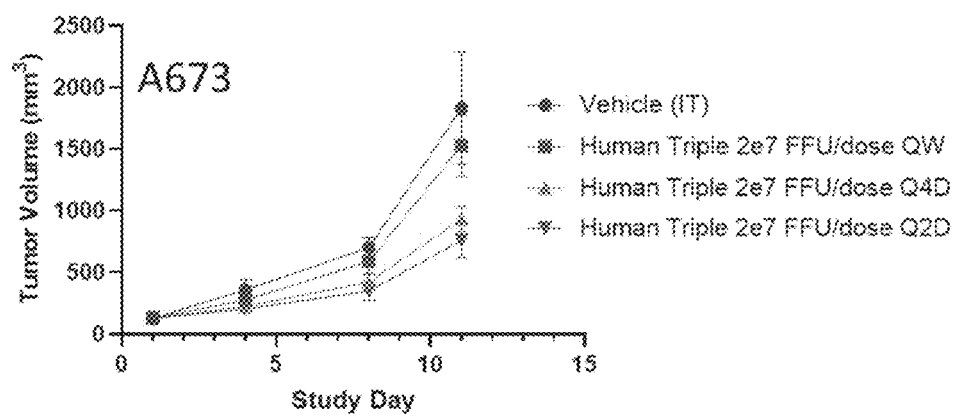
FIG. 13B plots the volume of A673 (sarcoma) xenograft tumors over time in immunodeficient mice that were treated with the indicated doses of vMyx—Triple once per week (QW), every 4 days (Q4D), or every 2 days (Q2D).

FIG. 13B plots the volume of A673 (sarcoma) xenograft tumors over time, showing that administering vMYX Triple more frequently results in greater inhibition of tumor growth in this model.

Figure 13C:
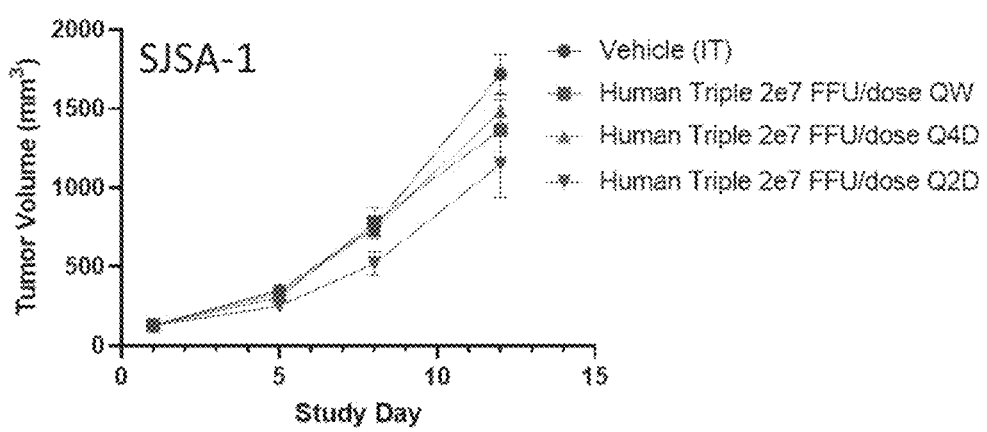
FIG. 13C plots the volume of SJSA (sarcoma) xenograft tumors over time in immunodeficient mice that were treated with the indicated doses of vMyx—Triple once per week (QW, every 4 days (Q4D), or every 2 days (Q2D).

FIG. 13C plots the volume of SJSA-1 (sarcoma) xenograft tumors over time, showing that administering vMYX Triple more frequently results in greater inhibition of tumor growth in this model.

These results demonstrate that vMYX-Triple can inhibit growth of human tumors in vivo, even in the context of an immunodeficient host.

Example 11—IL-12 and TNFα Production in Human Xenograft Tumor Models

The ability of vMYX Triple to elicit IL-12 and TNFα production in vivo was tested in xenograft models. The human sarcoma cancer cell lines SJSA-1 and A673 were implanted subcutaneously into the flanks of immunodeficient mice (athymic nude mice for SJSA-1, CD17.SCID mice for A673). Tumor bearing animals were treated via intratumoral (IT) or intravenous (IV) injection of $2 \times 10^7$ FFU of vMYX Triple on day 1 post-implant (n=3 animals per group). Serum samples were collected 4 and 24 hours post-treatment. Tumors were collected at 24 hours post treatment and processed for cytokine measurement. Cytokine analysis was performed using MesoScale Discovery (MSD) U-Plex 6-assay 96-Well SECTOR plates.

Figure 14A:
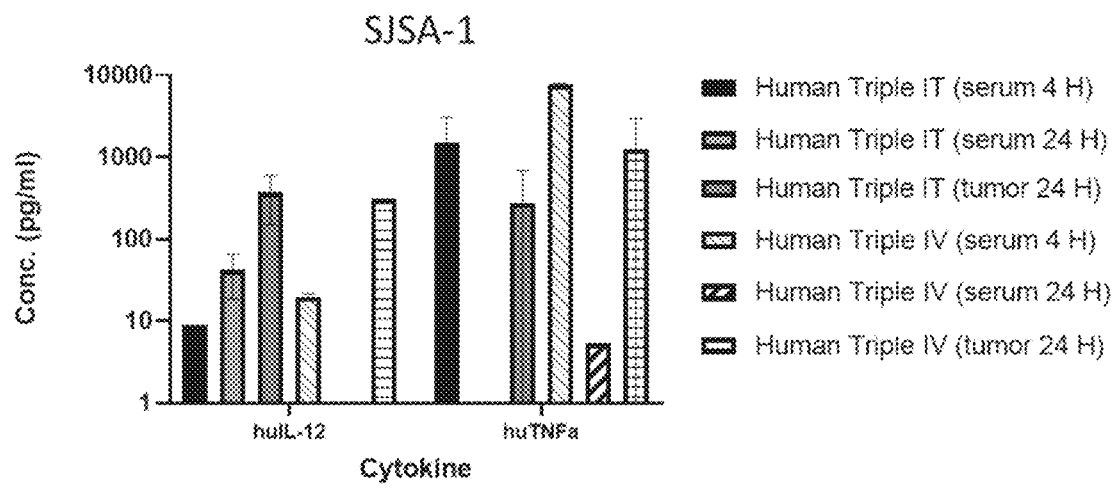
FIG. 14A shows the concentrations of IL-12 and TNF-α detected in serum and tumor tissue from immunodeficient mice bearing SJSA-1 tumors. The mice were treated with vMyx-Triple via the intravenous (IV) or intra-tumoral (IT) routes, and samples collected at 4 hours (4H) or 24 hours (24H) post-treatment. Mean±SD is plotted. When no bar is present, the level of the analyte was below the limit of detection for the assay.

FIG. 14A shows the concentrations of IL-12 and TNFα detected in serum at 4 and 24 hours post-treatment, and in tumors at 24 hours post-treatment, in animals bearing SJSA-1 tumors. Mean±SD is plotted. When no bar is present, the level of the analyte was below the limit of detection for the assay.

Figure 14B:
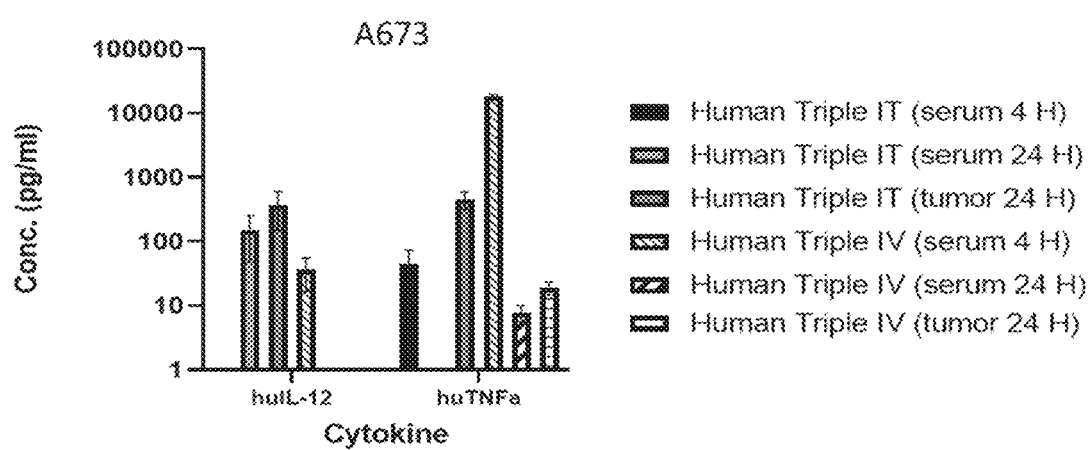
FIG. 14B shows the concentrations of IL-12 and TNF-α detected in serum and tumor tissue from immunodeficient mice bearing A673 tumors. The mice were treated with vMyx Triple via the intravenous (IV) or intra-tumoral (IT) routes, and samples collected at 4 hours (4H) or 24 hours (24H) post-treatment. Mean±SD is plotted. When no bar is present, the level of the analyte was below the limit of detection for the assay.

FIG. 14B shows the concentrations of IL-12 and TNFα detected in serum at 4 and 24 hours post-treatment, and in tumors at 24 hours post-treatment, in animals bearing A673 tumors. Mean±SD is plotted. When no bar is present, the level of the analyte was below the limit of detection for the assay.

The results demonstrate that intravenous and intra-tumor treatment with vMYX Triple can elicit IL-12 and TNFα production within tumors, as well as increasing levels of the cytokines in circulation.

Example 12—Anti-Tumor Efficacy of M153KO MYXV In Vivo

This example compared the degree of tumor growth inhibition achieved by a MYXV with the M153 gene knocked out versus a MYXV that expresses a wild type M153. Both MYXV viruses contained transgenes for expression of TNF inserted in between the M135 and M136 region.

B16-F10 mouse melanoma cells were implanted into C57BL/6 mice. Tumor bearing animals were randomized into treatment groups of 8 animals per group with an average tumor volume of 75-100 mm³. Animals were treated via intratumoral injection of the indicated myxoma virus at $2 \times 10^7$ FFU/dose on day 1 and day 8 post-randomization.

Figure 15:
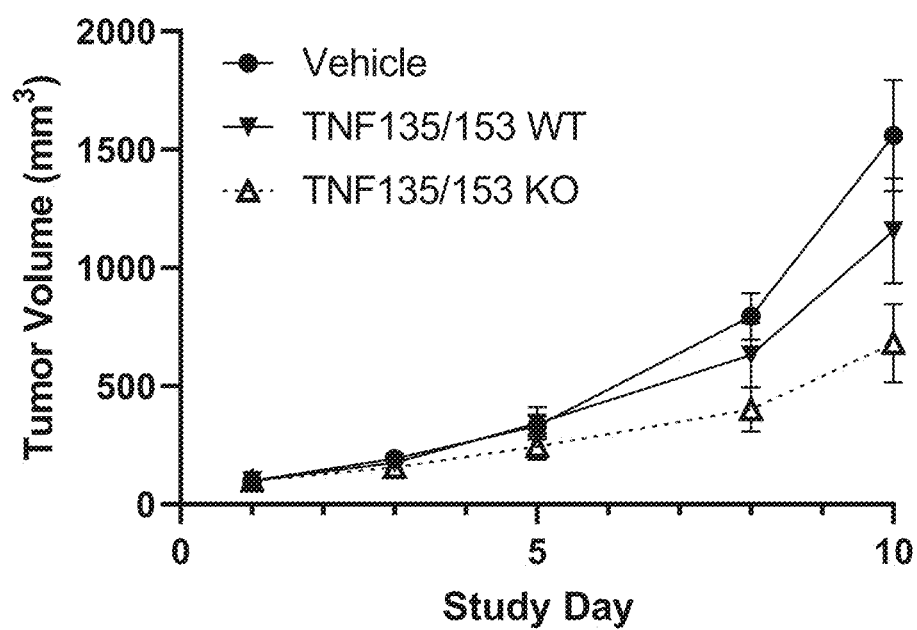
FIG. 15 plots tumor volume over time for C57BL/6 mice implanted with B16-F10 mouse melanoma cells, and treated with TNF-expressing MYXV that had M153 and M135 knocked out (TNF135/153 KO) or TNF-expressing MYXV with wild type copies of both genes (TNF135/153 WT).

FIG. 15 plots tumor volume over time, and shows that the virus with M153 knocked out inhibited tumor growth to a greater extent than the virus that expresses wild type M153.

Example 13—Anti-Tumor Efficacy of vMYX Mouse Triple in an MC38 Cancer Model

The anti-cancer efficacy of vMyx-Triple was evaluated in an MC38 mouse model. C57BL/6 mice were implanted with MC38 mouse colorectal cancer cells. Tumor-bearing animals were randomized into treatment groups of 8 animals per group with an average tumor volume of 75-100 mm³. Animals were treated via intratumoral (IT) injection of $2 \times 10^7$ FFU/dose once every 4 days for four doses with the indicated myxoma virus.

msTriple low refers to a vMyx-Triple that expresses murine rather than human IL-12, at a relatively low level. msTriple high refers to a vMyx-Triple that expresses murine rather than human IL-12, at a relatively higher level (as a single polypeptide with an elastin linker joining the IL-12 subunits). The msTriple viruses also express human Decorin and TNF, and have the M153 gene knocked out. GFP refers to vMyx-GFP, which does not encode any of the cytokines, and contains an intact wild type M153 gene.

Figure 16A:
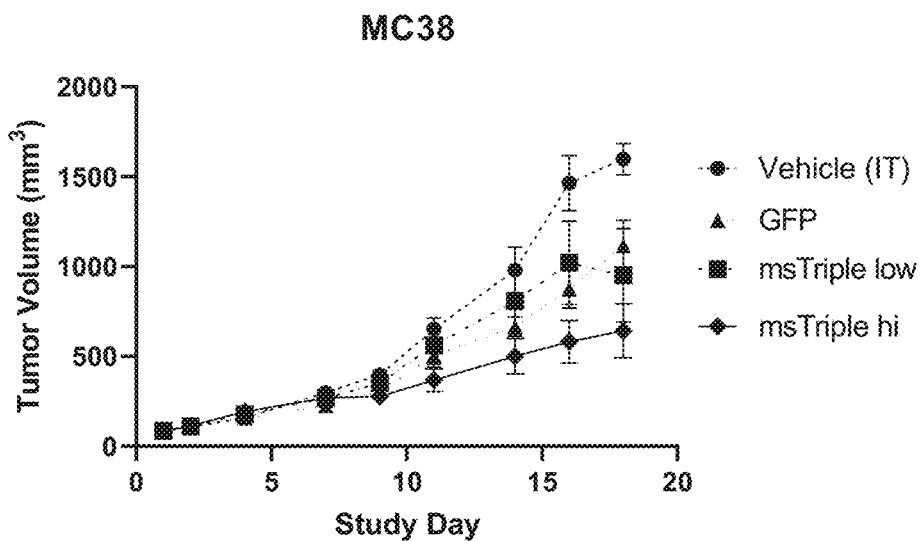
FIG. 16A and FIG. 16B plot tumor volume and survival over time for C57BL/6 mice implanted with MC38 mouse colorectal cancer cells. Animals were treated via intratumoral (IT) injection of $2\times10^7$ FFU/dose once every 4 days for four doses with the indicated myxoma virus. msTriple low refers to a vMyx-Triple that expresses murine rather than human IL-12, at a relatively low level. msTriple high refers to a vMyx-Triple that expresses murine IL-12 at a relatively higher level. The msTriple viruses also express human Decorin and TNF, and have the M153 gene knocked out. GFP refers to vMyx-GFP, which does not encode any of the cytokines, and contains an intact M153 gene. Tumor volume measurements were recorded three times per week, and are plotted in FIG. 16A. Survival is plotted in FIG. 16B.
Figure 16B:
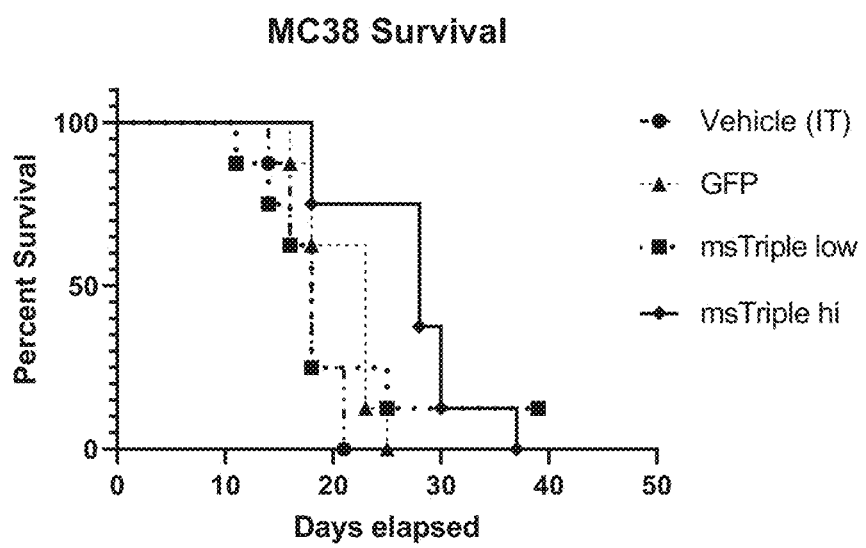

Tumor volume measurements were recorded three times per week, and are plotted in FIG. 16A. Survival is plotted in FIG. 16B. Survival endpoints were met when tumor volume was ≥1500 mm³ (for an individual animal), or when the animal met IACUC guidelines for terminal sacrifice.

These results show that MYXV can inhibit tumor growth in vivo, and that the MYXV that expresses higher levels of mouse IL-12 exhibits greater inhibition of tumor growth in this model.

Example 14—Anti-Tumor Efficacy of vMYX Mouse Triple in a B16-F10 Cancer Model

The anti-cancer efficacy of vMyx-Triple that expresses mouse IL-12 was evaluated in a B16-F10 mouse model. C57BL/6 mice were implanted with B16-F10 mouse melanoma cells. Tumor bearing animals were randomized into treatment groups of 8 animals per group with an average tumor volume of 75-100 mm³. Animals were treated via intratumoral injection of $2 \times 10^7$ FFU/dose on Day 1 and Day 8 with the indicated myxoma virus.

msTriple low refers to a vMyx-Triple that expresses murine rather than human IL-12, at a relatively low level. msTriple high refers to a vMyx-Triple that expresses murine rather than human IL-12, at a relatively higher level (as a single polypeptide with an elastin linker joining the IL-12 subunits). The msTriple viruses also express human Decorin and TNF, and have the M153 gene knocked out. GFP refers to vMyx-GFP, which does not encode any of the cytokines, and contains an intact M153 gene.

Figure 17A:
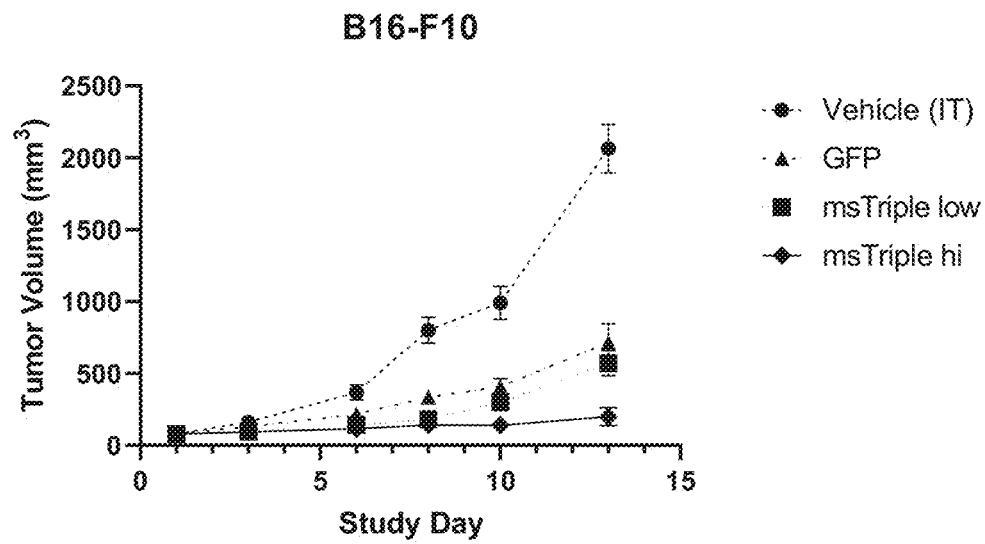
FIG. 17A and FIG. 17B plot tumor volume and survival over time for C57BL/6 mice implanted with B16-F10 mouse melanoma cells. Animals were treated via intratumoral injection of $2\times10^7$ FFU/dose on Day 1 and Day 8 with the indicated myxoma virus. msTriple low refers to a vMyx-Triple that expresses murine rather than human IL-12, at a relatively low level. msTriple high refers to a vMyx-Triple that expresses murine IL-12 at a relatively higher level. The msTriple viruses also express human Decorin and TNF, and have the M153 gene knocked out. GFP refers to vMyx-GFP, which does not encode any of the cytokines, and contains an intact M153 gene. Tumor volume measurements were recorded three times per week, and are plotted in FIG. 17A. Survival is plotted in FIG. 17B.
Figure 17B:
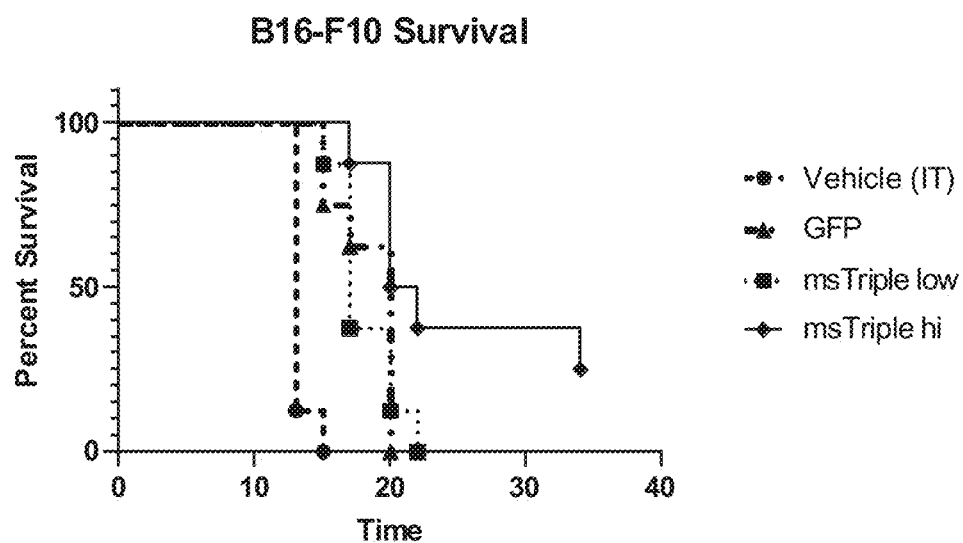

Tumor volume measurements were recorded three times per week, and are plotted in 17A. Survival is plotted in FIG. 17B. Survival endpoints were met when tumor volume was≥1500 mm³ (for an individual animal), or when the animal met IACUC guidelines for terminal sacrifice.

The results show that MYXV can inhibit tumor growth in vivo and enhance survival. The MYXV that expresses higher levels of mouse IL-12 exhibited greater inhibition of tumor growth in this model, and conferred a greater survival benefit compared to the other two myxoma viruses.

Example 15—vMYX Mouse Triple as a Cancer Therapy by Intravenous Versus Intratumoral Routes of Administration The anti-tumor efficacy of vMyx mouse Triple was evaluated in mouse syngeneic cancer models, with comparison of intravenous and intratumoral routes of administration. C57BL/6 mice were implanted subcutaneously with B16-F10 melanoma cells, and Balb/c mice were implanted subcutaneously with CT26 colorectal cancer cells. Tumor bearing animals were randomized into treatment groups of 8 animals per group with an average tumor volume of 75-100 mm³. Animals were treated via intratumoral (IT) or intravenous (IV) injection msTriple high, a MYXV that expresses a relatively high level of murine IL-12 (as a single polypeptide with an elastin linker joining the IL-12 subunits). msTriple high also express human Decorin and TNF, and has the M153 gene knocked out. Four doses of 2×10⁷ focus forming units (FFU) or 1×10⁸ FFU were administered to each mouse, with doses administered every four days. Tumor volume measurements were recorded three times per week.

Figure 18A:
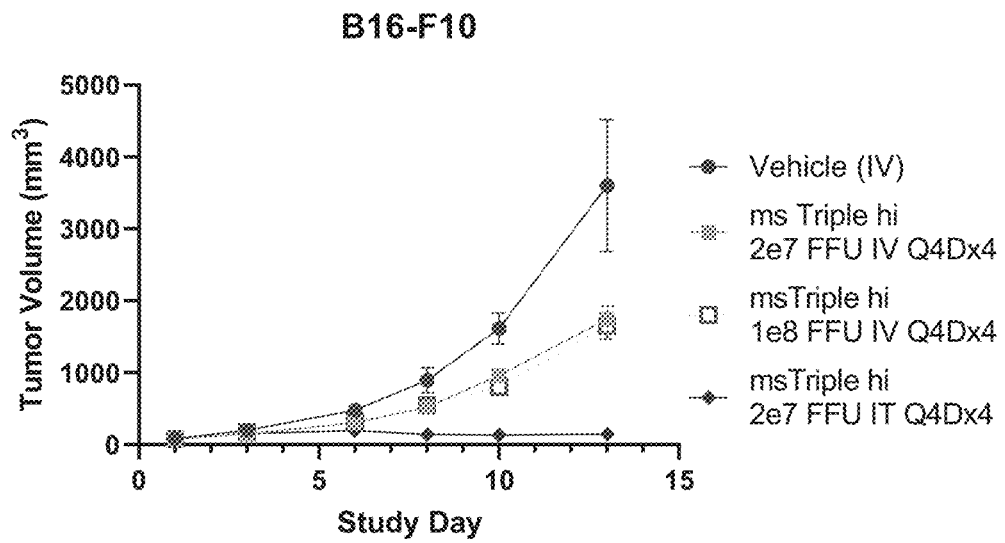
FIG. 18A plots tumor volume over time for C57BL/6 mice implanted with B16-F10 mouse melanoma cells, and treated with the indicated doses of msTriple high, a MYXV that expresses a relatively high level of murine IL-12, also expresses human Decorin and human TNF, and has the M153 gene knocked out. The virus was administered intratumorally (IT) or intravenously (IV).

FIG. 18A shows tumor volumes of the C57BL/6 mice with B16-F10 tumors.

Figure 18B:
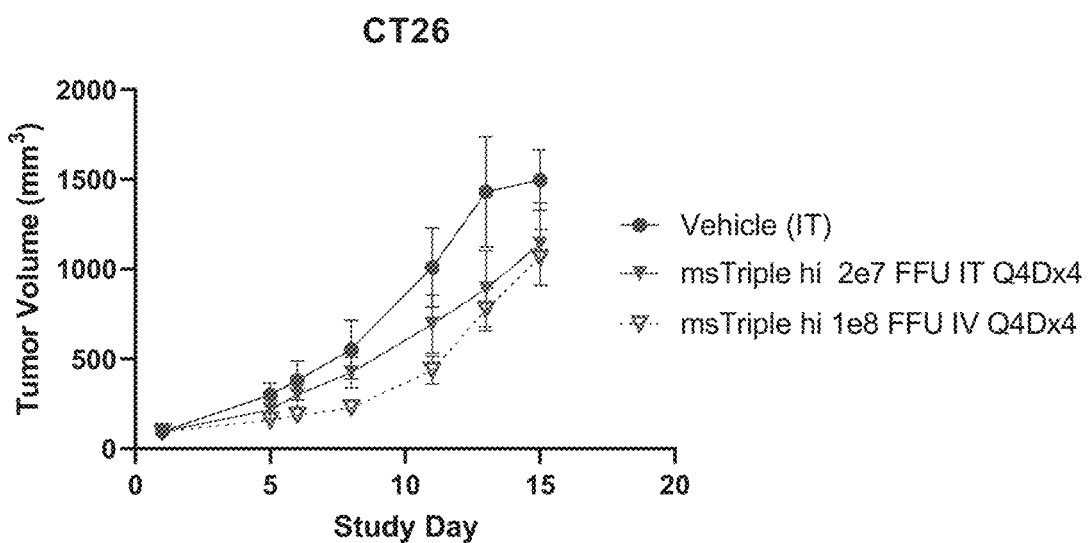
FIG. 18B plots tumor volume over time for Balb/c mice implanted with CT26 mouse colorectal cancer cells, and treated with the indicated doses of msTriple high. The virus was administered intratumorally (IT) or intravenously (IV).

FIG. 18B shows tumor volumes of the Balb/c mice with CT26 tumors.

msTriple high inhibited tumor growth at all doses and routes of administration tested compared to vehicle control. In the B16-F10 model, intra-tumoral injection of 2×10⁷ FFU per dose exhibited greater inhibition of tumor growth than intravenous administration at either 1×10⁸ or 2×10⁷ FFU per dose.

Example 16—vMYX Mouse Triple Plus Immune Checkpoint Inhibitor Combination Therapy Balb/c mice were implanted with K7M2 sarcoma cells via intravenous injection into the tail vein. Starting on day 3 post tumor inoculation, animals (n=10 per group) were treated via injection into the retro-orbital sinus of 2×10⁷ FFU/dose of the vMyx-mouse Triple (low IL-12). This myxoma virus expresses human Decorin, human TNF, and a relatively low level of mouse IL-12. vMyx-mouse Triple (low IL-12) also has the M153 gene knocked out. The virus was administered once every four days for four doses. Some groups were injected intraperitoneally with anti-PD-1 or anti-PD-L1 antibodies at 10 mg/kg, once every four days for four doses.

Figure 19:
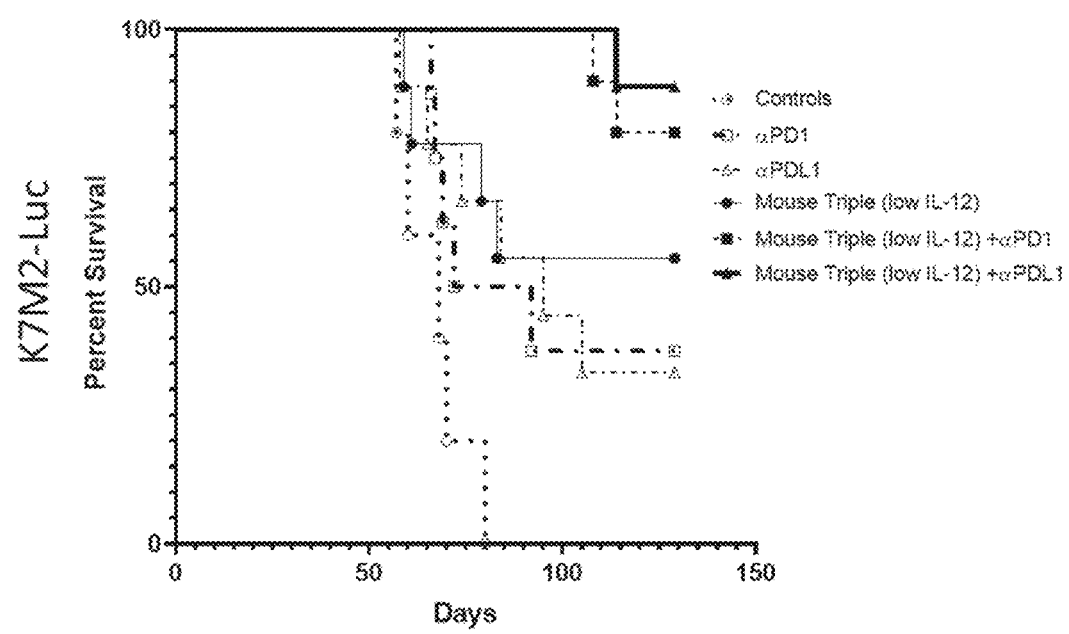
FIG. 19 displays survival curves of Balb/c mice implanted with K7M2 sarcoma cells. Groups of mice were treated via injection into the retro-orbital sinus of $2\times10^7$ FFU/dose of the vMyx-mouse Triple (low IL-12), and/or with intraperitoneal injections of anti-PD-1 or anti-PD-L1 antibodies at 10 mg/kg.

FIG. 19 displays survival curves the groups. All animals in the untreated control group had succumbed to infection by approximately day 80 post-implant. At day 130 post-implant, approximately 30-40% of animals that received anti-PD-1 or anti-PD-L1 had survived, over 50% of animals treated with vMyx-mouse Triple (low IL-12) had survived, and animals treated with a combination of vMyx-mouse Triple (low IL-12) and either anti-PD-1 or anti-PD-L1 exhibited the highest survival, with more than about 80% alive.

These data show that myxoma viruses of the disclosure can improve survival of subjects with cancer, and that combination therapy with immune checkpoint inhibitors can improve survival further still.

In a separate experiment, C57BL/6 mice were implanted with MC38 mouse colorectal cancer cells subcutaneously on the flank. Tumor bearing animals were randomized into treatment groups of 8 animals per group with an average tumor volume of 75-100 mm³.

Animals were treated via intratumoral injection of 2×10⁷ FFU/dose on day 1 and day 8 post-randomization with vMyx-mouse Triple (low IL-12). Some groups were injected intraperitoneally with anti-PD-1 antibody at 10 mg/kg, once every four days for four doses. Tumor volume and body weight was measured three times per week.

Figure 20A:
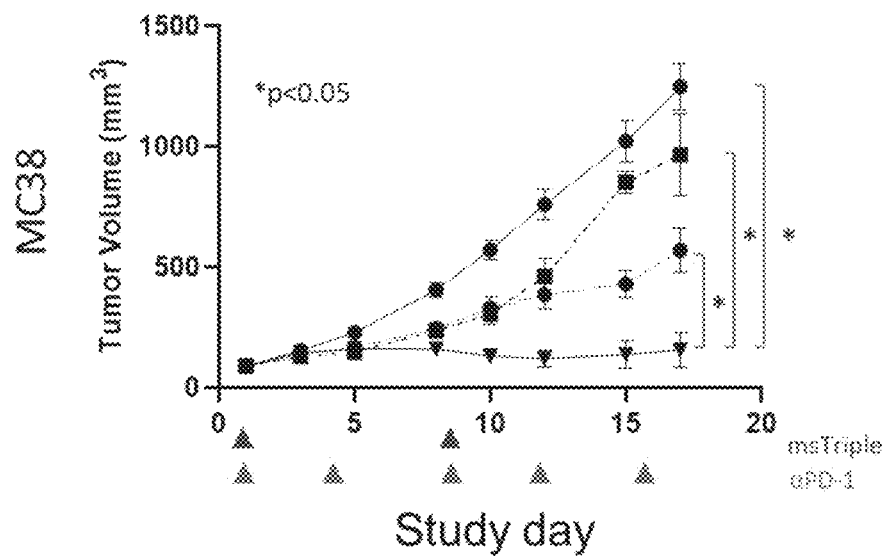
FIG. 20A plots tumor volume overtime of C57BL/6 mice implanted with MC38 mouse colorectal cancer cells. Groups of animals were treated via intratumoral injection of $2\times10^7$ FFU/dose of vMyx-mouse Triple (low IL-12) on day 1 and day 8 post-randomization, and/or with anti-PD-1 antibody at 10 mg/kg, once every four days for four doses. Circles connected by solid lines: vehicle-treated; squares: vMyx-mouse Triple alone; circles with dashed line; anti-PD-1; triangles: combination of vMyx-mouse Triple and anti-PD-1.

FIG. 20A plots tumor volume over time. Tumor volume for vehicle-treated control mice is shown by circles connected by solid lines. Mice treated with vMyx-mouse Triple alone (squares) exhibited reduced tumor volume and delayed tumor growth compared to vehicle-treated controls, as did mice treated with anti-PD-1 alone (circles with dashed line). The greatest inhibition of tumor growth was observed in the group that received both vMyx-mouse Triple and anti-PD-1 (triangles).

Figure 20B:
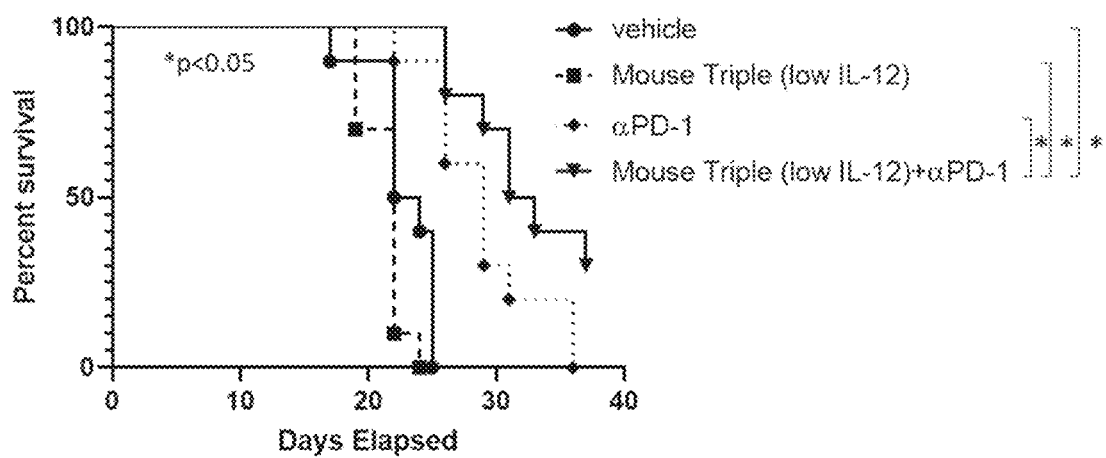
FIG. 20B plots survival of the groups in FIG. 20A.

FIG. 20B shows survival curves for the groups. Similar to tumor volume, the group that received both vMyx-mouse Triple and anti-PD-1 exhibited the best survival profile.

These data show that myxoma viruses of the disclosure can inhibit tumor growth and enhance survival of subjects with cancer, and that combination therapy with an immune checkpoint inhibitors can have a synergistic effect.

ADDITIONAL SEQUENCES

Exemplary sequences corresponding to the compositions and methods described herein are shown in Table 5.

TABLE 5

| SEQ ID NO | Name | Sequence |
| --- | --- | --- |
| 11 | Synthetic early/late promoter | TTAAAAATTGAAATTTTATTTTTTTTTTTGGAATATAAATA |
| 54 | Synthetic early/late promoter | AAAAATTGAAATTTTATTTTTTTTTTTGGAATATAAATA |
| 12 | hTNFa | ATGAGCACTGAAAGCATGATCCGGGACGTGGAGCTGGCCGAGGAGGCG<br>CTCCCCAAGAAGACAGGGGGGCCCCAGGGCTCCAGGCGGTGCTTGTTC<br>CTCAGCCTCTTCTCCTTCCTGATCGTGGCAGGCGCCACCACGCTCTTC<br>TGCCTGCTGCACTTTGGAGTGATCGGCCCCCAGAGGGAAGAGTTCCCC<br>AGGGACCTCTCTCTAATCAGCCCTCTGGCCCAGGCAGTCAGATCATCT<br>TCTCGAACCCCGAGTGACAAGCCTGTAGCCCATGTTGTAGCAAACCCT<br>CAAGCTGAGGGGCAGCTCCAGTGGCTGAACCGCCGGGCCAATGCCCTC<br>CTGGCCAATGGCGTGGAGCTGAGAGATAACCAGCTGGTGGTGCCATCA<br>GAGGGCCTGTACCTCATCTACTCCCAGGTCCTCTTCAAGGGCCAAGGC<br>TGCCCCTCCACCCATGTGCTCCTCACCCACACCATCAGCCGCATCGCC<br>GTCTCCTACCAGACCAAGGTCAACCTCCTCTCTGCCATCAAGAGCCCC<br>TGCCAGAGGGAGACCCCAGAGGGGGCTGAGGCCAAGCCCTGGTATGAG<br>CCCATCTATCTGGGAGGGGTCTTCCAGCTGGAGAAGGGTGACCGACTC<br>AGCGCTGAGATCAATCGGCCCGACTATCTCGACTTTGCCGAGTCTGGG<br>CAGGTCTACTTTGGGATCATTGCCCTGTGA |
| 13 | GFP | ATGGTGAGCAAGGGCGAGGAGCTGTTCACCGGGGTGGTGCCCATCCTG<br>GTCGAGCTGGACGGCGACGTAAACGGCCACAAGTTCAGCGTGTCCGGC<br>GAGGGCGAGGGCGATGCCACCTACGGCAAGCTGACCCTGAAGTTCATC<br>TGCACCACCGGCAAGCTGCCCGTGCCCTGGCCCACCCTCGTGACCACC |

TABLE 5-continued

| SEQ ID NO | Name | Sequence |
|---|---|---|
| | | CTGACCTACGGCGTGCAGTGCTTCAGCCGCTACCCCGACCACATGAAG<br>CAGCACGACTTCTTCAAGTCCGCCATGCCCGAAGGCTACGTCCAGGAG<br>CGCACCATCTTCTTCAAGGACGACGGCAACTACAAGACCCGCGCCGAG<br>GTGAAGTTCGAGGGCGACACCCTGGTGAACCGCATCGAGCTGAAGGGC<br>ATCGACTTCAAGGAGGACGGCAACATCCTGGGGCACAAGCTGGAGTAC<br>AACTACAACAGCCACAACGTCTATATCATGGCCGACAAGCAGAAGAAC<br>GGCATCAAGGTGAACTTCAAGATCCGCCACAACATCGAGGACGGCAGC<br>GTGCAGCTCGCCGACCACTACCAGCAGAACACCCCCATCGGCGACGGC<br>CCCGTGCTGCTGCCCGACAACCACTACCTGAGCACCCAGTCCGCCCTG<br>AGCAAAGACCCCAACGAGAAGCGCGATCACATGGTCCTGCTGGAGTTC<br>GTGACCGCCGCCGGGATCACTCTCGGCATGGACGAGCTGTACAAGTAA |
| 14 | Human Decorin,<br>isoform A | MKATIILLLLAQVSWAGPFQQRGLFDFMLEDEASGIGPEVPDDRDFEP<br>SLGPVCPFRCQCHLRVVQCSDLGLDKVPKDLPPDTTLLDLQNNKITEI<br>KDGDFKNLKNLHALILVNNKISKVSPGAFTPLVKLERLYLSKNQLKEL<br>PEKMPKTLQELRAHENEITKVRKVTFNGLNQMIVIELGTNPLKSSGIE<br>NGAFQGMKKLSYIRIADTNITSIPQGLPPSLTELHLDGNKISRVDAAS<br>LKGLNNLAKLGLSFNSISAVDNGSLANTPHLRELHLDNNKLTRVPGGL<br>AEHKYIQVVYLHNNNISVVGSSDFCPPGHNTKKASYSGVSLFSNPVQY<br>WEIQPSTFRCVYVRSAIQLGNYK |
| 15 | Human Decorin,<br>isoform B | MKATIILLLLAQVSWAGPFQQRGLFDFMLEDEASGIGPEVPDDRDFEP<br>SLGPVCPFRCQCHLRVVQCSDLELGTNPLKSSGIENGAFQGMKKLSYI<br>RIADTNITSIPQGLPPSLTELHLDGNKISRVDAASLKGLNNLAKLGLS<br>FNSISAVDNGSLANTPHLRELHLDNNKLTRVPGGLAEHKYIQVVYLHN<br>NNISVVGSSDFCPPGHNTKKASYSGVSLFSNPVQYWEIQPSTFRCVYV<br>RSAIQLGNYK |
| 16 | Human Decorin,<br>isoform C | MKATIILLLLAQVSWAGPFQQRGLFDFMLEDEASGIGPEVPDDRDFEP<br>SLGPVCPFRCQCHLRVVQCSDLGLPPSLTELHLDGNKISRVDAASLKG<br>LNNLAKLGLSFNSISAVDNGSLANTPHLRELHLDNNKLTRVPGGLAEH<br>KYIQVVYLHNNNISVVGSSDFCPPGHNTKKASYSGVSLFSNPVQYWEI<br>QPSTFRCVYVRSAIQLGNYK |
| 17 | Huma Decorin,<br>isoform D | MKATIILLLLAQVSWAGPFQQRGLFDFMLEDEASGIGPEVPDDRDFEP<br>SLGPVCPFRCQCHLRVVQCSDLGLDKVPKDLPPDTTLLDLQNNKITEI<br>KDGDFKNLKNLHVVYLHNNNISVVGSSDFCPPGHNTKKASYSGVSLFS<br>NPVQYWEIQPSTFRCVYVRSAIQLGNYK |
| 18 | Human Decorin,<br>isoform E | MKATIILLLLAQVSWAGPFQQRGLFDFMLEDEASGIGPEVPDDRDFEP<br>SLGPVCPFRCQCHLRVVQCSDLGCLPS |
| 19 | Mouse Decorin | MKATLIFFLLAQVSWAGPFEQRGLFDFMLEDEASGIIPYDPDNPLISM<br>CPYRCQCHLRVVQCSDLGLDKVPWDFPPDTTLLDLQNNKITEKEGAF<br>KNLKDLHTLILVNNKISKISPEAFKPLVKLERLYLSKNQLKELPEKMP<br>RTLQELRVHENEITKLRKSDFNGLNNVLVIELGGNPLKNSGIENGAFQ<br>GLKSLSYIRISDTNITAIPQGLPTSLTEVHLDGNKITKVDAPSLKGLI<br>NLSKLGLSFNSITVMENGSLANVPHLRELHLDNNKLLRVPAGLAQHKY<br>IQVVYLHNNNISAVGQNDFCRAGHPSRKASYSAVSLYGNPVRYWEIFP<br>NTFRCVYVRSAIQLGNYK |
| 20 | P11 (promoter) | GAATTTCATTTTGTTTTTTCTATGCTATAA |
| 21 | IRES (ECMV) | TATGCTAGTACGTCTCTCAAGGATAAGTAAGTAATATTAAGGTACGGG<br>AGGTATTGGACAGGCCGCAATAAAATATCTTTATTTTCATTACATCTG<br>TGTGTTGGTTTTTTGTGTGAATCGATAGTACTAACATACGCTCTCCAT<br>CAAAACAAAACGAAACAAAACAAACTAGCAAAATAGGCTGTCCCCAGT<br>GCAAGTGCAGGTGCCAGAACATTTCTCTGGCCTAACTGGCCGGTACCT<br>GAGCTCTAGTTTCACTTTCCCTAGTTTCACTTTCCCTAGTTTCACTTT<br>CCCTAGTTTCACTTTCCCTAGTTTCACTTTCCCCTCGAGGATATCAAG<br>ATCTGGCCTCGGCGGCCAG |
| 22 | huIL-12 A (p35) | ATGTGGCCCCCTGGGTCAGCCTCCCAGCCACCGCCCTCACCTGCCGCG<br>GCCACAGGTCTGCATCCAGCGGCTCGCCCTGTGTCCCTGCAGTGCCGG<br>CTCAGCATGTGTCCAGCGCGCAGCCTCCTCCTTGTGGCTACCCTGGTC<br>CTCCTGGACCACCTCAGTTTGGCCAGAAACCTCCCCGTGGCCACTCCA<br>GACCCAGGAATGTTCCCATGCCTTCACCACTCCCAAAACCTGCTGAGG<br>GCCGTCAGCAACATGCTCCAGAAGGCCAGACAAACTCTAGAATTTTAC<br>CCTTGCACTTCTGAAGAGATTGATCATGAAGATATCACAAAAGATAAA<br>ACCAGCACAGTGGAGGCCTGTTTACCATTGGAATTAACCAAGAATGAG<br>AGTTGCCTAAATTCCAGAGAGACCTCTTTTCATAACTAATGGGAGTTGC<br>CTGGCCTCCAGAAAGACCTCTTTTATGATGGCCCTGTGCCTTAGTAGT<br>ATTTATGAAGACTTGAAGATGTACCAGGTGGAGTTCAAGACCATGAAT<br>GCAAAGCTTCTGATGGATCCTAAGAGGCAGATCTTTCTAGATCAAAAC<br>ATGCTGGCAGTTATTGATGAGCTGATGCAGGCCCTGAATTTCAACAGT<br>GAGACTGTGCCACAAAAATCCTCCCTTGAAGAACCGGATTTTTATAAA<br>ACTAAAATCAAGCTCTGCATACTTCTTCATGCTTTCAGAATTCGGGCA<br>GTGACTATTGATAGAGTGATGAGCTATCTGAATGCTTCCTAA |

TABLE 5-continued

| SEQ ID NO | Name | Sequence |
|---|---|---|
| 23 | dsRed | ATGGTGCGCTCCTCCAAGAACGTCATCAAGGAGTTCATGCGCTTCAAG<br>GTGCGCATGGAGGGCACCGTGAACGGCCACGAGTTCGAGATCGAGGGC<br>GAGGGCGAGGGCCGCCCCTACGAGGGCCACAACACCGTGAAGCTGAAG<br>GTGACCAAGGGCGGCCCCCTGCCCTTCGCCTGGGACATCCTGTCCCCC<br>CAGTTCCAGTACGGCTCCAAGGTGTACGTGAAGCACCCCGCCGACATC<br>CCCGACTACAAGAAGCTGTCCTTCCCCGAGGGCTTCAAGTGGGAGCGC<br>GTGATGAACTTCGAGGACGGCGGCGTGGTGACCGTGACCCAGGACTCC<br>TCCCTGCAGGACGGCTGCTTCATCTACAAGGTGAAGTTCATCGGCGTG<br>AACTTCCCCTCCGACGGCCCCGTAATGCAGAAGAAGACCATGGGCTGG<br>GAGGCCTCCACCGAGCGCCTGTACCCCCGCGACGGCGTGCTGAAGGGC<br>GAGATCCACAAGGCCCTGAAGCTGAAGGACGGCGGCCACTACCTGGTG<br>GAGTTCAAGTCCATCTACATGGCCAAGAAGCCCGTGCAGCTGCCCGGC<br>TACTACTACGTGGACTCCAAGCTGGACATCACCTCCCACAACGAGGAC<br>TACACCATCGTGGAGCAGTACGAGCGCACCGAGGGCCGCCACCACCTG<br>TTCCTGTAG |
| 24 | Hu TNF-a | ATGAGCACTGAAAGCATGATCCGGGACGTGGAGCTGGCCGAGGAGGCG<br>CTCCCCAAGAGGACAGGGGGGCCCCAGGGCTCCAGGCGGTGCTTGTTC<br>CTCAGCCTCTTCTCCTTCCTGATCGTGGCAGGCGCCACCACGCTCTTC<br>TGCCTGCTGCACTTTGGAGTGATCGGCCCCCAGAGGGAAGAGTTCCCC<br>AGGGACCTCTCTCTAATCAGCCCTCTGGCCCAGGCAGTCAGATCATCT<br>TCTCGAACCCCGAGTGACAAGCCTGTAGCCCATGTTGTAGCAAACCCT<br>CAAGCTGAGGGGCAGCTCCAGTGGCTGAACCGCCGGGCCAATGCCCTC<br>CTGGCCAATGGCGTGGAGCTGAGAGATAACCAGCTGGTGGTGCCATCA<br>GAGGGCCTGTACCTCATCTACTCCCAGGTCCTCTTCAAGGGCCAAGGC<br>TGCCCCTCCACCCATGTGCTCCTCACCCACACCATCAGCCGCATCGCC<br>GTCTCCTACCAGACCAAGGTCAACCTCCTCTCTGCCATCAAGAGCCCC<br>TGCCAGAGGGAGACCCCAGAGGGGGCTGAGGCCAAGCCCTGGTATGAG<br>CCCATCTATCTGGGAGGGGTCTTCCAGCTGGAGAAGGGTGACCGACTC<br>AGCGCTGAGATCAATCGGCCCGACTATCTCGACTTTGCCGAGTCTGGG<br>CAGGTCTACTTTGGGATCATTGCCCTGTGA |
| 25 | Hu Decorin | ATGAAGGCCACTATCATCCTCCTTCTGCTTGCACAAGTTTCCTGGGCT<br>GGACCGTTTCAACAGAGAGGCTTATTTGACTTTATGCTAGAAGATGAG<br>GCTTCTGGGATAGGCCCAGAAGTTCCTGATGACCGCGACTTCGAGCCC<br>TCCCTAGGCCCAGTGTGCCCCTTCCGCTGTCAATGCCATCTTCGAGTG<br>GTCCAGTGTTCTGATTTGGGTCTGGACAAAGTGCCAAAGGATCTTCCC<br>CCTGACACAACTCTGCTAGACCTGCAAAACAACAAAATAACCGAAATC<br>AAAGATGGAGACTTTAAGAACCTGAAGAACCTTCACGCATTGATTCTT<br>GTCAACAATAAAATTAGCAAAGTTAGTCCTGGAGCATTTACACCTTTG<br>GTGAAGTTGGAACGACTTTATCTGTCCAAGAATCAGCTGAAGGAATTG<br>CCAGAAAAAATGCCCAAAACTCTTCAGGAGCTGCGTGCCCATGAGAAT<br>GAGATCACCAAAGTGCGAAAAGTTACTTTTCAATGGACTGAACCAGATG<br>ATTGTCATAGAACTGGGCACCAATCCGCTGAAGAGCTCAGGAATTGAA<br>AATGGGGCTTTCCAGGGAATGAAGAAGCTCTCCTACATCCGCATTGCT<br>GATACCAATATCACCAGCATTCCTCAAGGTCTTCCTCCTTCCCTTACG<br>GAATTACATCTTGATGGCAACAAAATCAGCAGAGTTGATGCAGCTAGC<br>CTGAAAGGACTGAATAATTTGGCTAAGTTGGGATTGAGTTTCAACAGC<br>ATCTCTGCTGTTGACAATGGCTCTCTGGCCAACACGCCTCATCTGAGG<br>GAGCTTCACTTGGACAACAACAAGCTTACCAGAGTACCTGGTGGGCTG<br>GCAGAGCATAAGTACATCCAGGTTGTCTACCTTCATAACAACAATATC<br>TCTGTAGTTGGATCAAGTGACTTCTGCCCACCTGGACACAACACCAAA<br>AAGGCTTCTTATTCGGGTGTGAGTCTTTTCAGCAACCCGGTCCAGTAC<br>TGGGAGATACAGCCATCCACCTTCAGATGTGTCTACGTGCGCTCTGCC<br>ATTCAACTCGGAAACTATAAGTAA |
| 26 | Insert vMyx-Triple red (hu Decorin-hu Il-12-dsRed) | AAAAATTGAAATTTTATTTTTTTTTTTGGAATATAAATAATGAAGGC<br>CACTATCATCCTCCTTCTGCTTGCACAAGTTTCCTGGGCTGGACCGTT<br>TCAACAGAGAGGCTTATTTGACTTTATGCTAGAAGATGAGGCTTCTGG<br>GATAGGCCCAGAAGTTCCTGATGACCGCGACTTCGAGCCCTCCCTAGG<br>CCCAGTGTGCCCCTTCCGCTGTCAATGCCATCTTCGAGTGGTCCAGTG<br>TTCTGATTTGGGTCTGGACAAAGTGCCAAAGGATCTTCCCCCTGACAC<br>AACTCTGCTAGACCTGCAAAACAACAAAATAACCGAAATCAAAGATGG<br>AGACTTTAAGAACCTGAAGAACCTTCACGCATTGATTCTTGTCAACAA<br>TAAAATTAGCAAAGTTAGTCCTGGAGCATTTACACCTTTGGTGAAGTT<br>GGAACGACTTTATCTGTCCAAGAATCAGCTGAAGGAATTGCCAGAAAA<br>AATGCCCAAAACTCTTCAGGAGCTGCGTGCCCATGAGAATGAGATCAC<br>CAAAGTGCGAAAAGTTACTTTTCAATGGACTGAACCAGATGATTGTCA<br>TAGAACTGGGCACCAATCCGCTGAAGAGCTCAGGAATTGAAAATGGGG<br>CTTTCCAGGGAATGAAGAAGCTCTCCTACATCCGCATTGCTGATACCA<br>ATATCACCAGCATTCCTCAAGGTCTTCCTCCTTCCCTTACGGAATTAC<br>ATCTTGATGGCAACAAAATCAGCAGAGTTGATGCAGCTAGCCTGAAAG<br>GACTGAATAATTTGGCTAAGTTGGGATTGAGTTTCAQACAGCATCTCT<br>GCTGTTGACAATGGCTCTCTGGCCAACACGCCTCATCTGAGGGAGCTT<br>CACTTGGACAACAACAAGCTTACCAGAGTACCTGGTGGGCTGGCAGAG<br>CATAAGTACATCCAGGTTGTCTACCTTCATAACAACAATATCTCTGTA<br>GTTGGATCAAGTGACTTCTGCCCACCTGGACACAACACCAAAAAGGCT |

TABLE 5-continued

| SEQ ID NO | Name | Sequence |
|---|---|---|
| | | TCTTATTCGGGTGTGAGTCTTTTCAGCAACCCGGTCCAGTACTGGGAG
ATACAGCCATCCACCTTCAGATGTGTCTACGTGCGCTCTGCCATTCAA
CTCGGAAACTATAAGTAAATGTGTCACCAGCAGTTGGTCATCTCTTGG
TTTTCCCTGGTTTTTCTGGCATCTCCCCTCGTGGCCATATGGGAACTG
AAGAAAGATGTTTATGTCGTAGAATTGGATTGGTATCCGGATGCCCCT
GGAGAAATGTGGTCCTCACCTGTGACACCCCTGAAGAAGATGGTATC
ACCTGGACCTTGGACCAGAGCAGTGAGGTCTTAGGCTCTGGCAAAACC
CTGACCATCCAAGTCAAAGAGTTTGGAGATGCTGGCCAGTACACCTGT
CACAAAGGAGGCGAGGTTCTAAGCCATTCGCTCCTGCTGCTTCACAAA
AAGGAAGATGGAATTTGGTCCACTGATATTTTAAAGGACCAGAAAGAA
CCCAAAAATAAGACCTTTCTAAGATGCGAGGCCAAGAATTATTCTGGA
CGTTTCACCTGCTGGTGGCTGACGACAATCAGTACTGATTTGACATTC
AGTGTCAAAAGCAGCAGAGGCTCTTCTGACCCCCAAGGGGTGACGTGC
GGAGCTGCTACACTCTCTGCAGAGAGAGTCAGAGGGGACAACAAGGAG
TATGAGTACTCAGTGGAGTGCCAGGAGGACAGTGCCTGCCCAGCTGCT
GAGGAGAGTCTGCCCATTGAGGTCATGGTGGATGCCGTTCACAAGCTC
AAGTATGAAAACTACACCAGCAGCTTCTTCATCAGGGACATCATCAAA
CCTGACCCACCCAAGAACTTGCAGCTGAAGCCATTAAAGAATTCTCGG
CAGGTGGAGGTCAGCTGGGAGTACCCTGACACCTGGAGTACTCCACAT
TCCTACTTCTCCCTGACATTCTGCGTTCAGGTCCAGGGCAAGAGCAAG
AGAGAAAAGAAAGATAGAGTCTTCACGGACAAGACCTCAGCCACGGTC
ATCTGCCGCAAAAATGCCAGCATTAGCGTGCGGGCCCAGGACCGCTAC
TATAGCTCATCTTGGAGCGAATGGGCATCTGTGCCCTGCAGTTAGTAT
GCTAGTACGTCTCTCAAGGATAAGTAAGTAATATTAAGGTACGGGAGG
TATTGGACAGGCCGCAATAAAATATCTTTATTTTCATTACATCTGTGT
GTTGGTTTTTTGTGTGAATCGATAGTYACTAACATACGCTCTCCATCA
AAACAAAACGAAACAAAACAAACTAGCAAAATAGGCTGTCCCCAGTGC
AAGTGCAGGTGCCAGAACATTTCTCTGGCCTAACTGGCCGGTACCTGA
GCTCTAGTTTCACTTTCCCTAGTTTCACTTTCCCTAGTTTCACTTTCC
CTAGTTTCACTTTCCCTAGTTTCACTTTCCCCTCGAGGATATCAAGAT
CTGGCCTCGGCGGCCAGATGTGGCCCCCTGGGTCAGCCTCCAGCCACC
GCCCTCACCTGCCGCGGCCACAGGTCTGCATCCAGCGGCTCGCCCTGT
GTCCCTGCAGTGCCGGCTCAGCATGTGTCCAGCGCGCAGCCTCCTCCT
TGTGGCTACCCTGGTCCTCCTGGACCACCTCAGTTTGGCCAGAAACCT
CCCCGTGGCCACTCCAGACCCAGGAATGTTCCCATGCCTTCACCACTC
CCAAAACCTGCTGAGGGCCGTCAGCAACATGCTCCAGAAGGCCAGACA
AACTCTAGAATTTTACCCTTGCACTTCTGAAGAGATTGATCATGAAGA
TATCACAAAAGATAAAACCAGCACAGTGGAGGCCTGTTTACCATTGGA
ATTAACCAAGAATGAGAGTTGCCTAAATTCCAGAGAGACCTCTTTCAT
AACTAATGGGAGTTGCCTGGCCTCCAGAAAGACCTCTTTTATGATGGC
CCTGTGCCTTAGTAGTATTTATGAAGACTTGAAGATGTACCAGGTGGA
GTTCAAGACCATGAATGCAAAGCTTCTGATGGATCCTAAGAGGCAGAT
CTTTCTAGATCAAAACATGCTGGCAGTTATTGATGAGCTGATGCAGGC
CCTGAATTTCAACAGTGAGACTGTGCCACAAAAATCCTCCCTTGAAGA
ACCGGATTTTTATAAAACTAAAATCAAGCTCTGCATACTTCTTCATGC
TTTCAGAATTCGGGCAGTGACTATTGATAGAGTGATGAGCTATCTGAA
TGCTTCCTAAGAATTTCATTTTGTTTTTTTCTATGCTATAAATGGTGC
GCTCCTCCAAGAACGTCATCAAGGAGTTCATGCGCTTCAAGGTGCGCA
TGGAGGGCACCGTGAACGGCCACGAGTTCGAGATCGAGGGCGAGGGCG
AGGGCCGCCCCTACGAGGGCCACAACACCGTGAAGCTGAAGGTGACCA
AGGGCGGCCCCCTGCCCTTCGCCTGGGACATCCTGTCCCCCCAGTTCC
AGTACGGCTCCAAGGTGTACGTGAAGCACCCCGCCGACATCCCCGACT
ACAAGAAGCTGTCCTTCCCCGAGGGCTTCAAGTGGGAGCGCGTGATGA
ACTTCGAGGACGGCGGCGTGGTGACCGTGACCCAGGACTCCTCCCTGC
AGGACGGCTGCTTCATCTACAAGGTGAAGTTCATCGGCGTGAACTTCC
CCTCCGACGCGCCCGTAATGACAGAAGAAGACCATGGGCTGGAGGCC
TCCACCGAGCGCCTGTACCCCCGCGACGGCGTGCTGAAGGGCGAGATC
CACAAGGCCCTGAAGCTGAAGGACGGCGGCCACTACCTGGTGGAGTTC
AAGTCCATCTACATGGCCAAGAAGCCCGTGCAGCTGCCCGGCTACTAC
TACGTGGACTCCAAGCTGGACATCACCTCCCACAACGAGGACTACACC
ATCGTGGAGCAGTACGAGCGCACCGAGGGCCGCCACCACCTGTTCCTG
TAG |
| 27 | Insert vMyx-Triple white (hu Decorin-hu Il-12) | AAAAATTGAAATTTTATTTTTTTTTTTTGGAATATAAATAATGAAGGC
CACTATCATCCTCCTTCTGCTTGCACAAGTTTCCTGGGCTGGACCGTT
TCAACAGAGAGGCTTATTGGACTTTATGCTAGAAGATGAGGCTTCTGG
GATAGGCCCAGAAGTTCCTGATGACCGCGACTTCGAGCCCTCCCTAGG
CCCAGTGTGCCCCT TABLE 5-continued

| SEQ ID NO | Name | Sequence |
|---|---|---|
| | | TCTTGATGGCAACAAAATCAGCAGAGTTGATGCAGCTAGCCTGAAAGG<br>ACTGAATAATTTGGCTAAGTTGGGATTGAGTTTCAACAGCATCTCTGC<br>TGTTGACAATGGCTCTCTGGCCAACACGCCTCATCTGAGGGAGCTTCA<br>CTTGGACAACAACAAGCTTACCAGAGTACCTGGTGGGCTGGCAGAGCA<br>TAAGTACATCCAGGTTGTCTACCTTCATAACAACAATATCTCTGTAGT<br>TGGATCAAGTGACTTCTGCCCACCTGGACACAACACCAAAAAGGCTTC<br>TTATTCGGGTGTGAGTCTTTTCAGCAACCCGGTCCAGTACTGGGAGAT<br>ACAGCCATCCACCTTCAGATGTGTCTACGTGCGCTCTGCCATTCAACT<br>CGGAAACTATAAGTAAATGTGTCACCAGCAGTTGGTCATCTCTTGGTT<br>TTCCCTGGTTTTTCTGGCATCTCCCCTCGTGGCCATATGGGAACTGAA<br>GAAAGATGTTTATGTCGTAGAATTGGATTGGTATCCGGATGCCCCTGG<br>AGAAATGGTGGTCCTCACCTGTGACACCCCTGAAGAAGATGGTATCAC<br>CTGGACCTTGGACCAGAGCAGTGAGGTCTTAGGCTCTGGCAAAACCCT<br>GACCATCCAAGTCAAAGAGTTTGGAGATGCTGGCCAGTACACCTGTCA<br>CAAAGGAGGCGAGGTTCTAAGCCATTCGCTCCTGCTGCTTCACAAAAA<br>GGAAGATGGAATTTGGTCCACTGATATTTTAAAGGACCAGAAAGAACC<br>CAAAAATAAGACCTTTCTAAGATGCGAGGCCAAGAATTATTCTGGACG<br>TTTCACCTGCTGGTGGCTGACGACAATCAGTACTGATTTGACATTCAG<br>TGTCAAAAGCAGCAGAGGCTCTTCTGACCCCCAAGGGGTGACGTGCGG<br>AGCTGCTACACTCTCTGCAGAGAGTCAGAGGGGACAACAAGGAGTA<br>TGAGTACTCAGTGGAGTGCCAGGAGGACAGTGCCTGCCCAGCTGCTGA<br>GGAGAGTCTGCCCATTGAGGTCATGGTGGATGCCGTTCACAAGCTCAA<br>GTATGAAAACTACACCAGCAGCTTCTTCATCAGGGACATCATCAAACC<br>TGACCCACCCAAGAACTTGCAGCTGAAGCCATTAAAGAATTCTCGGCA<br>GGTGGAGGTCAGCTGGGAGTACCCTGACACCTGGAGTACTCCACATTC<br>CTACTTCTCCCTGACATTCTGCGTTCAGGTCCAGGGCAAGAGCAAGAG<br>AGAAAAGAAAGATAGAGTCTTCACGGCACAAGACCTCAGCCACGGTCA<br>TCTGCCGAAAAATGCCAGCATTAGCGTGCGGGCCCAGGACCGCTACT<br>ATAGCTCATCTTGGAGCGAATGGGCATCTGTGCCCTGCAGTTAGTATG<br>CTAGTACGTCTCTCAAGGATAAGTAAGTAATATTAAGGTACGGGAGGT<br>ATTGGACAGGCCGCAATAAAATATCTTTATTTTCATTACATCTGTGTG<br>TTGGTTTTTTGTGTGAATCGATAGTACTAACATACGCTCTCCATCAAA<br>ACAAAACGAAACAAAACAAACTAGCAAAATAGGCTGTCCCCAGTGCAA<br>GTGCAGGTGCCAGAACATTTCTCTGGCCTAACTGGCCGGTACCTGAGC<br>TCTAGTTTCACTTTCCCTAGTTTCACTTTCCCTAGTTTCACTTTCCCT<br>AGTTTCACTTTCCCTAGTTTCACTTTCCCCTCGAGGATATCAAGATCT<br>GGCCTCGGCGGCCAGATGTGGCCCCCTGGGTCAGCCTCCCAGCCACCG<br>CCCTCACCTGCCGCGGCCACAGGTCTGCATCCAGCGGCTCGCCCTGTG<br>TCCCTGCAGTGCCGGCTCAGCATGTGTCCAGCGCGCAGCCTCCTCCTT<br>GTGGCTACCCTGGTCCTCCTGGACCACCTCAGTTTGGCCAGAAACCTC<br>CCCGTGGCCACTCCAGACCCAGGAATGTTCCCATGCCTTCACCACTCC<br>CAAAACCTGCTGAGGGCCGTCAGCAACATGCTCCAGAAGGCCAGACAA<br>ACTCTAGAATTTTACCCTTGCACTTCTGAAGAGATTGATCATGAAGAT<br>ATCACAAAAGATAAAACCAGCACAGTGGAGGCCTGTTTACCATTGGAA<br>TTAACCAAGAATGAGAGTTGCCTAAATTCCAGAGAGACCTCTTTCATA<br>ACTAATGGGAGTTGCCTGGCCTCCAGAAAGACCTCTTTTATGATGGCC<br>CTGTGCCTTAGTAGTATTTATGAAGCTTGAAGATGTACCAGGTGGAG<br>TTCAAGACCATGAATGCAAAGCTTCTGATGGATCCTAAGAGGCAGATC<br>TTTCTAGATCAAAACATGCTGGCAGTTATTGATGAGCTGATGCAGGCC<br>CTGAATTTCAACAGTGAGACTGTGCCACAAAAATCCTCCCTTGAAGAA<br>CCGGATTTTTATAAAACTAAAATCAAGCTCTGCATACTTCTTCATGCT<br>TTCAGAATTCGGGCAGTGACTATTGATAGAGTGATGAGCTATATCTGA<br>ATGCTTCCTAA |
| 28 | hu IL-12 A (p40) | MWPPGSASQPPPSPAAATGLHPAARPVSLQCRLSMCPARSLLLVATLV<br>LLDHLSLARNLPVATPDPGMFPCLHHSQNLLRAVSNMLQKARQTLEFY<br>PCTSEEIDHEDITKDKTSTVEACLPLELTKNESCLNSRETSFITNGSC<br>LASRKTSFMMALCLSSIYEDLKMYQVEFKTMNAKLLMDPKRQIFLDQN<br>MLAVIDELMQALNFNSETVPQKSSLEEPDFYKTKIKLCILLHAFRIRA<br>VTIDRVMSYLNAS* |
| 29 | huIL-12B (p35) | MCHQQLVISWFSLVFLASPLVAIWELKKDVYVVELDWYPDAPGEMVVL<br>TCDTPEEDGITWTLDQSSEVLGSGKTLTIQVKEFGDAGQYTCHKGGEV<br>LSHSLLLLHKKEDGIWSTDILKDQKEPKNKTFLRCEAKNYSGRFTCWW<br>LTTISTDLTFSVKSSRGSSDPQGVTCGAATLSAERVRGDNKEYEYSVE<br>CQEDSACPAAEESLPIEVMVDAVHKLKYENYTSSFFIRDIIKPDPPKN<br>LQLKPLKNSRQVEVSWEYPDTWSTPHSYFSLTFCVQVQGKSKREKKDR<br>VFTDKTSATVICRKNASISVRAQDRYYSSSWSEWASVPCS* |
| 30 | dsRed | MVRSSKNVIKEFMRFKVRMEGTVNGHEFEIEGEGEGRPYEGHNTVKLK<br>VTKGGPLPFAWDILSPQFQYGSKVYVKHPADIPDYKKLSFPEGFKWER<br>VMNFEDGGVVTVTQDSSLQDGCFIYKVKFIGVNFPSDGPVMQKKTMGW<br>EASTERLYPRDGVLKGEIHKALKLKDGGHYLVEFKSIYMAKKPVQLPG<br>YYYVDSKLDITSHNEDYTIVEQYERTEGRHHLFL |
| 31 | hu TNF-a | MSTESMIRDVELAEEEALPKKTGGPQGSRRCLFLSLFSFLIVAGATTLF<br>CLLHFGVIGPQREEFPRDLSLISPLAQAVRSSSRTPSDKPVAHVVANP<br>QAEGQLQWLNRRANALLANGVELRDNQLVVPSEGLYLIYSQVLFKGQG |

TABLE 5-continued

| SEQ ID NO | Name | Sequence |
|---|---|---|
| | | CPSTHVLLTHTISRIAVSYQTKVNLLSAIKSPCQRETPEGAEAKPWYE<br>PIYLGGVFQLEKGDRLSAEINRPDYLDFAESGQVYFGIIAL |
| 32 | Hu Decorin | MKATIILLLLAQVSWAGPFQQRGLFDFMLEDEASGIGPEVPDDRDFE<br>PSLGPVCPFRCQCHLRVVQCSDLGLDKVPKDLPPDTTLLDLQNNKIT<br>EIKDGDFKNLKNLHALILVNNKISKVSPGAFTPLVKLERLYLSKNQL<br>KELPEKMPKTLQELRAHENEITKVRKVTFNGLNQMIVIELGTNPLKS<br>SGIENGAFQGMKKLSYIRIADTNITSIPQGLPPSLTELHLDGNKISR<br>VDAASLKGLNNLAKLGLSFNSISAVDNGSLANTPHLRELHLDNNKLT<br>RVPGGLAEHKYIQVVYLHNNNISVVGSSDFCPPGHNTKKASYSGVSL<br>FSNPVQYWEIQPSTFRCVYVRSAIQLGNYK* |
| 33 | Linker | GGGGS |
| 34 | Linker | GGGS |
| 35 | Linker | GG |
| 36 | Linker | KESGSVSSEQLAQFRSLD |
| 37 | Linker | EGKSSGSGSESKST |
| 38 | Linker | GSAGSAAGSGEF |
| 39 | Linker | EAAAK |
| 40 | Linker | EAAAR |
| 41 | Linker | PAPAP |
| 42 | Linker | AEAAAKEAAAKA |
| 43 | Linker | VPGVGVPGVG |
| 44 | huIL-12B (p40) | ATGTGTCACCAGCAGTTGGTCATCTCTTGGTTTTCCCTGGTTTTTCTG<br>GCATCTCCCCTCGTGGCCATATGGGAACTGAAGAAAGATGTTTATGTC<br>GTAGAATTGGATTGGTATCCGGATGCCCCTGGAGAAATGGTGGTCCTC<br>ACCTGTGACACCCCTGAAGAAGATGGTATCACCTGGACCTTGGACCAG<br>AGCAGTGAGGTCTTAGGCTCTGGCAAAACCCTGACCATCCAAGTCAAA<br>GAGTTTGGAGATGCTGGCCAGTACACCTGTCACAAAGGAGGCGAGGTT<br>CTAAGCCATTCGCTCCTGCTGCTTCACAAAAAGGAAGATGGAATTTGG<br>TCCACTGATATTTTAAAGGACCAGAAAGAACCCAAAAATAAGACCTTT<br>CTAAGATGCGAGGCCAAGAATTATTCTGGACGTTTCACCTGCTGGTGG<br>CTGACGACAATCAGTACTGATTTGACATTCAGTGTCAAAAGCAGCAGA<br>GGCTCTTCTGACCCCCAAGGGGTGACGTGCGGAGCTGCTACACTCTCT<br>GCAGAGAGAGTCAGAGGGGACAACAAGGAGTATGAGTACTCAGTGGAG<br>TGCCAGGAGGACAGTGCCTGCCCAGCTGCTGAGGAGAGTCTGCCCATT<br>GAGGTCATGGTGGATGCCGTTCACAAGCTCAAGTATGAAAACTACACC<br>AGCAGCTTCTTCATCAGGGACATCATCAAACCTGACCCACCCAAGAAC<br>TTGCAGCTGAAGCCATTAAAGAATTCTCGGCAGGTGGAGGTCAGCTGG<br>GAGTACCCTGACACCTGGAGTACTCCACATTCCTACTTCTCCCTGACA<br>TTCTGCGTTCAGGTCCAGGGCAAGAGCAAGAGAGAAAAGAAAGATAGA<br>GTCTTCACGGACAAGACCTCAGCCACGGTCATCTGCCGCAAAAATGCC<br>AGCATTAGCGTGCGGGCCCAGGACCGCTACTATAGCTCATCTTGGAGC<br>GAATGGGCATCTGTGCCCTGCAGTTAG |
| 45 | Membrane bound<br>hu TNF-a | MSTESMIRDVELAEEALPKKTGGPQGSRRCLFLSLFSFLIVAGATTLF<br>CLLHFGVIGPQREEFPRDLSLISPLAQADEPVAHVVANPQAEGQLQWL<br>NRRANALLANGVELRDNQLVVPSEGLYLIYSQVLFKGQGCPSTHVLLT<br>HTISRIAVSYQTKVNLLSAIKSPCQRETPEGAEAKPWYEPIYLGGVFQ<br>LEKGDRLSAEINRPDYLDFAESGQVYFGIIAL |
| 46 | Membrane bound<br>hu TNF-a | ATGAGCACTGAAAGCATGATCCGGGACGTGGAGCTGGCCGAGGAGGCG<br>CTCCCCAAGAAGACAGGGGGGCCCCAGGGCTCCAGGCGGTGCTTGTTC<br>CTCAGCCTCTTCTCCTTCCTGATCGTGGCAGGCGCCACCACGCTCTTC<br>TGCCTGCTGCACTTTGGAGTGATCGGCCCCCAGAGGGAAGAGTTCCCC<br>AGGGACCTCTCTCTAATCAGCCCTCTGGCCCAGGCAGATGAGCCTGTA<br>GCCCATGTTGTAGCAAACCCTCAAGCTGAGGGGCAGCTCCAGTGGCTG<br>AACCGCCGGGCCAATGCCCTCCTGGCCAATGGCGTGGAGCTGAGAGAT<br>AACCAGCTGGTGGTGCCATCAGAGGGCCTGTACCTCATCTACTCCCAG<br>GTCCTCTTCAAGGGCCAAGGCTGCCCCTCCACCCATGTGCTCCTCACC<br>CACACCATCAGCCGCATCGCCGTCTCCTACCAGACCAAGGTCAACCTC<br>CTCTCTGCCATCAAGAGCCCCTGCCAGAGGGAGACCCCAGAGGGGGCT<br>GAGGCCAAGCCCTGGTATGAGCCCATCTATCTGGGAGGGGTCTTCCAG<br>CTGGAGAAGGGTGACCGACTCAGCGCTGAGATCAATCGGCCCGACTAT<br>CTCGACTTTGCCGAGTCTGGGCAGGTCTACTTTGGGATCATTGCCCTG<br>TAG |

TABLE 5-continued

| SEQ ID NO | Name | Sequence |
|---|---|---|
| 47 | Insert vMyx-Triple IL-12 High (hu Decorin-mo IL-12-dsRed) | AAAATTGAAATTTTATTTTTTTTTTTGGAATATAAATAATGAAGGCC<br>ACTATCATCCTCCTTCTGCTTGCACAAGTTTCCTGGGCTGGACCGTTT<br>CAACAGAGAGGCTTATTTGACTTTATGCTAGAAGATGAGGCTTCTGGG<br>ATAGGCCCAGAAGTTCCTGATGACCGCGACTTCGAGCCCTCCCTAGGC<br>CCAGTGTGCCCCTTCCGCTGTCAATGCCATCTTCGAGTGGTCCAGTGT<br>TCTGATTTGGGTCTGGACAAAGTGCCAAAGGATCTTCCCCCTGACACA<br>ACTCTGCTAGACCTGCAAAACAACAAAATAACCGAAATCAAAGATGGA<br>GACTTTAAGAACCTGAAGAACCTTCACGCATTGATTCTTGTCAACAAT<br>AAAATTAGCAAAGTTAGTCCTGGAGCATTTACACCTTTGGTGAAGTTG<br>GAACGACTTTATCTGTCCAAGAATCAGCTGAAGGAATTGCCAGAAAAA<br>ATGCCCAAAACTCTTCAGGAGCTGCGTGCCCATGAGAATGAGATCACC<br>AAAGTGCGAAAAGTTACTTTCAATGGACTGAACCAGATGATTGTCATA<br>GAACTGGGCACCAATCCGCTGAAGAGCTCAGGAATTGAAAATGGGGCT<br>TTCCAGGGAATGAAGAAGCTCTCCTACATCCGCATTGCTGATACCAAT<br>ATCACCAGCATTCCTCAAGGTCTTCCTCCTTCCCTTACGGAATTACAT<br>CTTGATGGCAACAAAATCAGCAGAGTTGATGCAGCTAGCCTGAAAGGA<br>CTGAATAATTTGGCTAAGTTGGGATTGAGTTTCAACAGCATCTCTGCT<br>GTTGACAATGGCTCTCTGGCCAACACGCCTCATCTGAGGGAGCTTCAC<br>TTGGACAACAACAAGCTTACCAGAGTACCTGGTGGGCTGGCAGAGCAT<br>AAGTACATCCAGGTTGTCTACCTTCATAACAACAATATCTCTGTAGTT<br>GGATCAAGTGACTTCTGCCCACCTGGACACAACACCAAAAAGGCTTCT<br>TATTCGGGTGTGAGTCTTTTCAGCAACCCGGTCCAGTACTGGGAGATA<br>CAGCCATCCACCTTCAGATGTGTCTACGTGCGCTCTGCCATTCAACTC<br>GGAAACTATAAGTAAAAAATTGAAATTTTATTTTTTTTTTGGAATA<br>TAAATAATGTGTCCTCAGAAGCTAACCATCTCCTGGTTTGCCATCGTT<br>TTGCTGGTGTCTCCACTCATGGCCATGTGGGAGCTGGAGAAAGACGTT<br>TATGTTGTAGAGGTGGACTGGACTCCCGATGCCCCTGGAGAAACAGTG<br>AACCTCACCTGTGACACGCCTGAAGAAGATGACATCACCTGGACCTCA<br>GACCAGAGACATGGAGTCATAGGCTCTGGAAAGACCCTGACCATCACT<br>GTCAAAGAGTTTCTAGATGCTGGCCAGTACACCTGCCACAAAGGAGGC<br>GAGACTCTGAGCCACTCACATCTGCTGCTCCACAAGAAGGAAAATGGA<br>ATTTGGTCCACTGAAATTTTAAAAAATTTCAAAAACAAGACTTTCCTG<br>AAGTGTGAAGCACCAAATTACTCCGGACGGTTCACGTGCTCATGGCTG<br>GTGCAAAGAAACATGGACTTGAAGTTCAACATCAAGAGCAGTAGCAGT<br>TCCCCTGACTCTCGGGCAGTGACATGTGGAATGGCGTCTCTGTCTGCA<br>GAGAAGGTCACACTGGACCAAAGGGACTATGAGAAGTATTCAGTGTCC<br>TGCCAGGAGGATGTCACCTGCCCAACTGCCGAGGAGACCCTGCCCATT<br>GAACTGGCGTTGGAAGCACGGCAGCAGAATAAATATGAGAACTACAGC<br>ACCAGCTTCTTCATCAGGGACATCATCAAACCAGACCCGCCCAAGAAC<br>TTGCAGATGAAGCCTTTGAAGAACTCACAGGTGGAGGTCAGCTGGGAG<br>TACCCTGACTCCTGGAGCACTCCCCATTCCTACTTCTCCCTCAAGTTC<br>TTTGTTCGAATCCAGCGCAAGAAAGAAAAGATGAAGGAGACAGAGGAG<br>GGGTGTAACCAGAAAGGTGCGTTCCTCGTAGAGAAGACATCTACCGAA<br>GTCCAATGCAAAGGCGGGAATGTCTGCGTGCAAGCTCAGGATCGCTAT<br>TACAATTCCTCATGCAGCAAGTGGGCATGTGTTCCCTGCAGGGTCCGA<br>TCCGTTCCTGGAGTAGGGGTACCTGGAGTGGGCATGGTCAGCGTTCCA<br>ACAGCCTCACCCTCGGCATCCAGCAGCTCCTCTCAGTGCCGGTCCAGC<br>ATGTGTCAATCACGCTACCTCCTCTTTTTGGCCACCCTTGCCCTCCTA<br>AACCACCTCAGTTTGGCCAGGGTCATTCCAGTCTCTGGACCTGCCAGG<br>TGTCTTAGCCAGTCCCGAAACCTGCTGAAGACCACAGATGACATGGTG<br>AAGACGGCCAGAGAAAACTGAAACATTATTCCTGCACTGCTGAAGAC<br>ATCGATCATGAAGAC |
| 48 | Insert vMyx-Triple IL-12 low (hu Decorin-mo Il-12-dsRed) | AAAATTGAAATTTTATTTTTTTTTTTGGAATATAAATAATGAAGGCC<br>ACTATCATCCTCCTTCTGCTTGCACAAGTTTCCTGGGCTGGACCGTTT<br>CAACAGAGAGGCTTATTTGACTTTATGCTAGAAGATGAGGCTTCTGGG<br>ATAGGCCCAGAAGTTCCTGATGACCGCGACTTCGAGCCCTCCCTAGGC<br>CCAGTGTGCCCCTTCCGCTGTCAATGCCATCTTCGAGTGGTCCAGTGT<br>TCTGATTTGGGTCTGGACAAAGTGCCAAAGGATCTTCCCCCTGACACA<br>ACTCTGCTAGACCTGCAAAACAACAAAATAACCGAAATCAAAGATGGA<br>GACTTTAAGAACCTGAAGAACCTTCACGCATTGATTCTTGTCAACAAT<br>AAAATTAGCAAAGTTAGTCCTGGAGCATTTACACCTTTGGTGAAGTTG<br>GAACGACTTTATCTGTCCAAGAATCAGCTGAAGGAATTGCCAGAAAAA<br>ATGCCCAAAACTCTTCAGGAGCTGCGTGCCCATGAGAATGAGATCACC<br>AAAGTGCGAAAAGTTACTTTCAATGGACTGAACCAGATGATTGTCATA<br>GAACTGGGCACCAATCCGCTGAAGAGCTCAGGAATTGAAAATGGGGCT<br>TTCCAGGGAATGAAGAAGCTCTCCTACATCCGCATTGCTGATACCAAT<br>ATCACCAGCATTCCTCAAGGTCTTCCTCCTTCCCTTACGGAATTACAT<br>CTTGATGGCAACAAAATCAGCAGAGTTGATGCAGCTAGCCTGAAAGGA<br>CTGAATAATTTGGCTAAGTTGGGATTGAGTTTCAACAGCATCTCTGCT<br>GTTGACAATGGCTCTCTGGCCAACACGCCTCATCTGAGGGAGCTTCAC<br>TTGGACAACAACAAGCTTACCAGAGTACCTGGTGGGCTGGCAGAGCAT<br>AAGTACATCCAGGTTGTCTACCTTCATAACAACAATATCTCTGTAGTT<br>GGATCAAGTGACTTCTGCCCACCTGGACACAACACCAAAAAGGCTTCT<br>TATTCGGGTGTGAGTCTTTTCAGCAACCCGGTCCAGTACTGGGAGATA<br>CAGCCATCCACCTTCAGATGTGTCTACGTGCGCTCTGCCATTCAACTC<br>GGAAACTATAAGTAAGCTTGGACTCCTGTTGATAGATCCAGAAAATTG<br>AAATTTATTTTTTTTTTTGGAATATAAATAATGTGTCCTCAGAAGC |

TABLE 5-continued

| SEQ ID NO | Name | Sequence |
|---|---|---|
| | | TAACCATCTCCTGGTTTGCCATCGTTTTGCTGGTGTCTCCACTCATGG |
| | | CCATGTGGGAGCTGGAGAAAGACGTTTATGTTGTAGAGGTGGACTGGA |
| | | CTCCCGATGCCCCTGGAGAAACAGTGAACCTCACCTGTGACACGCCTG |
| | | AAGAAGATGACATCACCTGGACCTCAGACCAGAGACATGGAGTCATAG |
| | | GCTCTGGAAAGACCCTGACCATCACTGTCAAAGAGTTTCTAGATGCTG |
| | | GCCAGTACACCTGCCACAAAGGAGGCGAGACTCTGAGCCACTCACATC |
| | | TGCTGCTCCACAAGAAGGAAAATGGAATTTGGTCCACTGAAATTTTAA |
| | | AAAATTTCAAAAACAAGACTTTCCTGAAGTGTGAAGCACCCAAATTACT |
| | | CCGGACGGTTCACGTGCTCATGGCTGGTGCAAAGAAACATGGACTTGA |
| | | AGTTCAACATCAAGAGCAGTAGCAGTTCCCCTGACTCTCGGGCAGTGA |
| | | CATGTGGAATGGCGTCTCTGTCTGCAGAGAAGGTCACACTGGACCAAA |
| | | GGGACTATGAGAAGTATTCAGTGTCCTGCCAGGAGGATGTCACCTGCC |
| | | CAACTGCCGAGGAGACCCTGCCCATTGAACTGGCGTTGGAAGCACGGC |
| | | AGCAGAATAAATATGAGAACTACAGCACCAGCTTCTTCATCAGGGACA |
| | | TCATCAAACCAGACCCGCCCAAGAACTTGCAGATGAAGCCTTTGAAGA |
| | | ACTCACAGGTGGAGGTCAGCTGGGAGTACCCTGACTCCTGGAGCACTC |
| | | CCCATTCCTACTTCTCCCTCAAGTTCTTTGTTCGAATCCAGCGCAAGA |
| | | AAGAAAAGATGAAGGAGACAGAGGAGGGGTGTAACCAGAAAGGTGCGT |
| | | TCCTCGTAGAGAAGACATCTACCGAAGTCCAATGCAAAGGCGGGAATG |
| | | TCTGCGTGCAAGCTCAGGATCGCTATTACAATTCCTCATGCAGCAAGT |
| | | GGGCATGTGTTCCCTGCAGGGTCCGATCCTAGTATGCTAGTACGTCTC |
| | | TCAAGGATAAGTAAGTAATATTAAGGTACGGGAGGTATTGGACAGGCC |
| | | GCAATAAAATATCTTTATTTTCATTACATCTGTGTGTTGGTTTTTGT |
| | | GTGAATCGATAGTACTAACATACGCTCTCCATCAAAACAAAACGAAAC |
| | | AAAACAAACTAGCAAAATAGGCTGTCCCCAGTGCAAGTGCAGGTGCCA |
| | | GAACATTTCTCTGGCCTAACTGGCCGGTACCTGAGCTCTAGTTTCACT |
| | | TTCCCTAGTTTCACTTTCCCTAGTTTCACTTTCCCTAGTTTCACTTTC |
| | | CCTAGTTTCACTTTCCCCTCGAGGATATCAAGATCTGGCCTCGGCGGC |
| | | CAGATGGTCAGCGTTCCAACAGCCTCACCCTCGGCATCCAGCAGCTCC |
| | | TCTCAGTGCCGGTCCAGCATGTGTCAATCACGCTACCTCCTCTTTTTG |
| | | GCCACCCTTGCCCTCCTAAACCACCTCAGTTTGGCCAGGGTCATTCCA |
| | | GTCTCTGGACCTGCCAGGTGTCTTAGCCAGTCCCGAAACCTGCTGAAG |
| | | ACCACAGATGACATGGTGAAGACGGCCAGAGAAAAACTGAAACATTAT |
| | | TCCTGCACTGCTGAAGACATCGATCATGAAGACATCACACGGGACCAA |
| | | ACCAGCACATTGAAGACCTGTTTACCACTGGAACTACACAAGAACGAG |
| | | AGTTGCCTGGCTACTAGAGAGACTTCTTCCACAACAAGAGGGAGCTGC |
| | | CTGCCCCCACAGAAGACGTCTTTGATGATGACCCTGTGCCTTGGTAGC |
| | | ATCTATGAGGACTTGAAGATGTACCAGACAGAGTTCCAGGCCATCAAC |
| | | GCAGCACTTCAGAATCACAACCATCAGCAGATCATTCTAGACAAGGGC |
| | | ATGCTGGTGGCCATCGATGAGCTGATGCAGTCTCTGAATCATAATGGC |
| | | GAGACTCTGCGCCAGAAACCTCCTGTGGGAGAAGCAGACCCTTACAGA |
| | | GTGAAAATGAAGCTCTGCATCCTGCTTCACGCCTTCAGCACCCGCGTC |
| | | GTGACCATCAACAGGGTGATGGGCTATCTGAGCTCCGCCTGAACAACT |
| | | TTGTATAATAAAGTTGCTGAATTTCATTTTGTTTTTTCTATGCTATA |
| | | AATGGTGCGCTCCTCCAAGAACGTCATCAAGGAGTTCATGCGCTTCAA |
| | | GGTGCGCATGGAGGGCACCGTGAACGGCCACGAGTTCGAGATCGAGGG |
| | | CGAGGGCGAGGGCCGCCCCTACGAGGGCCACAACACCGTGAAGCTGAA |
| | | GGTGACCAAGGGCGGCCCCCTGCCCTTCGCCTGGGACATCCTGTCCCC |
| | | CCAGTTCCAGTACGGCTCCAAGGTGTACGTGAAGCACCCCGCCGACAT |
| | | CCCCGACTACAAGAAGCTGTCCTTCCCCGAGGGCTTCAAGTGGGAGCG |
| | | CGTGATGAACTTCGAGGACGGCGGCGTGGTGACCGTGACCCAGGACTC |
| | | CTCCCTGCAGGACGGCTGCTTCATCTACAAGGTGAAGTTCATCGGCGT |
| | | GAACTTCCCCTCCGACGGCCCCGTAATGCAGAAGAAGACCATGGGCTG |
| | | GGAGGCCTCCACCGAGCGCCTGTACCCCCGCGACGGCGTGCTGAAGGG |
| | | CGAGATCCACAAGGCCCTGAAGCTGAAGGACGGCGGCCACTACCTGGT |
| | | GGAGTTCAAGTCCATCTACATGGCCAAGAAGCCCGTGCAGCTGCCCGG |
| | | CTACTACTACGTGGACTCCAAGCTGGACATCACCTCCCACAACGAGGA |
| | | CTACACCATCGTGGAGCAGTACGAGCGCACCGAGGGCCGCCACCACCT |
| | | GTTCCTGTAG |
| 49 | Insert vMYX-membrane bound TNF -eGFP | AAAAATTGAAATTTTATTTTTTTTTTTGGAATATAAATAATG TABLE 5-continued

| SEQ ID NO | Name | Sequence |
|---|---|---|
|  |  | ATGCCACCTACGGCAAGCTGACCCTGAAGTTCATCTGCACCACCGGCA<br>AGCTGCCCGTGCCCTGGCCCACCCTCGTGACCACCCTGACCTACGGCG<br>TGCAGTGCTTCAGCCGCTACCCCGACCACATGAAGCAGCACGACTTCT<br>TCAAGTCCGCCATGCCCGAAGGCTACGTCCAGGAGCGCACCATCTTCT<br>TCAAGGACGACGGCAACTACAAGACCCGCGCCGAGGTGAAGTTCGAGG<br>GCGACACCCTGGTGAACCGCATCGAGCTGAAGGGCATCGACTTCAAGG<br>AGGACGGCAACATCCTGGGGCACAAGCTGGAGTACAACTACAACAGCC<br>ACAACGTCTATATCATGGCCGACAAGCAGAAGAACGGCATCAAGGTGA<br>ACTTCAAGATCCGCCACAACATCGAGGACGGCAGCGTGCAGCTCGCCG<br>ACCACTACCAGCAGAACACCCCCATCGGCGACGGCCCCGTGCTGCTGC<br>CCGACAACCACTACCTGAGCACCCAGTCCGCCCTGAGCAAAGACCCCA<br>ACGAGAAGCGCGATCACATGGTCCTGCTGGAGTTCGTGACCGCCGCCG<br>GGATCACTCTCGGCATGGACGAGCTGTACAAGTAA |
| 50 | Mouse IL-12 single polypeptide | MCPQKLTISWFAIVLLVSPLMAMWELEKDVYVVEVDWTPDAPGETVNL<br>TCDTPEEDDITWTSDQRHGVIGSGKTLTITVKEFLDAGQYTCHKGGET<br>LSHSHLLLHKKENGIWSTEILKNFKNKTFLKCEAPNYSGRFTCSWLVQ<br>RNMDLKFNIKSSSSSPDSRAVTCGMASLSAEKVTLDQRDYEKYSVSCQ<br>EDVTCPTAEETLPIELALEARQQNKYENYSTSFFIRDIIKPDPPKNLQ<br>MKPLKNSQVEVSWEYPDSWSTPHSYFSLKFFVRIQRKKEKMKETEEGC<br>NQKGAFLVEKTSTEVQCKGGNVCVQAQDRYYNSSCSKWACVPCRVRSV<br>PGVGVPGVGMVSVPTASPSASSSSSQCRSSMCQSRYLLFLATLALLNH<br>LSLARVIPVSGPARCLSQSRNLLKTTDDMVKTAREKLKHYSCTAEDID<br>HED |
| 51 | Mouse IL-12 B (p40) | MCPQKLTISWFAIVLLVSPLMAMWELEKDVYVVEVDWTPDAPGETVNL<br>TCDTPEEDDITWTSDQRHGVIGSGKTLTITVKEFLDAGQYTCHKGGET<br>LSHSHLLLHKKENGIWSTEILKNFKNKTFLKCEAPNYSGRFTCSWLVQ<br>RNMDLKFNIKSSSSSPDSRAVTCGMASLSAEKVTLDQRDYEKYSVSCQ<br>EDVTCPTAEETLPIELALEARQQNKYENYSTSFFIRDIIKPDPPKNLQ<br>MKPLKNSQVEVSWEYPDSWSTPHSYFSLKFFVRIQRKKEKMKETEEGC<br>NQKGAFLVEKTSTEVQCKGGNVCVQAQDRYYNSSCSKWACVPCRVRS |
| 52 | Truncated mouse IL-12 A (p35) | MVSVPTASPSASSSSSQCRSSMCQSRYLLFLATLALLNHLSLARVIPV<br>SGPARCLSQSRNLLKTTDDMVKTAREKLKHYSCTAEDIDHED |
| 53 | Mouse IL-12A (p35) | MVSVPTASPSASSSSSQCRSSMCQSRYLLFLATLALLNHLSLARVIPV<br>SGPARCLSQSRNLLKTTDDMVKTAREKLKHYSCTAEDIDHEDITRDQT<br>STLKTCLPLELHKNESCLATRETSSTTRGSCLPPQKTSLMMTLCLGSI<br>YEDLKMYQTEFQAINAALQNHNHQQIILDKGMLVAIDELMQSLNHNGE<br>TLRQKPPVGEADPYRVKMKLCILLHAFSTRVVTINRVMGYLSSA |

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A pharmaceutical composition comprising:
   i) a myxoma virus (MYXV) comprising a genetic modification at its M153 locus and a transgene encoding a cytokine or a cell matrix protein; and
   ii) a pharmaceutically acceptable excipient.

2. The pharmaceutical composition of claim 1, wherein the genetic modification comprises a disruption of M153 gene.

3. The pharmaceutical composition of claim 1, wherein the pharmaceutical composition is formulated for systemic administration.

4. The pharmaceutical composition of claim 1, wherein the pharmaceutical composition is formulated for local administration.

5. The pharmaceutical composition of claim 1, wherein the pharmaceutical composition is formulated for parenteral administration.

6. The pharmaceutical composition of claim 1, wherein the pharmaceutical composition comprises the MYXV at a dose of less than $1\times10^9$ focus forming units (FFU).

7. The pharmaceutical composition of claim 1, wherein the pharmaceutical composition comprises the MYXV at a dose of at least $1\times10^7$ focus forming units (FFU).

8. The pharmaceutical composition of claim 1, wherein upon administration of the MYXV to a subject, the transgene is effective to increase expression of at least two cytokines in a cancer cell of the subject at least about 30% compared to before the administering.

9. The pharmaceutical composition of claim 1, wherein the pharmaceutical composition comprises the MYXV at a dose effective to increase expression of at least two cytokines in a cancer cell of a subject at least about 30% upon administration of the MYXV to the subject.

10. The pharmaceutical composition of claim 8, wherein the at least two cytokines comprise IFN-γ, IL-2, IL-6, IL-10, IL-12, or TNF-α.

11. The pharmaceutical composition of claim 1, wherein the MYXV is effective to reduce viability of a cancer cell.

12. The pharmaceutical composition of claim 8, wherein the cancer cell comprises a solid tumor cell.

13. The pharmaceutical composition of claim 8, wherein the cancer cell comprises an osteosarcoma, triple negative breast cancer, or melanoma cell.

14. The pharmaceutical composition of claim 1, wherein the transgene encodes the cytokine.

15. The pharmaceutical composition of claim 8, wherein the at least two cytokines comprise TNF-α and IL-12.

16. The pharmaceutical composition of claim 1, wherein the transgene encodes human TNFα.

17. The pharmaceutical composition of claim 1, wherein the transgene encodes human IL-12.

18. The pharmaceutical composition of claim 1, wherein the transgene encodes the cell matrix protein.

19. The pharmaceutical composition of claim 1, wherein the transgene encodes human decorin.

20. The pharmaceutical composition of claim 1, wherein the transgene encodes the cytokine and the MYXV further comprises a second transgene that encodes the cell matrix protein.

\* \* \* \* \*